United States Patent
Gunderson et al.

(10) Patent No.: US 8,486,625 B2
(45) Date of Patent: *Jul. 16, 2013

(54) DETECTION OF NUCLEIC ACID REACTIONS ON BEAD ARRAYS

(75) Inventors: Kevin Gunderson, Encinitas, CA (US); John R. Stuelpnagel, Encinitas, CA (US); Mark S. Chee, Del Mar, CA (US)

(73) Assignee: Illumina, Inc., San Diego, CA (US)

( * ) Notice: Subject to any disclaimer, the term of this patent is extended or adjusted under 35 U.S.C. 154(b) by 0 days.
This patent is subject to a terminal disclaimer.

(21) Appl. No.: 12/212,585

(22) Filed: Sep. 17, 2008

(65) Prior Publication Data
US 2009/0186349 A1 Jul. 23, 2009

Related U.S. Application Data

(63) Continuation of application No. 11/238,826, filed on Sep. 28, 2005, now abandoned, which is a continuation of application No. 09/553,993, filed on Apr. 20, 2000, now abandoned, which is a continuation of application No. 09/535,854, filed on Mar. 27, 2000, now abandoned, which is a continuation-in-part of application No. 09/517,945, filed on Mar. 3, 2000, now Pat. No. 6,355,431, which is a continuation-in-part of application No. 09/513,362, filed on Feb. 25, 2000, now abandoned, which is a continuation-in-part of application No. 09/425,633, filed on Oct. 22, 1999, now abandoned.

(60) Provisional application No. 60/161,148, filed on Oct. 22, 1999, provisional application No. 60/160,927, filed on Oct. 22, 1999, provisional application No. 60/160,917, filed on Oct. 22, 1999, provisional application No. 60/135,051, filed on May 20, 1999, provisional application No. 60/135,053, filed on May 20, 1999, provisional application No. 60/135,123, filed on May 20, 1999, provisional application No. 60/130,089, filed on Apr. 20, 1999.

(51) Int. Cl.
*C12Q 1/68* (2006.01)
*C12M 1/36* (2006.01)
*C12P 19/34* (2006.01)
*C07H 21/04* (2006.01)

(52) U.S. Cl.
USPC ..... 435/6.1; 435/91.1; 435/91.52; 435/287.2; 536/23.1

(58) Field of Classification Search
None
See application file for complete search history.

(56) References Cited

U.S. PATENT DOCUMENTS 4,200,110 A 4/1980 Peterson et al.
4,234,681 A 11/1980 DeLuca-McElroy
(Continued)

FOREIGN PATENT DOCUMENTS

EP 0 139 489 5/1985
EP 0 238 332 9/1987
(Continued)

OTHER PUBLICATIONS

U.S. Appl. No. 09/398,833, filed Sep. 16, 1999, Rothberg et al.
(Continued)

*Primary Examiner* — Betty Forman
(74) *Attorney, Agent, or Firm* — Knobbe, Martens, Olson & Bear, LLP

(57) ABSTRACT

The present invention is directed to methods and compositions for the use of microsphere arrays to detect and quantify a number of nucleic acid reactions. The invention finds use in genotyping, i.e. the determination of the sequence of nucleic acids, particularly alterations such as nucleotide substitutions (mismatches) and single nucleotide polymorphisms (SNPs). Similarly, the invention finds use in the detection and quantification of a nucleic acid target using a variety of amplification techniques, including both signal amplification and target amplification. The methods and compositions of the invention can be used in nucleic acid sequencing reactions as well. All applications can include the use of adapter sequences to allow for universal arrays.

31 Claims, 28 Drawing Sheets

U.S. PATENT DOCUMENTS

| | | |
|---|---|---|
| 4,469,863 A | 9/1984 | Ts'o |
| 4,499,052 A | 2/1985 | Fulwyler |
| 4,582,789 A | 4/1986 | Sheldon et al. |
| 4,682,895 A | 7/1987 | Costello |
| 4,683,195 A | 7/1987 | Mullins et al. |
| 4,683,202 A | 7/1987 | Mullis et al. |
| 4,687,732 A | 8/1987 | Ward et al. |
| 4,751,177 A | 6/1988 | Stabinsky |
| 4,785,814 A | 11/1988 | Kane |
| 4,822,746 A | 4/1989 | Walt |
| 4,824,789 A | 4/1989 | Yafuso et al. |
| 4,876,187 A | 10/1989 | Duck et al. |
| 4,882,269 A | 11/1989 | Schneider et al. |
| 4,921,805 A | 5/1990 | Gebeyehu et al. |
| 4,971,903 A | 11/1990 | Hyman et al. |
| 4,988,617 A | 1/1991 | Landegren et al. |
| 4,999,306 A | 3/1991 | Yafuso et al. |
| 5,001,050 A | 3/1991 | Blanco et al. |
| 5,002,867 A | 3/1991 | Macevicz |
| 5,011,769 A | 4/1991 | Duck et al. |
| 5,028,545 A | 7/1991 | Soini |
| 5,034,506 A | 7/1991 | Summerton et al. |
| 5,035,996 A | 7/1991 | Hartley |
| 5,104,791 A | 4/1992 | Abbott et al. |
| 5,105,305 A | 4/1992 | Betzig et al. |
| 5,114,864 A | 5/1992 | Walt |
| 5,124,246 A | 6/1992 | Urdea et al. |
| 5,130,238 A | 7/1992 | Malek |
| 5,132,242 A | 7/1992 | Cheung |
| 5,143,853 A | 9/1992 | Walt |
| 5,175,082 A | 12/1992 | Jeffreys |
| 5,175,270 A | 12/1992 | Nilsen |
| 5,185,243 A | 2/1993 | Ullman et al. |
| 5,194,300 A | 3/1993 | Cheung |
| 5,198,543 A | 3/1993 | Blanco et al. |
| 5,202,231 A | 4/1993 | Drmanac et al. |
| 5,216,141 A | 6/1993 | Benner |
| 5,235,033 A | 8/1993 | Summerton et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt et al. |
| 5,270,163 A | 12/1993 | Gold et al. |
| 5,298,741 A | 3/1994 | Walt et al. |
| 5,302,509 A | 4/1994 | Cheeseman |
| 5,320,814 A | 6/1994 | Walt et al. |
| 5,357,590 A | 10/1994 | Auracher |
| 5,359,100 A | 10/1994 | Urdea et al. |
| 5,380,489 A | 1/1995 | Sutton et al. |
| 5,386,023 A | 1/1995 | Sanghvi et al. |
| 5,399,491 A | 3/1995 | Kacian et al. |
| 5,403,708 A | 4/1995 | Brennan et al. |
| 5,403,711 A | 4/1995 | Walder et al. |
| 5,409,818 A | 4/1995 | Davey et al. |
| 5,426,180 A | 6/1995 | Kool |
| 5,427,930 A | 6/1995 | Birkenmeyer et al. |
| 5,435,724 A | 7/1995 | Goodman et al. |
| 5,455,166 A | 10/1995 | Walker |
| 5,474,895 A | 12/1995 | Ishii et al. |
| 5,475,096 A | 12/1995 | Gold et al. |
| 5,481,629 A | 1/1996 | Tabuchi |
| 5,489,507 A | 2/1996 | Chehab |
| 5,494,798 A | 2/1996 | Gerdt et al. |
| 5,494,810 A | 2/1996 | Barany et al. |
| 5,496,997 A | 3/1996 | Pope |
| 5,498,523 A | 3/1996 | Tabor et al. |
| 5,503,980 A | 4/1996 | Cantor |
| 5,505,928 A | 4/1996 | Alivisatos et al. |
| 5,512,490 A | 4/1996 | Walt et al. |
| 5,516,635 A | 5/1996 | Ekins et al. |
| 5,518,883 A | 5/1996 | Soini |
| 5,521,065 A | 5/1996 | Whiteley et al. |
| 5,525,464 A | 6/1996 | Drmanac et al. |
| 5,534,424 A | 7/1996 | Uhlen |
| 5,537,000 A | 7/1996 | Alivisatos et al. |
| 5,541,311 A | 7/1996 | Dahlberg et al. |
| 5,545,730 A | 8/1996 | Urdea et al. |
| 5,547,839 A | 8/1996 | Dower et al. |
| 5,554,516 A | 9/1996 | Kacian et al. |
| 5,565,324 A | 10/1996 | Still et al. |
| 5,567,588 A | 10/1996 | Gold et al. |
| 5,571,639 A | 11/1996 | Hubbell et al. |
| 5,571,670 A | 11/1996 | Urdea et al. |
| 5,573,907 A | 11/1996 | Carrino et al. |
| 5,573,909 A | 11/1996 | Singer et al. |
| 5,575,849 A | 11/1996 | Honda et al. |
| 5,580,731 A | 12/1996 | Chang et al. |
| 5,591,584 A | 1/1997 | Chang et al. |
| 5,593,840 A | 1/1997 | Bhatnagar et al. |
| 5,594,117 A | 1/1997 | Urdea et al. |
| 5,594,118 A | 1/1997 | Urdea et al. |
| 5,595,877 A | 1/1997 | Gold et al. |
| 5,595,890 A | 1/1997 | Newton et al. |
| 5,597,909 A | 1/1997 | Urdea et al. |
| 5,602,240 A | 2/1997 | Mesmaeker et al. |
| 5,604,097 A | 2/1997 | Brenner |
| 5,610,287 A | 3/1997 | Nikiforov et al. |
| 5,614,402 A | 3/1997 | Dahlberg et al. |
| 5,616,464 A | 4/1997 | Albagli |
| 5,624,802 A | 4/1997 | Urdea et al. |
| 5,633,972 A | 5/1997 | Walt et al. |
| 5,635,352 A | 6/1997 | Urdea et al. |
| 5,637,459 A | 6/1997 | Burke et al. |
| 5,637,684 A | 6/1997 | Cook et al. |
| 5,639,603 A | 6/1997 | Dower et al. |
| 5,644,048 A | 7/1997 | Yau |
| 5,648,245 A | 7/1997 | Fire et al. |
| 5,656,241 A | 8/1997 | Seifert et al. |
| 5,660,988 A | 8/1997 | Duck et al. |
| 5,679,524 A | 10/1997 | Nikiforov et al. |
| 5,681,697 A | 10/1997 | Urdea et al. |
| 5,681,702 A | 10/1997 | Collins et al. |
| 5,683,867 A | 11/1997 | Biesecker et al. |
| 5,690,894 A | 11/1997 | Pinkel et al. |
| 5,695,940 A | 12/1997 | Drmanac et al. |
| 5,705,337 A | 1/1998 | Gold et al. |
| 5,705,365 A | 1/1998 | Ryder et al. |
| 5,710,029 A | 1/1998 | Ryder et al. |
| 5,719,028 A | 2/1998 | Dahlberg et al. |
| 5,751,018 A | 5/1998 | Alivisatos et al. |
| 5,763,175 A | 6/1998 | Brenner |
| 5,767,259 A | 6/1998 | Albagli |
| 5,773,257 A | 6/1998 | Nielson |
| 5,780,231 A | 7/1998 | Brenner |
| 5,792,607 A | 8/1998 | Backman et al. |
| 5,795,714 A | 8/1998 | Cantor et al. |
| 5,795,716 A | 8/1998 | Chee et al. |
| 5,795,782 A | 8/1998 | Church et al. |
| 5,804,376 A | 9/1998 | Braxton et al. |
| 5,807,522 A | 9/1998 | Brown et al. |
| 5,814,524 A | 9/1998 | Walt et al. |
| 5,830,711 A | 11/1998 | Barany et al. |
| 5,840,256 A | 11/1998 | Demers et al. |
| 5,843,669 A | 12/1998 | Kaiser |
| 5,843,767 A | 12/1998 | Beattie |
| 5,846,710 A | 12/1998 | Bajaj |
| 5,846,717 A | 12/1998 | Brow et al. |
| 5,846,719 A | 12/1998 | Brenner |
| 5,849,215 A | 12/1998 | Gin et al. |
| 5,849,544 A | 12/1998 | Harris |
| 5,853,989 A | 12/1998 | Jeffreys et al. |
| 5,854,033 A | 12/1998 | Lizardi |
| 5,854,684 A | 12/1998 | Stabile et al. |
| 5,856,083 A | 1/1999 | Chelsky et al. |
| 5,858,732 A | 1/1999 | Solomon et al. |
| 5,863,708 A | 1/1999 | Zanzucchi et al. |
| 5,866,321 A | 2/1999 | Matsue et al. |
| 5,866,337 A | 2/1999 | Schon |
| 5,869,252 A | 2/1999 | Bouma et al. |
| 5,871,921 A | 2/1999 | Landegren et al. |
| 5,876,924 A | 3/1999 | Zhang et al. |
| 5,881,200 A | 3/1999 | Burt |
| 5,888,723 A | 3/1999 | Sutton et al. |
| 5,888,779 A | 3/1999 | Kacian et al. |
| 5,888,819 A | 3/1999 | Goelet et al. |
| 5,888,885 A | 3/1999 | Xie |

| | | | | | | |
|---|---|---|---|---|---|---|
| 5,900,481 | A | 5/1999 | Lough et al. | 6,627,402 B2 | 9/2003 | Wallace |
| 5,902,723 | A | 5/1999 | Dower et al. | 6,646,243 B2 | 11/2003 | Pirrung et al. |
| 5,935,793 | A | 8/1999 | Wong et al. | 6,650,411 B2 | 11/2003 | Odoy et al. |
| 5,942,391 | A | 8/1999 | Zhang et al. | 6,686,150 B1 | 2/2004 | Blackburn et al. |
| 5,952,174 | A | 9/1999 | Nikiforov et al. | 6,812,005 B2 | 11/2004 | Fan et al. |
| 5,952,176 | A | 9/1999 | McCarthy et al. | 6,828,100 B1 | 12/2004 | Ronaghi |
| 5,976,797 | A | 11/1999 | Mitsuhashi | 6,858,412 B2 | 2/2005 | Willis et al. |
| 5,981,176 | A | 11/1999 | Wallace | 6,913,884 B2 * | 7/2005 | Stuelpnagel et al. ............. 435/6 |
| 5,998,175 | A | 12/1999 | Akhavan-Tafti | 7,582,420 B2 * | 9/2009 | Oliphant et al. ................. 435/6 |
| 6,001,564 | A | 12/1999 | Bergeron et al. | 8,288,103 B2 * | 10/2012 | Oliphant et al. ............. 435/6.12 |
| 6,005,093 | A | 12/1999 | Wood et al. | 2001/0029049 A1 | 10/2001 | Walt et al. |
| 6,013,456 | A | 1/2000 | Akhavan-Tafti | 2001/0055801 A1 | 12/2001 | Chen et al. |
| 6,017,738 | A | 1/2000 | Morris et al. | 2002/0001801 A1 | 1/2002 | Fan et al. |
| 6,023,540 | A | 2/2000 | Walt et al. | 2002/0006617 A1 | 1/2002 | Fan et al. |
| 6,027,889 | A | 2/2000 | Barany et al. | 2002/0051971 A1 | 5/2002 | Stuelpnagel et al. |
| 6,045,996 | A | 4/2000 | Cronin et al. | 2002/0102578 A1 | 8/2002 | Dickinson |
| 6,051,380 | A | 4/2000 | Sosnowski et al. | 2002/0132221 A1 | 9/2002 | Chee et al. |
| 6,054,564 | A | 4/2000 | Barany et al. | 2002/0150909 A1 | 10/2002 | Stuelpnagel |
| 6,060,245 | A | 5/2000 | Sorge | 2002/0150921 A1 | 10/2002 | Barany et al. |
| 6,063,573 | A | 5/2000 | Kayyem | 2002/0168645 A1 | 11/2002 | Taylor |
| 6,066,454 | A | 5/2000 | Lipshutz et al. | 2003/0036064 A1 | 2/2003 | Stuelpnagel et al. |
| 6,083,763 | A | 7/2000 | Balch | 2003/0108867 A1 | 6/2003 | Chee |
| 6,096,496 | A | 8/2000 | Frankel et al. | 2003/0108900 A1 | 6/2003 | Oliphant |
| 6,110,678 | A | 8/2000 | Weisburg et al. | 2003/0157499 A1 | 8/2003 | Lundeberg et al. |
| 6,124,102 | A | 9/2000 | Fodor et al. | 2003/0162217 A1 | 8/2003 | Rothberg et al. |
| 6,143,495 | A | 11/2000 | Lizardi et al. | 2003/0170684 A1 | 9/2003 | Fan |
| 6,172,218 | B1 | 1/2001 | Brenner | 2003/0207295 A1 | 11/2003 | Gunderson et al. |
| 6,183,960 | B1 | 2/2001 | Lizardi | 2003/0211489 A1 | 11/2003 | Shen |
| 6,187,575 | B1 | 2/2001 | Sobek et al. | 2004/0101835 A1 | 5/2004 | Willis et al. |
| 6,200,737 | B1 | 3/2001 | Walt et al. | 2004/0137473 A1 | 7/2004 | Wigler et al. |
| 6,210,884 | B1 | 4/2001 | Lizardi | | | |
| 6,210,891 | B1 | 4/2001 | Nyren et al. | FOREIGN PATENT DOCUMENTS | | |
| 6,210,910 | B1 | 4/2001 | Walt et al. | EP | 0 269 764 | 6/1988 |
| 6,221,603 | B1 | 4/2001 | Mahtani | EP | 0 317 074 | 5/1989 |
| 6,225,064 | B1 | 5/2001 | Uematsu et al. | EP | 0 336 731 | 10/1989 |
| 6,235,472 | B1 | 5/2001 | Landegren et al. | EP | 0 371 437 | 6/1990 |
| 6,251,639 | B1 | 6/2001 | Kurn | EP | 0 392 546 | 10/1990 |
| 6,258,568 | B1 | 7/2001 | Nyren | EP | 0 439 182 | 7/1991 |
| 6,268,148 | B1 | 7/2001 | Barany et al. | EP | 0 478 319 | 4/1992 |
| 6,274,320 | B1 | 8/2001 | Rothberg et al. | EP | 0 320 308 | 11/1993 |
| 6,277,578 | B1 | 8/2001 | Shultz | EP | 0 614 987 | 9/1994 |
| 6,280,935 | B1 | 8/2001 | Macevicz | EP | 0 723 146 | 7/1996 |
| 6,280,949 | B1 | 8/2001 | Lizardi | EP | 0 776 970 | 4/1997 |
| 6,284,385 | B1 | 9/2001 | Guillaumon et al. | EP | 0 799 897 | 11/1998 |
| 6,284,465 | B1 | 9/2001 | Wolber | EP | 0 862 656 | 7/2001 |
| 6,284,497 | B1 | 9/2001 | Sabanayagam et al. | EP | 1 121 465 | 9/2002 |
| 6,287,768 | B1 | 9/2001 | Chenchik | EP | 1196630 | 11/2008 |
| 6,287,776 | B1 | 9/2001 | Hefti | GB | 2 332 516 | 6/1999 |
| 6,288,220 | B1 | 9/2001 | Kambara et al. | WO | WO 86/03782 | 7/1986 |
| 6,291,166 | B1 | 9/2001 | Gerdes et al. | WO | WO 89/09835 | 10/1989 |
| 6,291,193 | B1 | 9/2001 | Khodadoust | WO | WO 89/11101 | 11/1989 |
| 6,297,006 | B1 | 10/2001 | Drmanac | WO | WO 89/12696 | 12/1989 |
| 6,306,643 | B1 | 10/2001 | Gentalen et al. | WO | WO 90/01069 | 2/1990 |
| 6,316,229 | B1 | 11/2001 | Lizardi et al. | WO | WO 90/01564 | 2/1990 |
| 6,327,410 | B1 | 12/2001 | Walt et al. | WO | WO 91/06678 | 5/1991 |
| 6,329,150 | B1 | 12/2001 | Lizardi | WO | WO 91/13075 | 9/1991 |
| 6,335,165 | B1 | 1/2002 | Navot et al. | WO | WO 92/15712 | 9/1992 |
| 6,339,147 | B1 | 1/2002 | Lukhtanov et al. | WO | WO 93/02360 | 2/1993 |
| 6,344,329 | B1 | 2/2002 | Lizardi | WO | WO 93/21340 | 10/1993 |
| 6,355,431 | B1 | 3/2002 | Chee et al. | WO | WO 93/23564 | 11/1993 |
| 6,372,813 | B1 | 4/2002 | Johnson et al. | WO | WO 93/25563 | 12/1993 |
| 6,399,365 | B2 | 6/2002 | Besemer et al. | WO | WO 94/02515 | 2/1994 |
| 6,416,952 | B1 | 7/2002 | Pirrung et al. | WO | WO 95/00666 | 1/1995 |
| 6,429,027 | B1 | 8/2002 | Chee et al. | WO | WO 95/00667 | 1/1995 |
| 6,482,593 | B2 | 11/2002 | Walt et al. | WO | WO 95/05480 | 2/1995 |
| 6,491,871 | B1 | 12/2002 | Fodor et al. | WO | WO95/14106 | 5/1995 |
| 6,506,594 | B1 | 1/2003 | Barany et al. | WO | WO 95/14106 | 5/1995 |
| 6,511,810 | B2 | 1/2003 | Bi et al. | WO | WO 95/16918 | 6/1995 |
| 6,524,793 | B1 | 2/2003 | Chandler et al. | WO | WO 95/21271 | 8/1995 |
| 6,534,293 | B1 | 3/2003 | Barany et al. | WO | WO 95/25538 | 9/1995 |
| 6,544,732 | B1 | 4/2003 | Chee et al. | WO | WO 96/03212 | 2/1996 |
| 6,544,739 | B1 | 4/2003 | Fodor et al. | WO | WO 96/12014 | 4/1996 |
| 6,558,928 | B1 | 5/2003 | Landegren | WO | WO 96/15271 | 5/1996 |
| 6,573,051 | B2 | 6/2003 | Alsmadi et al. | WO | WO 96/17958 | 6/1996 |
| 6,576,424 | B2 | 6/2003 | Fodor et al. | WO | WO 96/30392 | 10/1996 |
| 6,597,000 | B2 | 7/2003 | Stern | WO | WO 96/31622 | 10/1996 |
| 6,600,031 | B1 | 7/2003 | Fodor et al. | WO | WO 97/14028 | 4/1997 |
| 6,610,482 | B1 | 8/2003 | Fodor et al. | WO | WO 97/31256 | 8/1997 |
| 6,618,679 | B2 | 9/2003 | Loehrlein et al. | WO | WO 97/40385 | 10/1997 |

| | | |
|---|---|---|
| WO | WO 97/45559 | 12/1997 |
| WO | WO 97/46704 | 12/1997 |
| WO | WO 98/00667 | 1/1998 |
| WO | WO 98/04746 | 2/1998 |
| WO | WO 98/13523 | 4/1998 |
| WO | WO 98/28440 | 7/1998 |
| WO | WO 98/31836 | 7/1998 |
| WO | WO 98/37230 | 8/1998 |
| WO | WO 98/40726 | 9/1998 |
| WO | WO 98/50782 | 11/1998 |
| WO | WO 98/53093 | 11/1998 |
| WO | WO 98/53300 | 11/1998 |
| WO | WO 98/59066 | 12/1998 |
| WO | WO 98/59243 | 12/1998 |
| WO | WO 99/18434 | 4/1999 |
| WO | WO 99/39001 | 8/1999 |
| WO | WO 99/45357 | 9/1999 |
| WO | WO 99/53102 | 10/1999 |
| WO | WO 99/60170 | 11/1999 |
| WO | WO 99/64867 | 12/1999 |
| WO | WO 99/67414 | 12/1999 |
| WO | WO 99/67641 | 12/1999 |
| WO | WO 00/04193 | 1/2000 |
| WO | WO 00/04372 | 1/2000 |
| WO | WO 00/09738 | 2/2000 |
| WO | WO 00/13004 | 3/2000 |
| WO | WO 00/16101 | 3/2000 |
| WO | WO 00/39587 | 7/2000 |
| WO | WO 00/47996 | 8/2000 |
| WO | WO 00/48000 | 8/2000 |
| WO | WO00/50172 | 8/2000 |
| WO | WO 00/52479 | 9/2000 |
| WO | WO 00/55369 | 9/2000 |
| WO | WO 00/56934 | 9/2000 |
| WO | WO 00/58516 | 10/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/06012 | 1/2001 |
| WO | WO 01/14589 | 3/2001 |
| WO | WO 01/20035 | 3/2001 |
| WO | WO01/20039 | 3/2001 |
| WO | WO 02/10431 | 2/2002 |
| WO | WO 02/12897 | 2/2002 |
| WO | WO 02/057491 | 7/2002 |
| WO | WO 02/061143 | 8/2002 |
| WO | WO 03/006677 | 1/2003 |

OTHER PUBLICATIONS

U.S. Appl. No. 60/160,927, filed Oct. 22, 1999, Chee.
BioArray Solutions Ltd., Notice of Opposition to a European Patent, Aug. 3, 2009.
EPR of WO 00/50172 Extract from Register of European Patents in respect of WO 00/50172 (Extract from the Register of European Patents EP1163052) dated Jul. 23, 2009.
EPR of WO 01/20039 European Patent Register of WO 01/20039 (Auszug aus dem Europäischen Patentregister) dated May 25, 2009.
Roche Diagnostics GmBH, Notice of Opposition, Jul. 30, 2009.
United States Patent Application No. 09/513,362, Board of Appeals Decision published Sep. 21, 2009.
"Interlocutory Decision in Opposition Proceedings (Art. 101(3)(a) and 106(2)EPC), EP 1 196 630, Apr. 4, 2011", EP Serial No. 00926204.9, Apr. 4, 2011, 25 pages.
"Statement of Grounds of Appeal", EP Application No. EP1196630, Jul. 26, 2011, 11 pages.
"Response to Grounds of Appeal", EP1196630 and Appeal No. T1252/11 against a Decision of the Opposition, Apr. 4, 2011, 15 pages.
U.S. Appl. No. 09/473,904, filed Dec. 28, 1999, Illumina.
U.S. Appl. No. 09/553,993, filed Apr. 20, 2000, Illumina.
U.S. Appl. No. 09/556,463, filed Apr. 21, 2000, Illumina.
U.S. Appl. No. 10/264,571, filed Oct. 4, 2002, Gunderson et al.
U.S. Appl. No. 10/264,574, filed Oct. 4, 2002, Gunderson et al.
U.S. Appl. No. 10/272,384, filed Oct. 15, 2002, Gunderson et al.

Abel, "Fiber-Optic Evanescent Wave Biosensor for the Detection of Oligonucleotides", *Analytical Chemistry*, 68:2905-2912 (1996).
Abramson, et al., "Nucleic acid amplification technologies", *Current Opinion in Biotechnology*, 4:41-47 (1993).
Ahmadian, et al., "Analysis of the p53 tumor suppressor gene by pyrosequencing," *Biotechniques* 28(1):140-4, 146-7 (2000).
Altshul, et al., "Basic Local Alignment Search Tool", *J. Mol. Biol.* 215:403-410 (1990).
Angel, et al., "Optrodes: Chemically Selective Fiber-Optic Sensors", *Spectroscopy*, 2(4):38-47 (19987).
Anonymous, *Pierce Chemical Company Catalog*, (1994 ).
Anonymous, "Fluorescent Microspheres", *Tech. Note 19, BangsLaboratories*, (Fishers, In) Feb. 1997.
Anonymous, "Gene Characterization Kits", *p39, Stratagene Catalog* (1988).
Anonymous, "Microsphere Detection Guide", *Bang Laboratories*, (Fisher, In) (Sep. 1998).
Anonymous, "PCR Essential Data", *J.W. Wiley & Sons. Ed. C.R. Newton*. (1995).
Anonymous, "Profiting from Gene-based Diagnostics", *CTB International Publishing Inc., New Jersey, USA* (1996).
Anslyn, et al., "Unifying the Current Data on the Mechanism of Cleavage-Transesterification of RNA", *Angew. Chem. Int. Ed. Engl.*, 36 432-450 (1997).
Antson, et al., "PCR-generated padlock probes detect single nucleotide variation in genomic DNA", *Nucleic Acids Research*, 28(12):e58(i)-(vi) (2000).
Ausubel, et al., "Short Protocols in Molecular Biology", *Second Edition*, (1992).
Baner, "Signal amplification of padlock probes by rolling circle replication", *Nucleic Acids Research*, 26(22):5073-5078 (1998).
Bangs, L. B., "Immunological Applications of Microspheres", *The Latex Course, Bangs Laboratories* (Carmel, In) Apr. 1996.
Barany, "Genetic disease detection and DNA amplification using cloned thermostable ligase", *Proceedings of the National Academy of Sciences USA*, 88:189-193 (1991).
Barbier, et al., "Conformation-Controlled Hydrolysis of Polyribonucleotides by Sequential Base Polypeptides", *J. Am. Chem. Soc.*, 114:3511-3515 (1992).
Barnard, "A Fibre-Optic Chemical Sensor with Discrete Sensing Sites", *Nature*, 353:338-340 (1991).
Barnard, "Fiber-Optic Organic Vapor Sensor", *Environ. Sci. Technol.*, 25(7):1301-1304 (1991).
Barshop, et al., "Luminescent immobilized enzyme test systems for inorganic pyrophosphate:assays using firefly luciferase and nicotinamide-mononucleotide adenylyl transferase or adenosine-5'-triphosphate sulfurylase", *Anal. Biochem.* 197(1):266-272 (1991).
Bashkin, et al., "Sequence-Specific Cleavage of HIV mRNA by a Ribozyme Mimic", *J.Am. Chem. Soc.*, 116(13):5981-5982 (1994).
Bashkin, et al., "Synthesis and Characterization of Nucleoside Peptides: Toward Chemical Ribonucleases", *J. Org. Chem.*, 55:5125-5132 (1990).
Bawendi, et al., "The Quantum Mechanics of Larger Semiconductor Clustors 'Quantum Dots'", *Annu. Rev. Phys. Chem.*, 41:477-496 (1990).
Beaucage, et al., "Deoxynucleoside phosphoramidites—A new class of key intermediates for deoxypolynucleotide synthesis", *Tetrahedron Letters*, 22(20):1859-1862 (1981).
Beaucage, S. L. et al., "The synthesis of specific ribonucleotides and unrelated phosphorylated biomolecules by the phophoramidite method", *Tetrahedron*, 49(46):10441-10488 (1993).
Belmont, et al., "Efficient and versatile chemical tools for cleavage of abasic sites in DNA", *New J. Chem.*, 21:47-54 (1997).
Berg, et al., "Hybrid PCR Sequencing: Sequencing of PCR products using a univesal primer", *BioTechniques*, 17(5):896-901 (1994).
Bock, L. C. et al., "Selection of single-stranded DNA molecules that bind and inhibit human thrombin", *Nature*, 355:564-566 (1992).
Boguszewski, Cesar L. et al., "Cloning of Two Novel Growth Hormone Transcripts Expressed in Human Placenta", *J Clin Endocrinology and Metabolism*, 83(8):2878-2885 (1998).
Bornet, O et al., "Solution structure of oligonucleotides covalently linked to a psoralen derivative", *Nucleic Acids Res.*, 23(5):788-795 (1995).

Breslow, R et al., "Ribonuclease mimics", *Tetrahedron*, 47:2365-2376 (1991).
Brill, et al., "Synthesis of Oligodeoxynucleoside Phosphorodithioates via Thioamidites.", *J. Am. Chem. Soc.* 111:2321-2322 (1989).
Broude, et al., "Enhanced DNA sequencing by hybridization", *PNAS*, 91:3072-3076 (1994).
Butte, "The Use and Analysis of Microarray Data", *Nature Reviews Drug Discovery*, 1:951-960 (2002).
Canard B. and, Sarfati R.S , "DNA polymerase fluorescent substrates with reversible 3'-tags", *Gene*, 148:1-6 (1994).
Carlsson, et al., "Screening for Genetic Mutation", *Nature*, 380:207 (1996).
Chan, et al., "Quantum Dot Bioconjugates for Ultrasensitive Nonisotopic Detection", *Science.*, 281:2016-2018 (1998).
Chase, et al., "Single-stranded DNA binding proteins required for DNA replication", *Ann. Rev. Biochem.*, 55:103-36 (1986).
Chatterjee, et al., "Cloning and overexpression of the gene encoding bacteriophage T5 DNA polymerase", *Gene*, 97:13-19 (1991).
Chee, M et al., "Enzymatic multiplex DNA sequencing", *Nucl. Acid Res.*, 19(12):3301-3305 (1991).
Chen, "A Microsphere-Based Assy for Multiplexed Single Nucleotide Polymorphism Analysis Using Single Base Chain Extension", *Genome Research*, 10(4):549-557 (2000).
Chow, et al., "A structural Basis for RNA-Ligand interactions", *Chem. Rev.*, 97:1489-1513 (1997).
Chow, C. S. et al., "Recognition of G-U Mismatches by tris(4,7-diphenyl-1,10-phenanthroline) rhodium(III)", *Biochemistry*, 31(24):5423-5429 (1992).
Coleman, et al., "Physical chemical studies of the structure and function of DNA binding (helix-destabilizing) proteins", *CRC Critical Reviews in Biochemistry*, 7(3):247-289 (1980).
Conner, et al., "Detection of sickle cell $\alpha^s$-globin allele by hybridization with synthetic oligonucleotides," *PNAS*, 80:272-282 (1983).
Cook, et al., "A rapid Enzymatic Assay for Measurement of Inorganic Pyrophosphate in Animal Tissues", *Anal. Biochem.* 91:557 (1978).
Corder, E H. , "Gene dose of apolipoportein E type 4 allele and the risk of Alzheimer's disease in late onset families", *Science*, 261:921-923 (1993).
Corriu, et al., "Recent Developments of Molecular Chemistry for Sol-Gel Processes", *Angew. Chem. Int. Ed. Engel.* 35:1420-1436 (1996).
Cunin, "Biomolecular screening with encoded porous-silicon photonic crystals", *Nature Materials*, 1:39-41 (2002).
Czarnik, "Illuminating the SNP Genomic Code", *Modern Drug Discovery*, vol. 1(2) 1998 , 49-55.
Dempcy, et al., "Synthesis of Thymidyl Pentamer of Deoxyribonucleic Guanidine and Binding Studies with DNA Homopolynucleotides.", *Proc. Natl. Acad. Sci.* 92:6097-6101 (1995).
Dickinson, et al., "Generating Sensor Diversity Through Combinatorial Polymer Synthesis", *Analytical Chemistry*, 69(17):97-107 (1997).
Dorey, E, "Sequenom Steps Toward Drug Development", 19(7):600-601 (2001).
Doyle, "High Temperature Sample Holder for Fast Atom Bombardment Mass Spectrometry of Molten Materials", *Anal. Chem.* 59:537-539 (1987).
Drake, H. L. et al., "A new, convenient method for the rapid analysis of inorganic pyrophosphate", *Anal. Biochem.* 94:117 (1979).
Drmanac, et al., "Prospects for a Minaturized, Simplified and Frugal Human Genome Project", *Scientia Yugoslavica* 16(1-2):97-107 (1990).
Drmanac, "Sequencing by Hybridization", *Automated DNA Sequencing and Analysis, ed. M.* 1994.
Drmanac, et al., "Sequencing by Hybridization (SBH) with Oligonucleotide Probes as an Integral Approach for the Analysis of Complex Genomes", *Inter. J. of Genome Research* 1(1):597-79 (1992).
Drmanac, et al., "Sequencing by Oligonucleotide Hybridization: A Promising Framework in Decoding of the Genome Project", *The First International Conf. of Electrophoresis.Florida State Univ.* pp. 10-13 (1990).
Drmanac, R et al., "Sequencing of megabase plus DNA by hybridization: theory and method", *Genomics*, 4:114-128 (1989).
Dvatkina N.B., and, Arzumanov A.A. , "Terminating substrates of DNA polymerases: synthesis and functional study", *Nucleic Acid Symp Ser.*, 18:117-121 (1987).
Eckstein, "Oligonucleotides and Analogues: A Practical Approach", *Oxford University Press Egholm, J. Am. Chem. Soc*, 114:1985 (1992).
Egholm, M , "Peptide nucleic acids (PNA). Oligonucleotide analogs with an achiral peptide backbone", *J.Am. Chem. Soc.*, 14:1895-1897 (1992).
Egholm, et al., "PNA Hybridizes to Complementary Oligonucleotides Obeying the Watson-Crick Hydrogen-Bonding Rules.", *Nature*, 365:566-568 (1993).
Eigen, M. and, Rigler, R. , "Sorting single molecules: application to diagnostics and evolutionary biotechnology", *Proc. Natl. Acad.Sci.* 91(13):5740-5747 (1994).
Endo, et al., "Molecular Design for a Pinpoint RNA Scission Interposition of Oligoamined between two DNA oligomers", *J. Org. Chem.* 62:846-852 (1997).
Famulok, et al., "Oligonucleotide libraries-variatio delectat", *Current Op. Chem Biol.*, 2:320-327 (1998).
Ferguson, J A. et al., "A Fiber-Optic DNA Biosensor Microarray for the Analysis of Gene Expression", *Nature Biotechnol.* 14:1681-1684 (1996).
Fodor, "Light-Directed, Spatially Addressable Parallel Chemical Synthesis", *Science*, 251:767-773 (1991).
Fredman, et al., "HGVbase: a human sequence variation database emphasizing data quality and a broad spectrum of data sources", *Nucleic Acid Research*, 30(1):387-391 (2002).
Freeman, et al., "Oxygen Probe Based on Tetrakis(alkylamino)ethylene Chemilluminescence", *Analytical Chemistry*, 53(1):98102 (1981).
Freund and, Walpole , "Mathematical Statistics", Third Edition, Prentice Hall, USA (1980).
Fuh, "Single Fibre Optic Fluorescense pH Probe", *Analyst*, 112:1159-1163 (1987).
Gillespie, R. J. , "A novel thermal rearrangement of the 2-thiabicyclo [3,1,0]hex-3-ene system. The crystal and molecular structure of ethyl-2,4- dichloro-5-hydroxy-6-methylbenzoate", *Tetrahedron*, 37:743-746 (1996).
Guillory, R J. et al., "Measurement of simultaneous synthesis of inorganic pyrophosphate and adenosine triphosphate", *Anal. Biochem.* 39:170-180 (1971).
Gunderson, "Mutation Detection by Ligation to Complete n-mer DNA Arrays", *Genome Research*, 8:1142-1153 (1998).
Guo, Zhen et al., "Direct fluorescence analysis of genetic polymorphisms by hybridization with oligonucleotide arrays on glass supports", *Nucleic Acids Research*, 22(24):5456-5465 (1994).
Hall, et al., "Efficient sequence-specific cleavage of RNA using novel europium complexes conjugated to oligonucleotides", *Chemistry & Biology*, 1:185-190 (1994).
Hall, J. et al., "Towards artificial ribonucleases: the sequence-specific cleavage of RNA in a duplex", *Nucleic Acids Research* 24(18):3522-3526 (1996).
Hardenbol, et al., "Multiplexed genotyping with sequence-tagged molecular inversion probes", *Nature Biotechnology*, 21(6):673-678 (2003).
Hatch, et al., "Rolling circel amplification of DNA immovilized on solid surfaces and its application to multiplex mutation detection", *Genetic Analysis: Biomolecular Engineering*, 15:35-40 (1999).
Haugland, "Molecular Probes Handbook", 6th Edition, Eugene, OR, USA.
Healey, "Development of a Penicillin Biosensor Using a Single Optical Imaging Fiber", *SPIE Proc.*, 2388:568-573 (1995).
Healey, B. G. et al., "Fiber Optic DNA Sensory Array Capable of Detecting Point Mutations", *Analytical Biochemistry*, 251(2):270-279 (1997).
Healey, "Improved Fiber-Optic Chemical Sensor for Penicillin", *Analytical Chemistry*, 67(24):4471-4476 (1995).
Hendry, et al., "Metal Ion Promoted Reactions of Phosphate Derivatives", *Prg. Inorg. Chem. Bioinorganic Chem.*, 1990, pp. 201-258, vol. 13. 1990 , 201-258.

Hirschfeld, "Laser-Fiber-Optic "Optrode" for Real Time In Vivo Blood Carbon Dioxide Level Monitoring", *Journal of Lightwave Technology*, LT-5(7):1027-1033 (1987).
Holloway, et al., "Tools for Molecular Genetic Epidemiology: A comparison of MADGE Methodology with Other Systems", *Biotechnol Genet Eng Rev*, 17:71-88 (2000).
Horn, T et al., "Oligonucleotides with Alternating Anionic and Cationic Phosphoramidate Linkages: Synthesis and Hybridization of Stereo-uniform Isomers," *Tetrahedron Lett.* 37(6):743-746 (1996).
Hsuih, "Novel, ligation-dependent PCR assay for detection of Hepatitis C Virus in Serum", *J. of Clinical Microbiology*, 34(3):501-507 (1996).
Hyman, E D., "A new method of sequencing DNA", *Anal. Biochem*, 174:423-436 (1988).
Iannone, "Multiplexed Single Nucleotide Polymorphism Genotyping by Oligonucleotide Ligation and Flow Cytometry", *Cytometry*, 39(2)131-140 (2000).
Jeffs, et al., "Unusual Conformation of a 3'-thioformacetal linkage in a DNA duplex", *J. Biomolecular NMR*, 34:17 (1994).
Jenkins, G N. et al., "The Biosynthesis of Carbocyclic Nucleosides.", *Chem.Soc. Rev.* 1995, 169-176.
Johnson, et al., "An Enzymatic method for determination of inorganic pyrophosphate and its use as an assay for RNA polymerase", *Anal. Biochem.* 26:137 (1968).
Johnson, K. A. et al., "Continuous assay for DNA polymerization by light scattering", *Anal. Biochem.*, 136:192-194 (1984).
Jones, D H., "A iterative and regenerative method for DNA sequencing", *Biotechniques*. 22:939 (1997).
Jung, et al., "Bacteriophage PRD1 DNA polymerase: evolution of DNA polymerases", *Proc. Natl Acad. Sci. USA* 84:8287 (1987).
Justesen, et al., "Spectrophotometric Pyrophosphate Assay of 2', 5'-Oligoadenylate Synthetase", *Anal. Biochem.* 207 (1):90-93 (1992). 1992, 90-93.
Karamohamed and Nyren, et al., "Real-Time detection and quantification of adenosine triphosphate sulfurylase activity by a bioluminometric approach", *Anal. Biochem.* 271:81-85 (1999).
Keck, M. V., "Sequence-Specific Hydrolysis of Yeast tRNAPhe Mediated by Metal—Free Bleomycin", *Biochemistry*, 34(37):12029-12037 (1995).
Khanna, et al., "Mutiplex PCR/LDR for detection of K-ras mutations in primary colon tumors", *Oncogens*, 18:27-38 (1999).
Khrapko, et al., "Hybridization of DNA with oligonucleotides immobilized in a gel: a convenient method for recording single base replacements," *Mol. Biol.*, 25:718-730 (1991).
Kirk, et al., "Hydrolysis of an RNA di-nucleoside monophosphate by neomycin B", *Chem. Commun.*, 1998, pp. 147-148. 1998, 147-148.
Komiyama, et al., "Kinetic Analysis of Diamine-Catalyzed RNA Hydrolysis", *J. Org. Chem.*, 62:2155-2160 (1997).
Kong, et al., "Characterization of a DNA polymerase from the hyperthermophile archaea *Termococcus litoralis*", *J. Biol. Chem.* 268:1965-1975 (1993).
Kool, et al., "Circular oligonucleotides: New concepts in oligonucleotide design", *Annul. Rev. Biophys. Biomol. Struct.*, 25:1-28 (1996).
Koster, H et al., "A strategy for rapid and efficient DNA sequencing by mass spectrometry", *Nature Biotechnology*, 14:1123-1128 (1996).
Kozal, "Extensive polymorphisms observed in HIV-1 Glade B protease gene using high-density oligonucleotide arrays", *Nature Med*, 2:753-759 (1996).
Kuppuswamy, et al., "Single Nucleotide primer extension to detect genetic diseases: Experimental application to hemophilia B (Factor IX) and cystic fibrosis genes", *Proc. Natl. Acad. of Sci USA* 88(4):1143-1147 (1991).
Lakowicz, J R., "Principles of Fluorescent Spectroscopy, 2nd Edition.", *Kluwer Academic/Plenum Publisheers: New York, NY* (1999).
Landegren, Ulf, "Detection of Mutations in Human DNA", *GATA*, 9(1):3-8 (1992).
Landegren, et al., "Reading Bits of Genetic Information: Methods for Single-Nucleotide Polymorphism Analysis", *Genome Research*, 8:769-776 (1998).
Letsinger, "Cationic Oligonucleotides", *J.Am. Chem. Soc.*, 110:4470 (1988).

Letsinger, et al., "Effects of pendant groups at phosphorus on binding properties of d-ApA Analogues", *Nucleic Acid Res.*, 14:3487 (1986).
Letsinger, et al., "Hybridization of Alternating Cationic/Anionic Oligonucleotides to RNA Segments", *Nucleoside & Nucleotide*, 13:1597-1605 (1994).
Letsinger, R. L., "Phosphoramidate analogs of oligonucleotides", *J. Org.Chem.*, 35(11):3800-3803 (1970).
Lippitsch, et al., "Fibre-Optic Oxygen Sensor with the Fluorescence Decay Time as the Information Carrier", *Analytical Chemistry Acta*, 205:1-6 (1998).
Liu, et al., "Rolling circle DNA synthesis: Small circular oligonucleotides as efficient templates for DNA polymerases", *J. Am. Chem Soc.*, 118:1587-1594 (1996).
Lizardi, "Mutation detection and single-molecule counting using isothermal rolling-circle amplification", *Nature Genetics*, 19:225-232 (1998).
Lubbers, et al., "Optical Fluorescense Senosrs for Continuous Measurement of Chemical Concentrations if Biological Systems", *Sens. Actuators*, 4:641-654 (1983).
Lust, et al., "A rapid enzymatic assay for measurement of inorganic pyrophsophate in biological samples", *Clin. Chem. Acta* 66(2):241 (1976).
Lyamichev, "Polymorphism identification and quantitative detection of genomic DNA by invasive cleavage of oligonucleotide probes", *Nature Biotechnology*, 17:292-296 (1999).
Mag, et al., "Synthesis of Selective Cleavage of an Oligonucleotide Containing a Bridged Internucleotide 5'-phosphorothioate Linkage", *Nucleic Acids Res.* 19(7):1437-1441 (1991).
Magda, et al., "Metal Complex Conjugates of Antisense DNA which Display Ribozyme-Like Activity", *J. Am. Chem. Soc*, 119:6947-6948 (1997).
Magda, et al., "Site—Specific Hydrolysis of RNA by Europium (III) Texaphyrin Conjugated to a Synthetic Oligodeoxyribonucleotide", *J. Am. Chem. Soc.*, 116:7439-7440 (1994).
Magda, et al., "Synthesis and Kinetic Properties of Ribozyme Analogues Prepared Using Phosphoamidite Derivatives of Dysporsium (III) Texaphyrin", *J. Am. Chem. Soc.*, 119:2293-2294 (1997).
Maniatis, et al., "Molecular Cloning: A Laboratory Manual", 2nd Edition, (1989).
Margulies, Marcel et al., "Genome Sequencing in microfabricated high-density picolitre reactors", *Nature* 437(7057):376-380 (2005).
Margulies, M et al., "Supplemental Material 3", *Nature*, 437:1-34 (2005).
Matsumoto, et al., "Primary structure of bacteriophage M2 DNA Polymerase: conserved segments within protein priming DNA polymerases and DNA polymersase I of *Escherichia coli*", *Gene*, 84:247 (1989).
Meier, et al., "Peptide Nucleic Acids (PNA).-Unusual Properties of Nonionic Oligonucleotide Analogues.", *Angew. Chem. Int. Ed. Engl.* 31(8):1008-1010 (1992).
Mesmaeker, A D. et al., "Comparison of Rigid and Flexible Backbones in Antisense Oligonucleotides", *Bioorganic and Medicinal Chem. Lett.* 4:395-398 (1994).
Metzker, "Termination of DNA syntehsis by novel 3'-modified-deoxyribonucleoside 5'-triphosphases", *Nucleic Acids Research*, 22(20):4259-4267 (1994).
Michael, "Fabrication of Micro- and Nanostructures Using Optical Imaging Fibers and Their Use as Chemical Sensors", *Proc. 3rd Intl Symp, Microstructures and Microfabricated Systems*, pp. 152-157 (1997).
Michael, "Making Sensors out of Disarray: Optical Sensor Microarrays", *Proc. SPIE*, 3270:34-41 (1998).
Michael, "Randomly Ordered Addressable High-Density Optical Sensor Arrays", *Analytical Chemistry*, 70(7):1242-1248 (1998).
Mignani(Grazia), "In-Vivo Biomedical Monitoring by Flber-Optic Systems", *Journal of Lightwave Technology*, 13(7):1396-1406 (1995).
Milanovich, et al., "Clinical Measurements Using Fiber Optics and Optrodes", *Novel Optical Fiber Techniques for Medical Application, SPIE*, 494:1831 (1984).
Mir, et al., "Sequence Variation in Genes and Genomic DNA: Methods for Large-Scale Analysis", *Annu. Rev Genomics Hum. Genet.*, 1:329-360 (2000).

Moucheron, et al., "Photophysics of Ru(phen)(PHEHAT): A Novel 'Light Switch'for DNA and Photo-oxidant for Mononucleotides", *Inorg. Chem.*, 36:584-592 (1997).
Munkholm, et al., "A Fiber-Optic Sensor for CO2 Measurement", *Talanta*, 35(2):109-112 (1988).
Munkholm, C. et al., "Polymer modification of fiber optical imaging fibers", *Analytical Chemistry* 58(7):1427-1430 (1986).
Myer, et al., "Synthesis and application of circularizable ligation probes", *BioTechniques*, 30:584-593 (2001).
Needham-Vandevanter, et al., "Characterization of an Adduct between CC-1065 and a defined oligodeoxynucleotide duplex", *Nucleic Acids Research* 12(15):6159-6168 (1984).
Newton, et al., "Analysis of any point mutation in DNA. The amplification refractory mutation system (ARMS)", *Nucleic Acid Research*, 17:2503-2516 (1989).
Nickerson, "Gene probe assays and their detection", *Current Opinion in Biotechnology*, 4:48-51 (1993).
Nikiforov, et al., "Genetic Bit Analysis: a solid phase method for typing single nucleotide polymorphisms", *Nucleic Acids Research*, 22(20):4167-4175 (1994).
Nilsen, T. W. , "Syntehsis and Application of Circularizable Ligation Probes", *Biotechniques*, 30:584-593 (2001).
Nilsson, et al., "Padlock probes reveal single-nucleotide differences, parent of origin and in situ distribution of centromeric sequencies in human chromosmes 13 and 21", *Nature Genetics*, 16:252-255 (1997).
Nilsson, et al., "Padlock probes: circularizing oligonucleotides for localized DNA detection", *Science*, 265:2085-2088 (1994).
Nyren, "Apyrase Immobilized on Paramagnetic Beads Used to Improve Detection Limits in Bioluminometric ATP monitoring", *J. Biolumin Chemilumin.* 9(1):29-34 (1994).
Nyren, et al., "Detection of Single-Base Changes Using a Bioluminometric Primer Extension Assay", *Anal. Biochem.* 244(2):367-373 (1997).
Nyren, P. et al., "Enzymatic method for continuous monitoring of inorganic pyrophosphate synthesis", *Anal. Biochem.* 151:504-509(1985).
Nyren, et al., "Solid Phase DNA Minisequencing by an Enzymatic Luminometric Inorganic Phyrophosphate Detection Assay", *Anal Biochem.* 208(1):171-175 (1993).
Pantano, et al., "Analytical Applications of Optical imaging Fibers", *Analytical Chemistry*, 67:481A-487A (1995).
Pantano, "Ordered Nanowell Arrays", *Chem Mater*, 8(12):2832-2835 (1996).
Pastinen, et al., "Minisequencing: A Specific Tool for DNA Analysis and Diagnostics on Oligonucleotide Arrays", *Genome Research*, 7:606-614 (1997).
Pauwels, et al., "Biological Activity of New 2-5A Analogues", *Chemica Scripta.* 26:141-145 (1986).
Pearson and Lipman, "Improved tools for biological sequence comparison", *Proc. Natl. Acad. Sci. USA*, 85:2448 (1998).
Pease, et al., "Light-generated oligonucleotide array for rapid DNA sequence analysis", *Proc. Natl. Acad. Sci. USA*, 91(11):5502-5026 (1994).
Peterson, J I. et al., "Fiber Optic pH Probe for Physiological Use.", *Analytical Chemistry.*, 52(6):864-869 (1980).
Peterson, et al., "Fiber-Optic Sensors for Biomedical Applications", *Science.*, 13:;123-127 (1984).
Piunno, "Fiber-Optic DNA Sensor for Fluorometric Nubleic Acid Determination", *Analytical Chemistry*, 67(15):2635-2643 (1995).
Pope, "Fiber Optic Chemical Microsensors Employing Optically Active Silica Microspheres", *SPIE* 2388:245-256 (1995).
Ranki, et al., "Sandwich hybridization as a convenient method for the detection of nucleic acids in crude samples", *Gene*, 21:77-85 (1983).
Rawls, Rebecca , "Promising Clinical Results and Chemical Strategies for Further improvements Delight Antisense Drug Researchers", *Chemical & Engineering News*, pp. 35-39 (1997).
Reeves, R. E. et al., "Enzymic assay method for inorganic pyrophosphate", *Anal. Biochem.* 28:282-287 (1969).
Ronaghi, M et al., "A Sequencing Method Based on Real-Time Phyrophosphate", *Science.* 281(5375):363-365 (1998).
Ronaghi, et al., "Analyses of Secondary Structures in DNA by Pyrosequencing", *Anal. Biochem.* 1:65-71 (1999).

Ronaghi, M et al., "Real-time DNA sequencing using detection of pyrophosphate release", *Anal. Biochem.* 242(1):84-89 (1996).
Rothberg, J M. et al., "The development and impact of 454 sequencing", *Nature Biotechnology*, 26(10):1117-1124 (2008).
Saari, et al., "pH Sensor Based on Immobilizied Fluoresceinamine", *Analytical Chemistry*, 54(4):821-823 (1982).
Sabanayagam, et al., "Molecular DNA Switches and DNA chips", *SPIE:Progress in Biomedical Optics*, 3606:90-97 (1999).
Sambrook, et al., "Molecular Cloning: A Laboratory Manua", 3rd Edition, Cold Spring Harbor Laboratory, New York, (2001).
Sanger, F et al., "DNA Sequencing with chain-terminating inhibitors", *Proc. Natl. Acad. Sci USA*, 74(12):5463-5467 (1977).
Sanghvi, Y.S. and, Cook, P. Dan, Eds. et al., "Carbohydrate Modifications in Antisense Research", *ASC Symposium Series 580*, Ch 2,3,6 and 7, 1994.
Sawai, "Synthesis and Properties of Oligoadenylic Acids Conatining 2'-5' Phosphoamide Linkage.", *Chemistry Letters* 805-808 (1984).
Schafer, et al., "DNA variation and the future of human genetics", *Nature Biotechnology*, 16:33-39 (1998).
Schwab, et al., "Versatile, Efficient Raman Sampling with Fiber Optics", *Analytical Chemistry*, 56(12):2199-2204 (1984).
Seitz, "Chemical Sensors Based on Fiber Optics", *Analytical Chemistry*, 56(1):16A-34A (1984).
Seitz, et al., "Chemical Sensors Based on Immobilized Indicators and Fiber Optics", *CRC Critical Reviews in Analytical Chemistry*, 19(2):135-173 (1988).
Seradyn, "Sera-Mag Streptavadin Magnetic Microparticles", *Particle Technology*, 1-7 (1996).
Shabarova, Za , "Chemical development in the design of oligonucleotide probes for binding to DNA and RNA", *Biochimie*, 70:1323-1334 (1998).
Sheldon, et al., "Matrix DNA hybridization", *Clinical Chemistry*, 39(4):718-719 (1993).
Shoemaker, "Quantitative phenotypic analysis of yeast deletion mutants using a highly parallel molecular bar-coding strategy", *Nature Genetics*, 14(4):450-456 (1996).
Sigman, D S. , "Chemical nucleases", *Chem. Rev.*, 93:2295-2316 (1993).
Sigman, et al., "DNase Activity of 1, 10-Phenanthroline-Copper Ion", *Nucleic Acids and Molecular Biology*, 3:13-27 (1989).
Smith, et al., "Fluorescence detection in automated DNA sequence analysis", *Nature*, 321:674-679 (1986).
Sooknanan, et al., "Nucleic Acid Sequence-Based Amplification", *Molecular Methods for Virus Detection* Academic Press, Ch. 12, pp. 261-285 (1995).
Sprinzl, et al., "Enzymatic Incorporation of ATP and CTP Analogues into the 3' End tRNA.", *Eur. J. Biochem.*, 81:579-589 (1977).
Stimpson, et al., "Real-time detection of DNA hybridization and melting on oligonucleotide arrays on glass supports", *Nucleic Acids Res.*, 22:5456-5465 (1994).
Strachan, "A Rapid General Method for the IDentification of PCR Products Using a Fibre-Optic Biosensor and its Application to the Detection of Listeria", *Letters in Applied Microbiology*, 21(1):5-9 (1995).
Studier, "A strategy for high-volume sequencing of cosmid DNAs: random and directed priming with a library of oligonucleotides," *Proc. Natl. Acad. Sci. USA*, 86:6917-6921 (1989).
Syvanen, et al., "A Primer-Guided Nucleotide Incorporation Assay in the Genotyping of Apolipoprotein E", *Genomics*, 8:684-692 (1990).
Syvanen, "Detection of point mutations in human genes by the solid-phase minisequencing method", *Clinica Chimica Acta*, 226:225-236 (1994).
Syvanen, Ann-Christine , "From gels to chips: "Minisequencing" Primer Extension for Analysis of point Mutations and Single Nucleotide Polymorphisms", *Human Mutation*, 13:1-10 (1999).
Thomas, et al., "Amplification of padlock probes for DNA diagnostics by cascade rolling circle amplification or the polymerase chain reaction", *Arch. Pathol. Lab. Med.*, 123:1170-1176 (1999).
Tijssen, "Overview of principles of hybridization and the strategy of nucleic acid assays", *Techniques in Biochemistry and Molecular Biology-Hybridization withy Nucleic Acid Probes*, 1993.

Ugozzoli, Luis, "Detection of Specific Alleles by Using Allele-Specific Primer Extension Followed by Capture on Solid Support", *GATA* 9(4):107-112 (1992).

Von Kiedrowski, et al., "Parabolic growth of a self-replicating hexadeoxynucloetide bearing a 3'-5'-phosphoamidate linkage", *Angew. Chem. Intl. Ed. English*, 30:423 (1991).

Walker, et al., "A Chemiluminescent DNA Probe Test Based on Strand Displacement Amplification", *Molecular Methods for Virus Detection*, 1995, Academic Press Inc. Ch 15 pp. 329-349 (1995).

Walker and Linn, et al., "Detection of *Mycobacterium tuberculosis* thermophilic strand displacement amplification and fluorescence polarization", *Clinical Chemistry.*, 42:1604-1608 (1996).

Wallace, et al., "Hybridization of synthetid oligodeoxyribonucleotides to phi chi 174 DNA: the effect of single base pair mismatch", *NAR*, 6:3543-3547 (1979).

Walt, D , "Bead Based Fiber-Optic Arrays", *Science*, 287 :451-452 (1999).

Walt, et al., "Design, Preparation, and Applications of Fiber-Optic Chemical Sensors for Continuous Monitoring", *Fiber Optic Chemical Sensors, Chemical Sensors and Microinstrumentation* 252-272 (1989).

Walt, "Fiber-Optic Imaging Sensors", *Accounts of Chemical Research*, 31(5)267-278 (1998).

Walt, "Fiber-Optic Sensors for Continuous Clinical Monitoring", *Proc. IEEE*, 80(6):903-911 (1992).

Wang, D G. , "Large-Scale Identification, Mapping, and Genotyping of Single-Nucleotide Polymorphisms in the Human Genome", *Science*, 280:1077-1082 (1998).

Whitcombe, D. , "Detection of PCR products using self-probing amplicons with fluorescence", *Nature Biotechnology*, 17:804-807 (1999).

Wolfbeis, "Fiber Optical Fluorosensors in Analytical and Clinical Chemistry", *Molecular Luminescence Spectroscopy, Methods and Applications (S.G. Schulman, editor), Wiley & Sons, New York*, 129-280 (1988).

Wolfbeis, et al., "Fiber-Optic Fluorosensor for Oxygen and Carbon Dioxide", *Analytical Chemistry*, 60:2028-2030 (1988).

Xu, et al., "High sequence fidelity in a non-enzymatic DNA autoligation reaction", *NAR*, 27:875-881 (1999).

Yoshinari, et al., "Oligoamines as Simple and Efficient Catalyst for RONA hHydrolysis", *J. Am. Chem. Soc.*, 113:5899-5901 (1991).

Zhu, "Purification and Characterization of PRD1 DNA polymerase", *Biochem. Biophys. Acta.*, 1219:267-276 (1994).

Zhujun, et al., "A Fluorescence Sensor for Quantifying pH in the Range from 6.5 to 8.5", *Analytica Chimica Acta* 160:47-55 (1984).

* cited by examiner

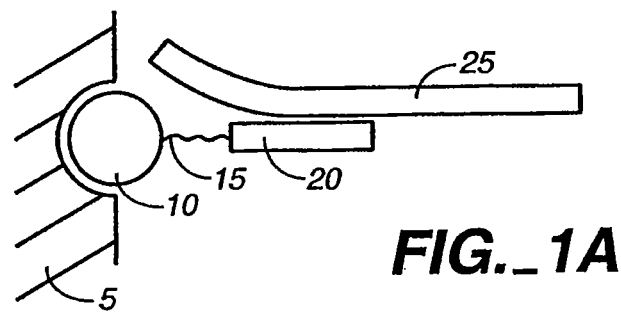
FIG._1A
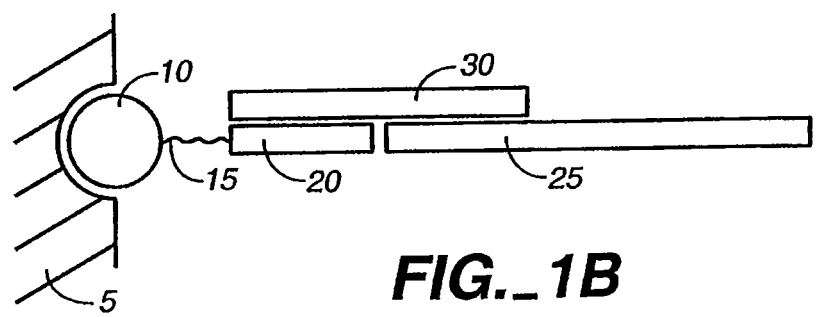
FIG._1B
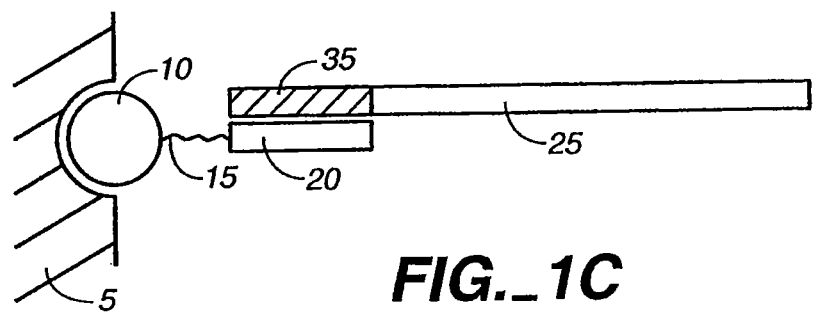
FIG._1C

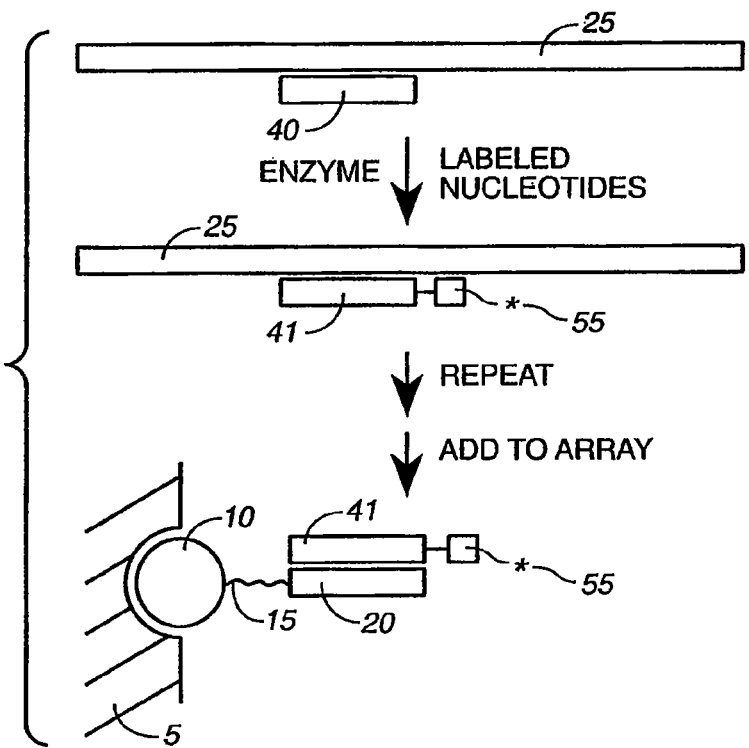
*FIG._2A*
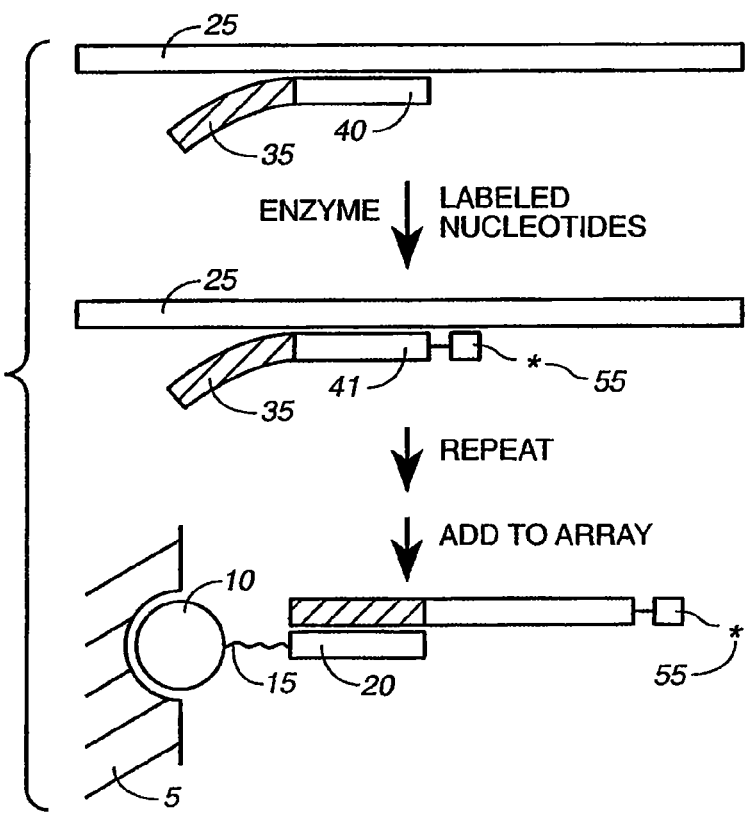
*FIG._2B*

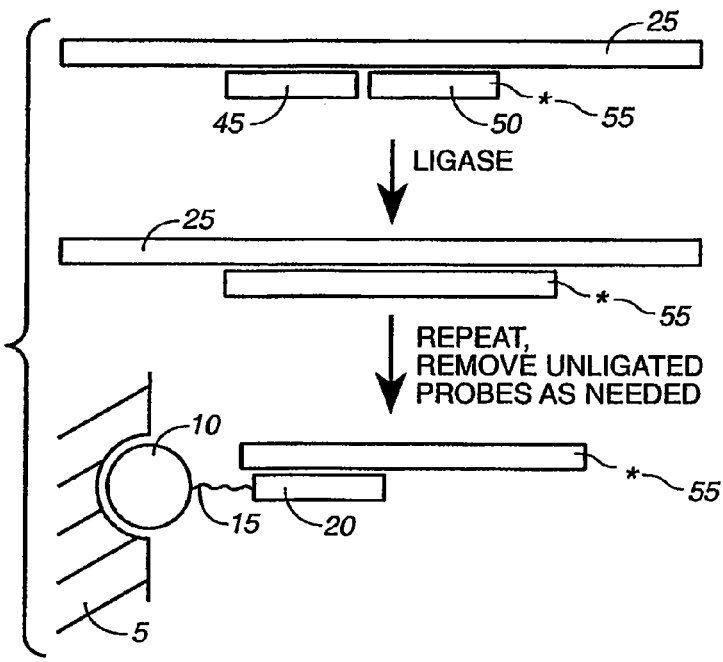
FIG._3A
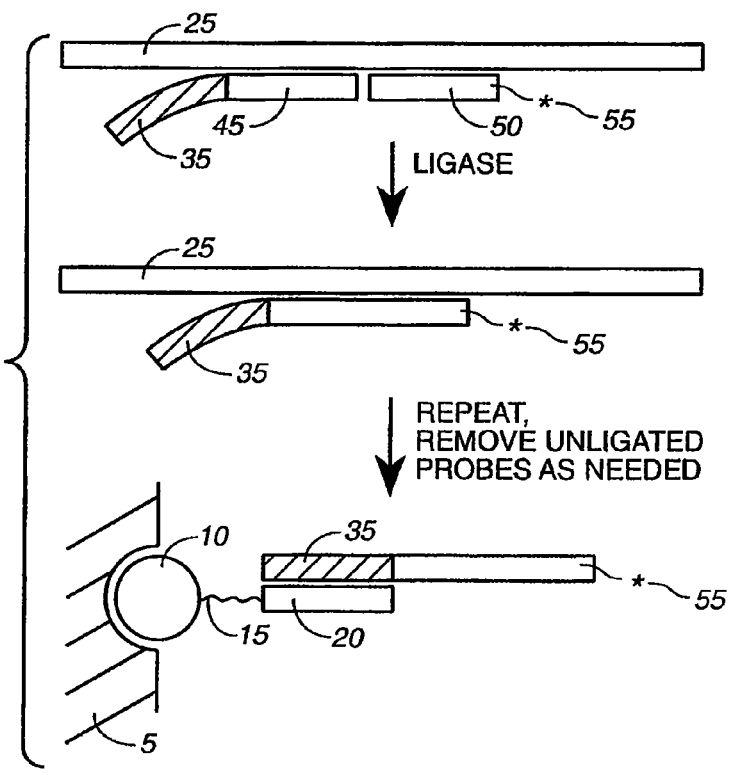
FIG._3B

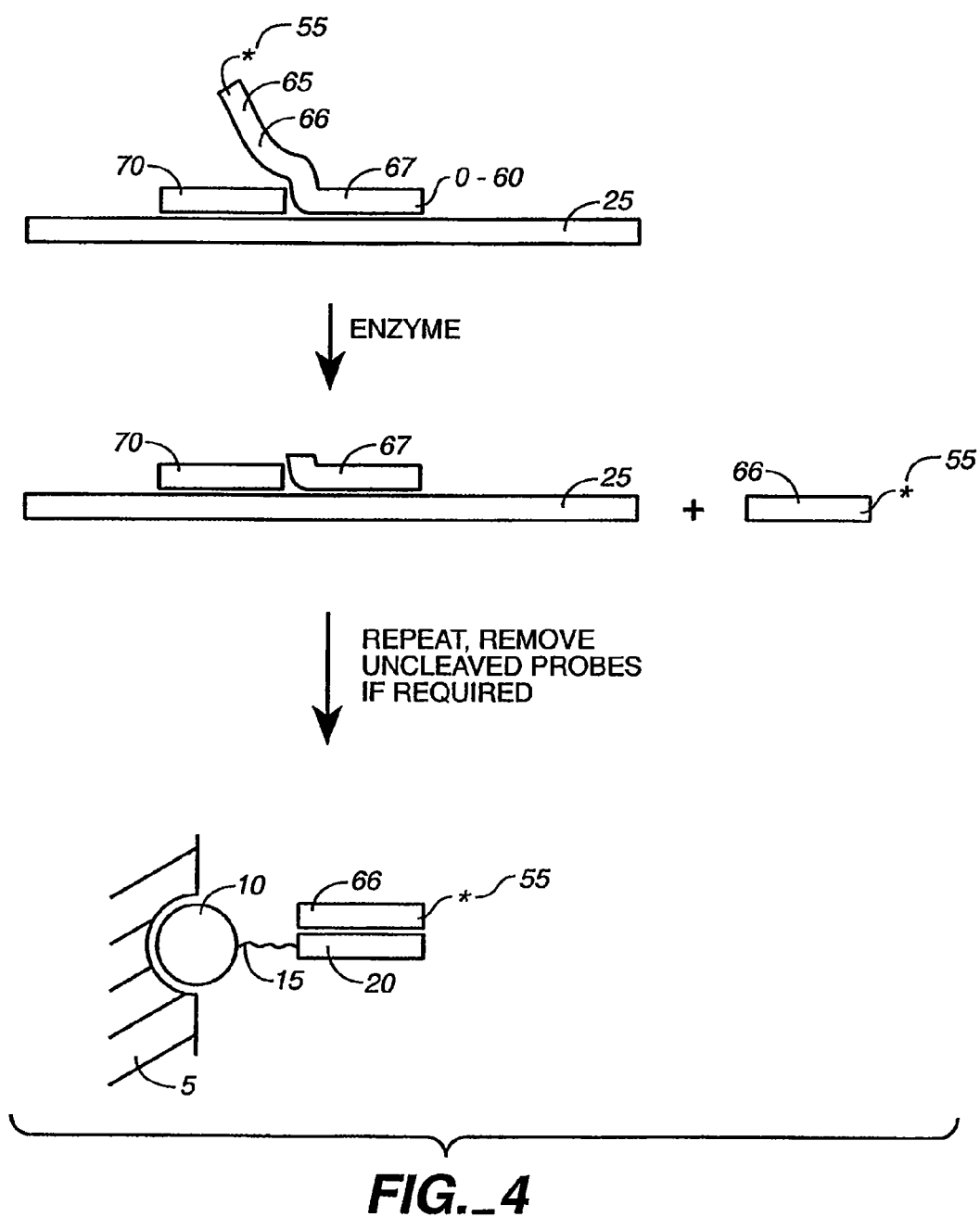
FIG._4

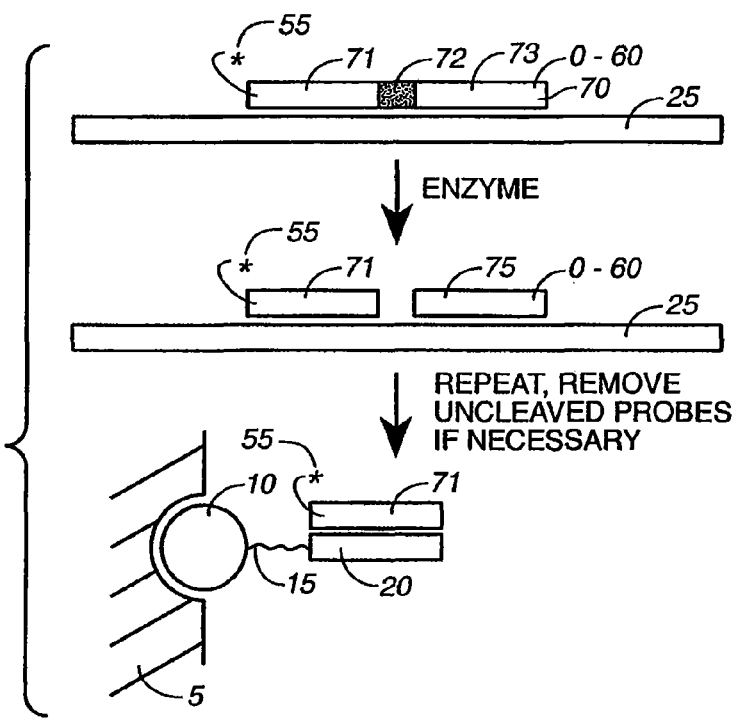
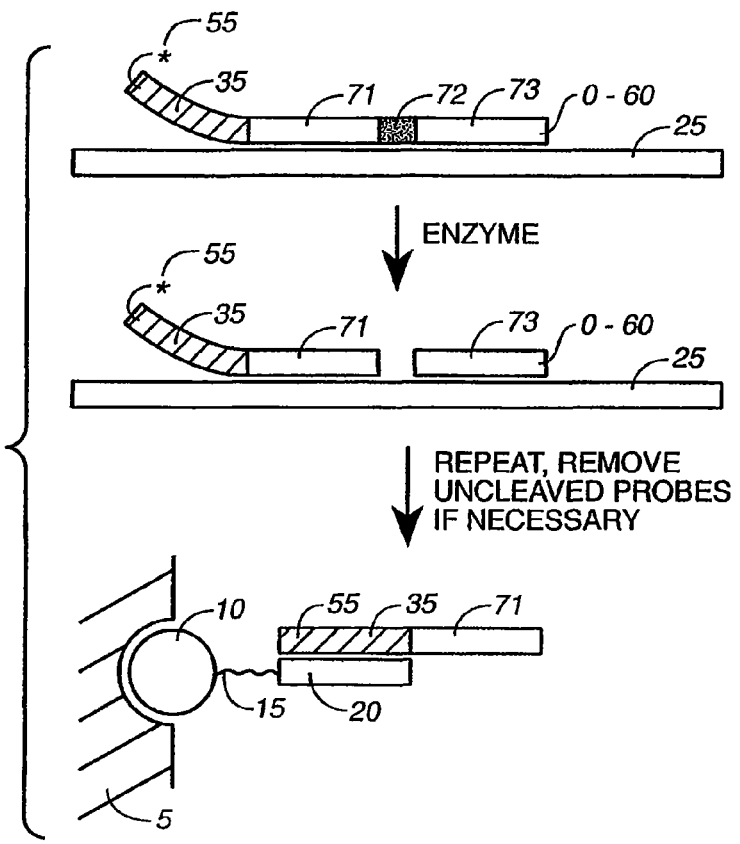
FIG._5A
FIG._5B

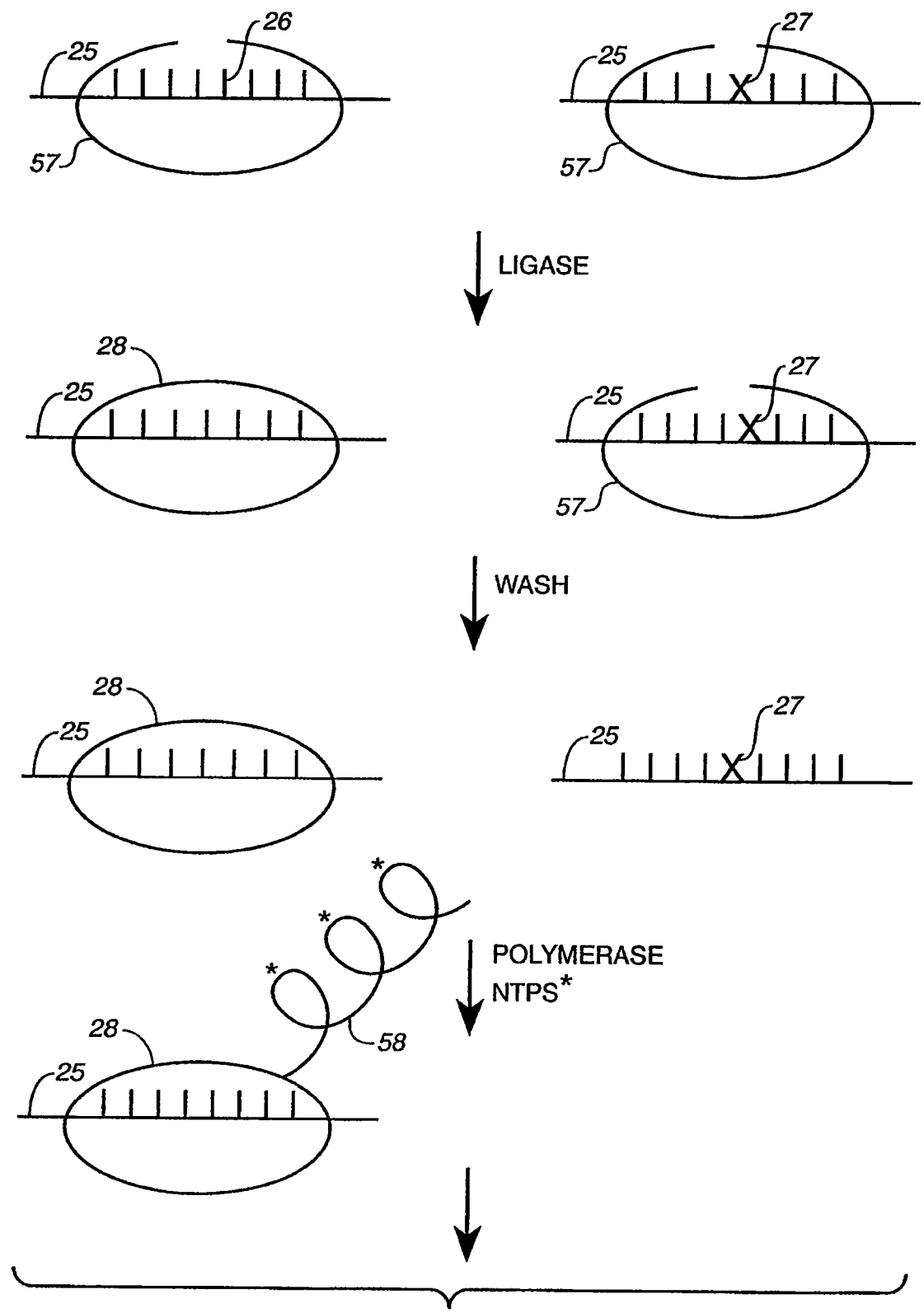
FIG._6A

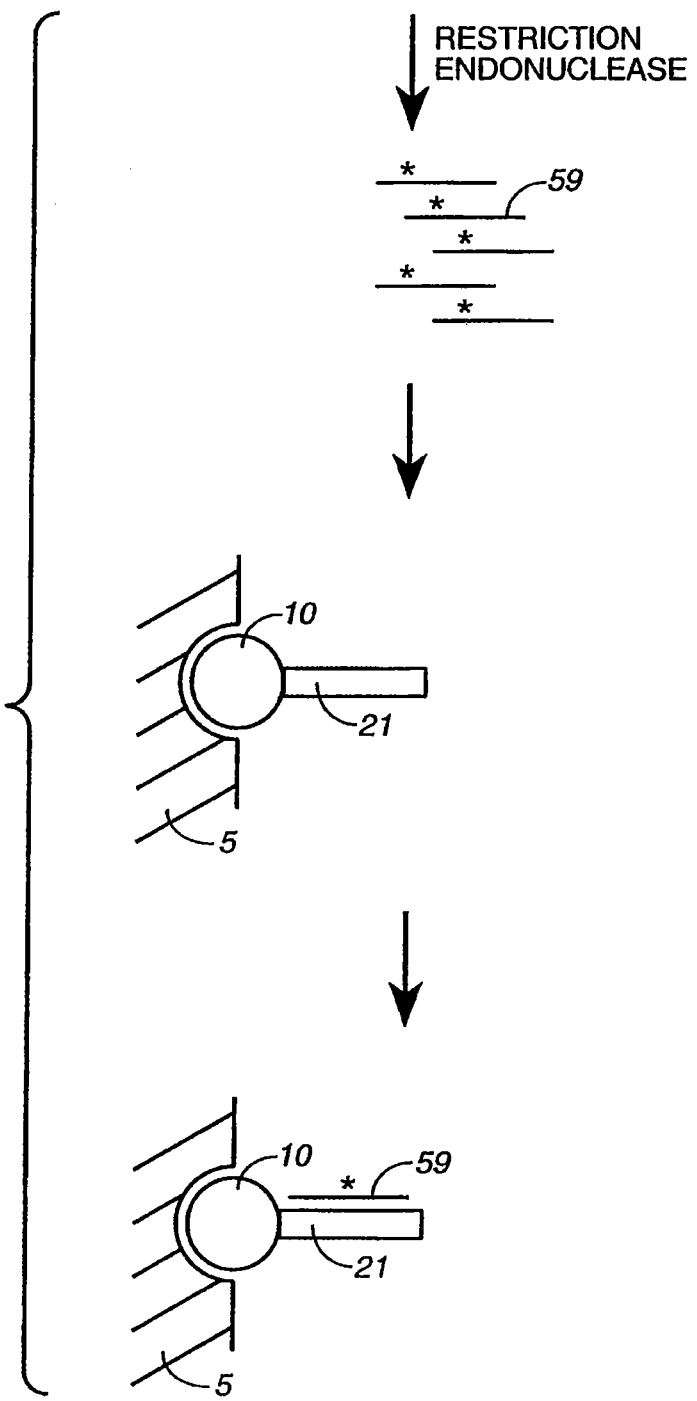
FIG._6B

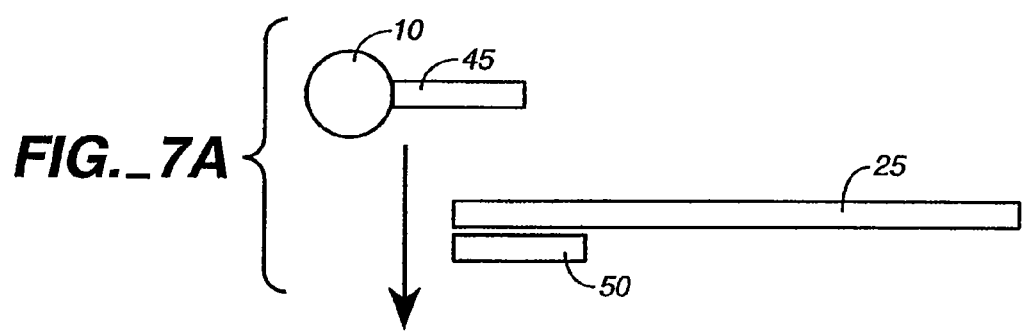
FIG._7A
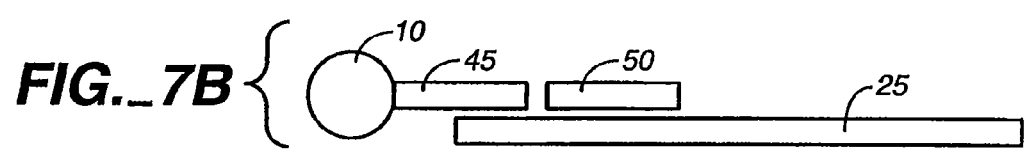
FIG._7B
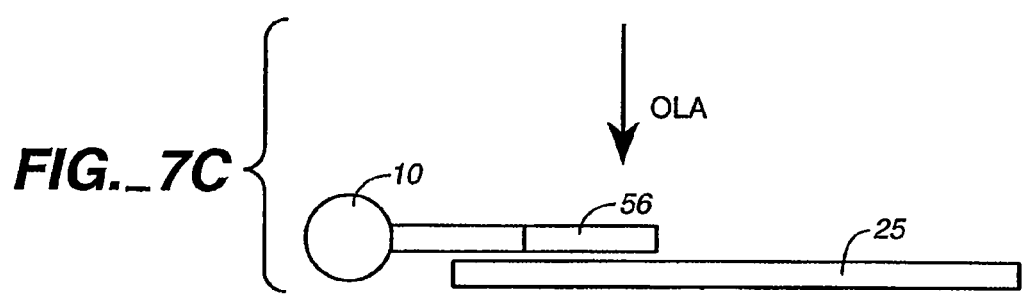
FIG._7C
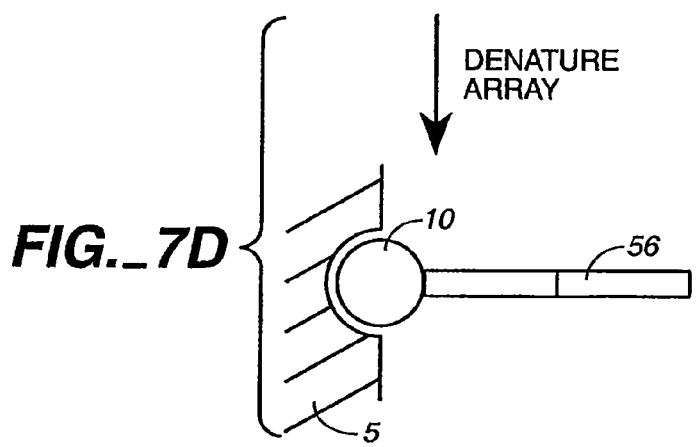
FIG._7D

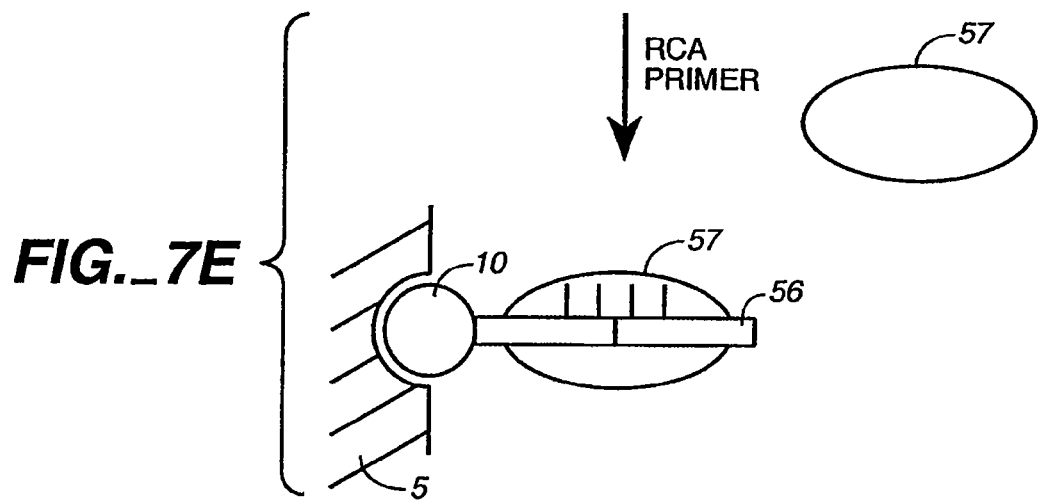
FIG._7E
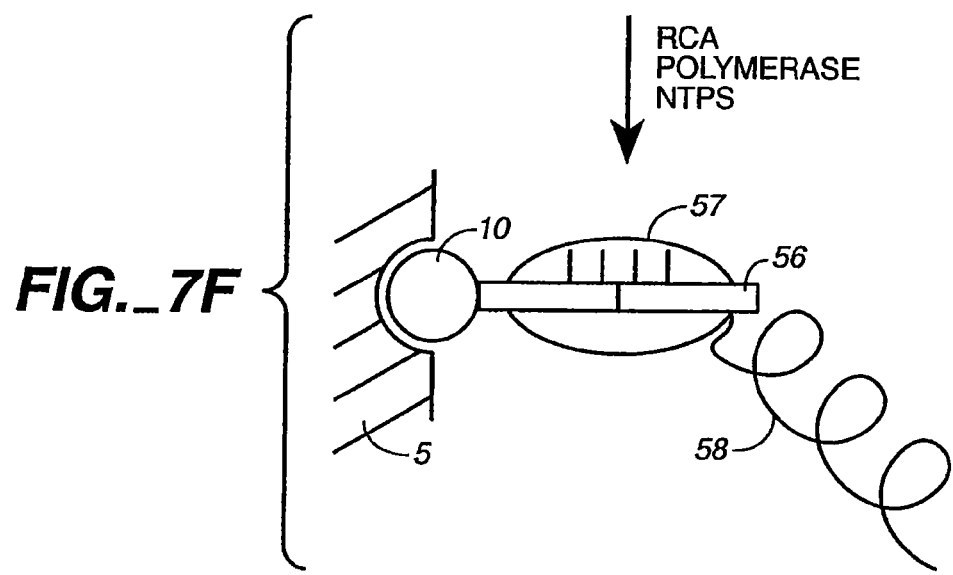
FIG._7F

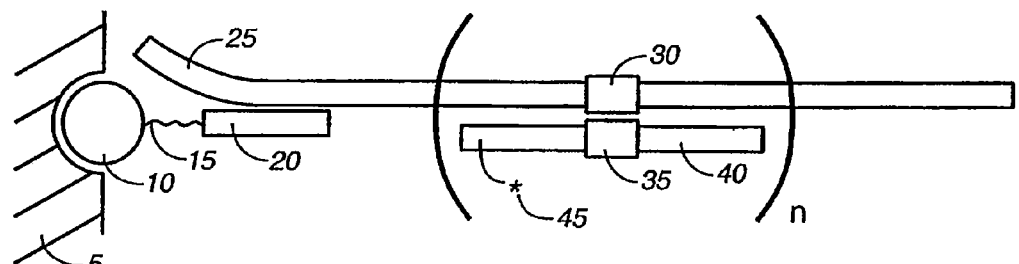
FIG._8A
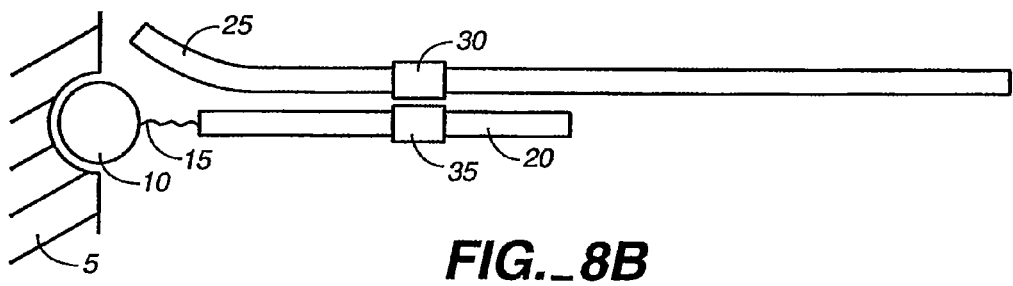
FIG._8B
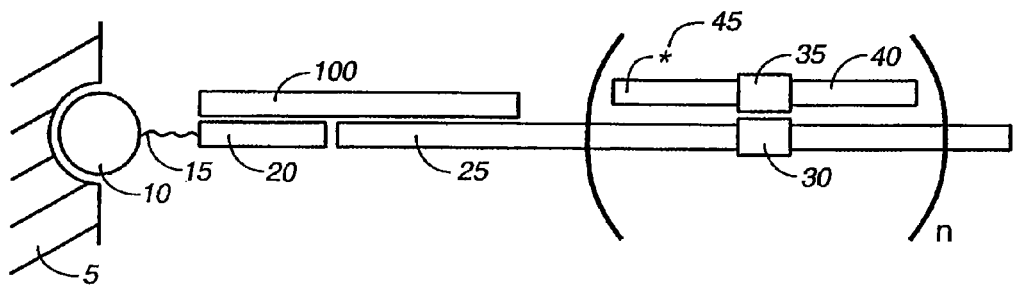
FIG._8C

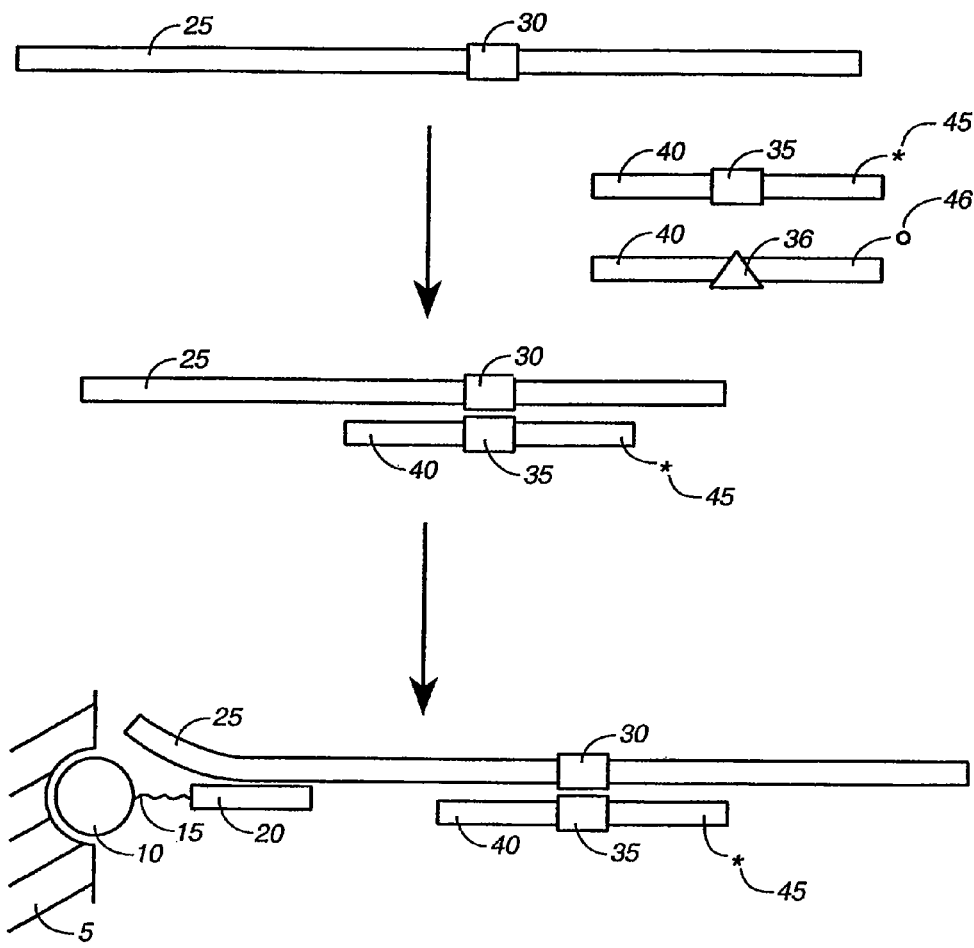
FIG._8D
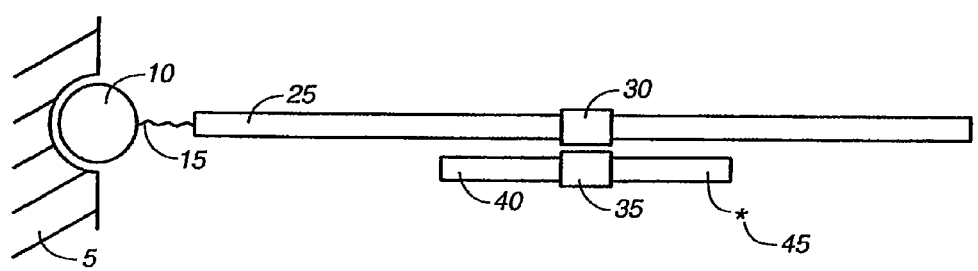
FIG._8E

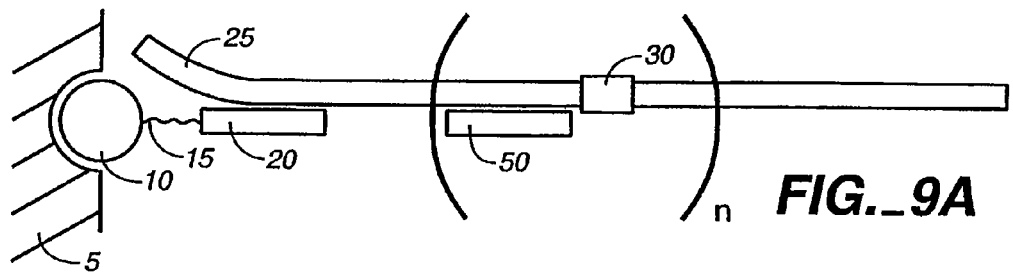
*FIG._9A*
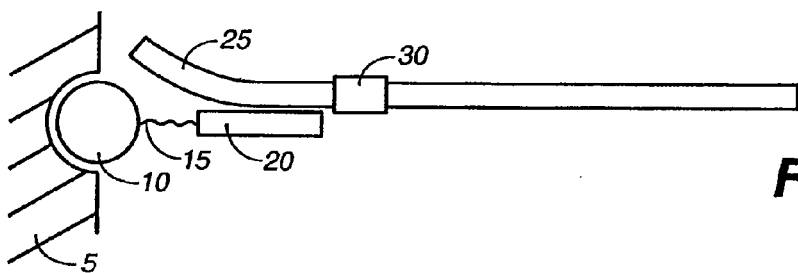
*FIG._9B*
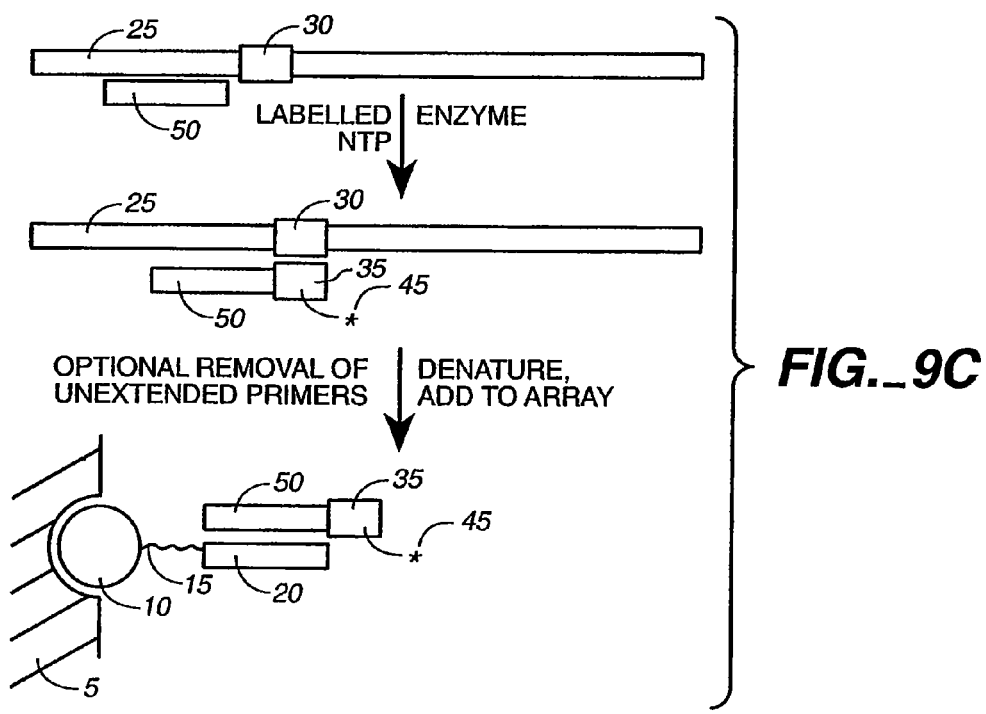
*FIG._9C*
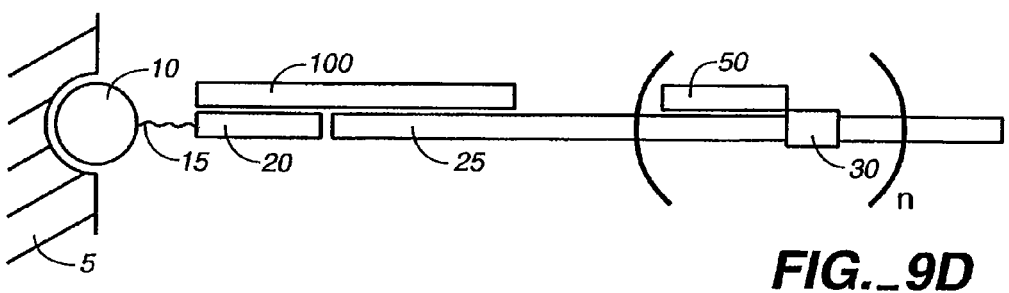
*FIG._9D*

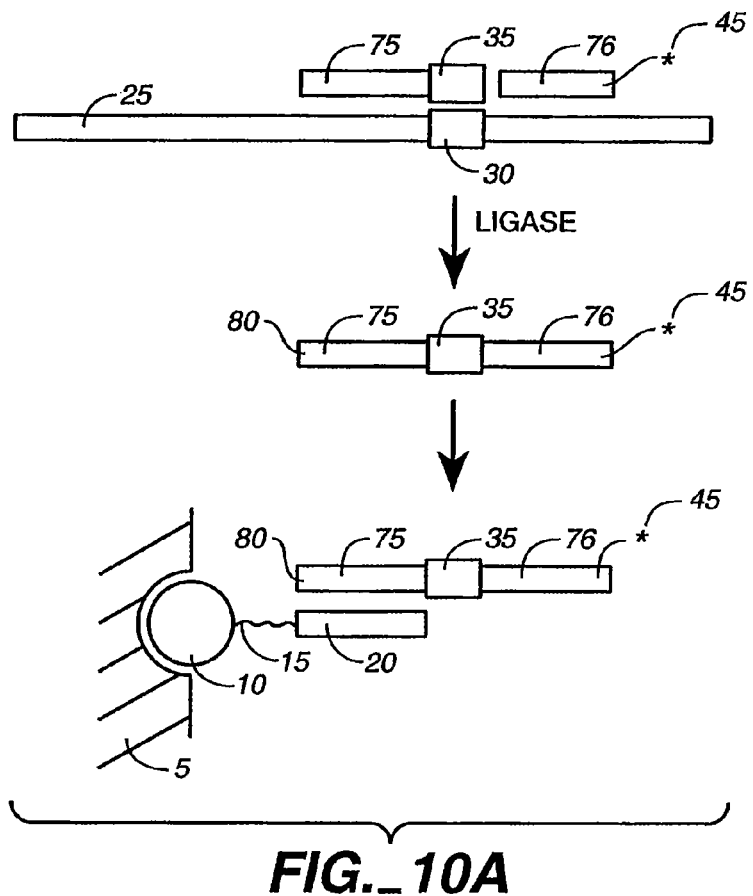
FIG._10A
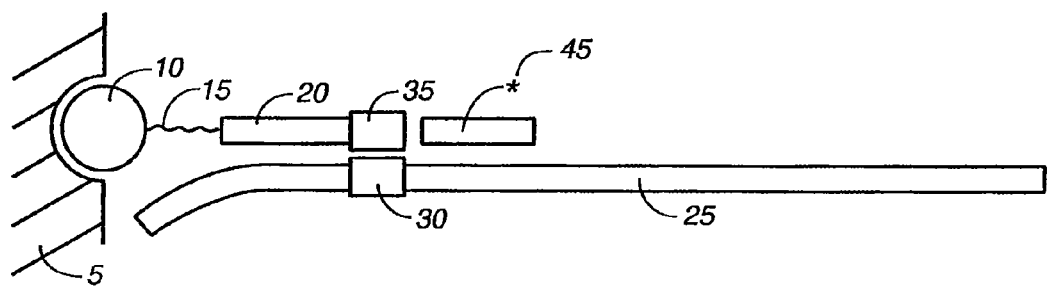
FIG._10B

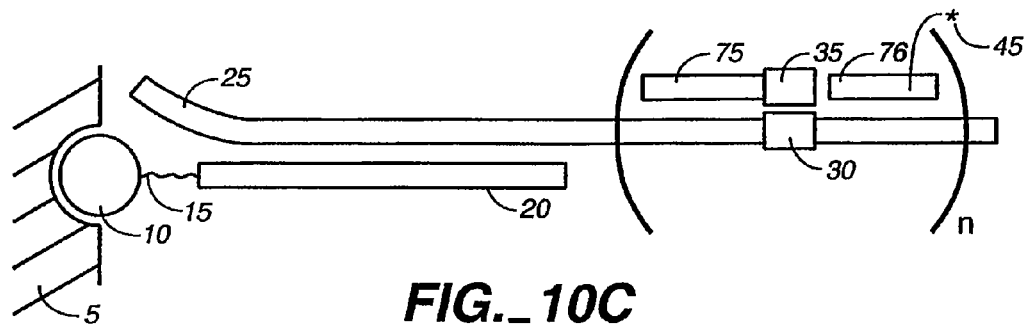
FIG._10C
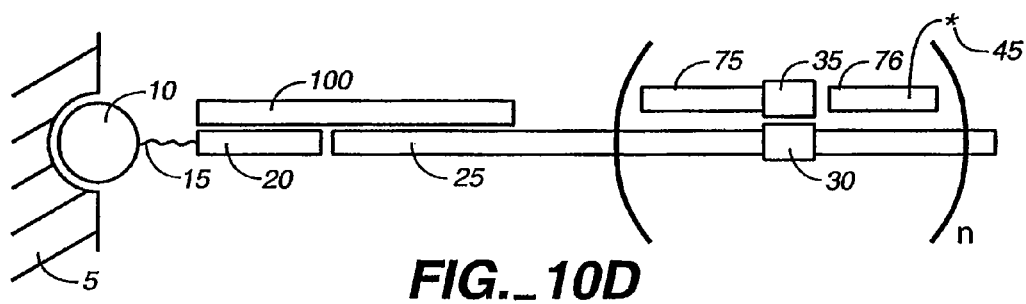
FIG._10D
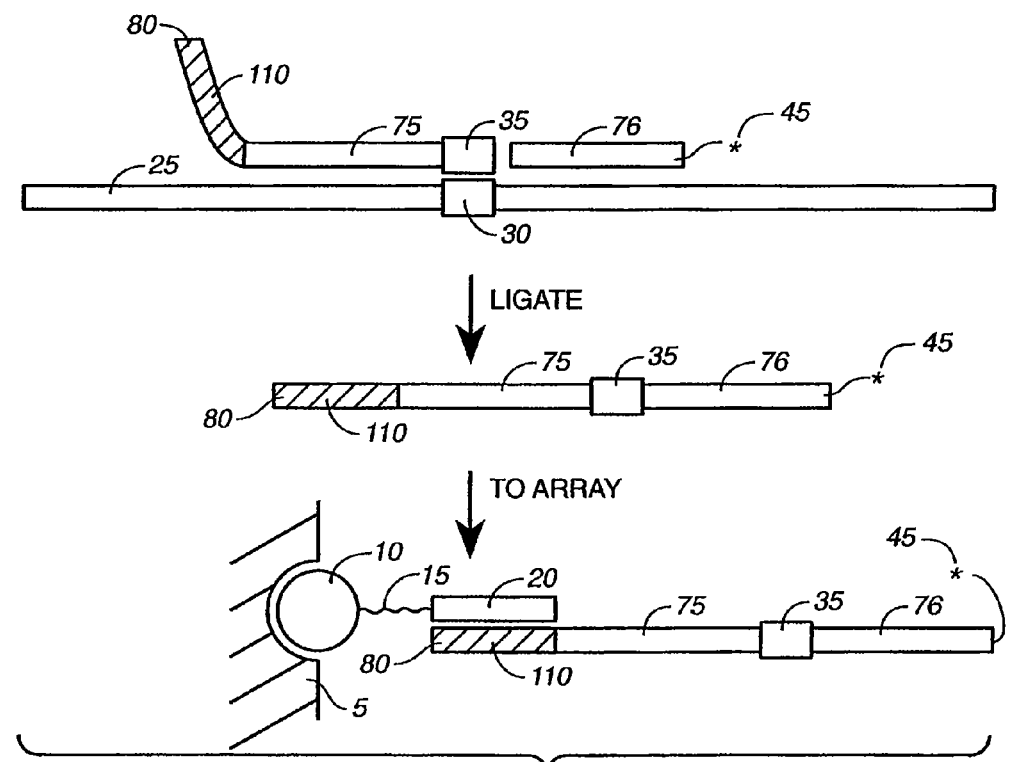
FIG._10E

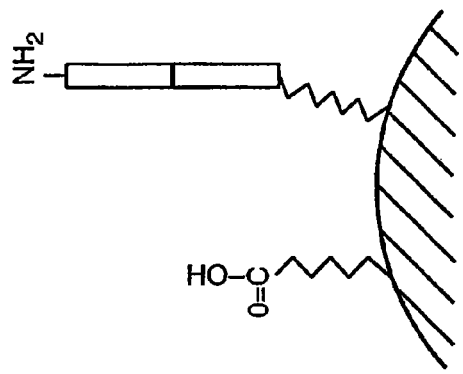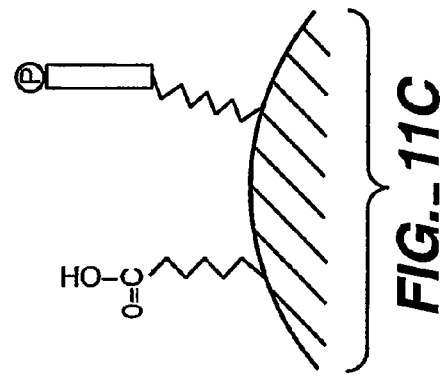
FIG._11C
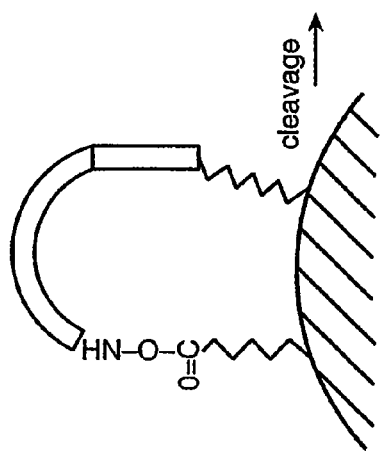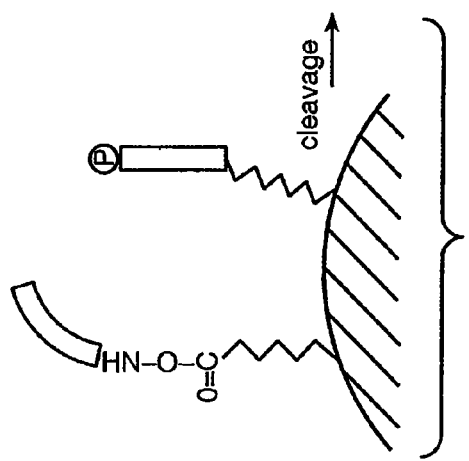
FIG._11B
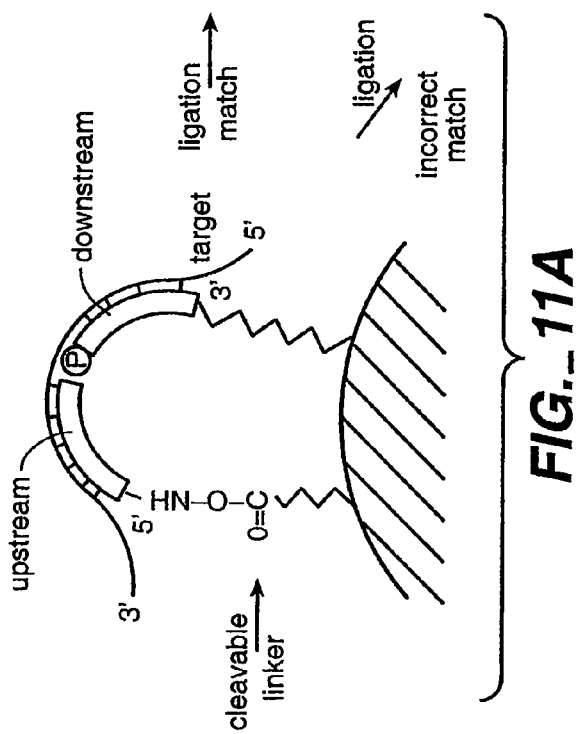
FIG._11A

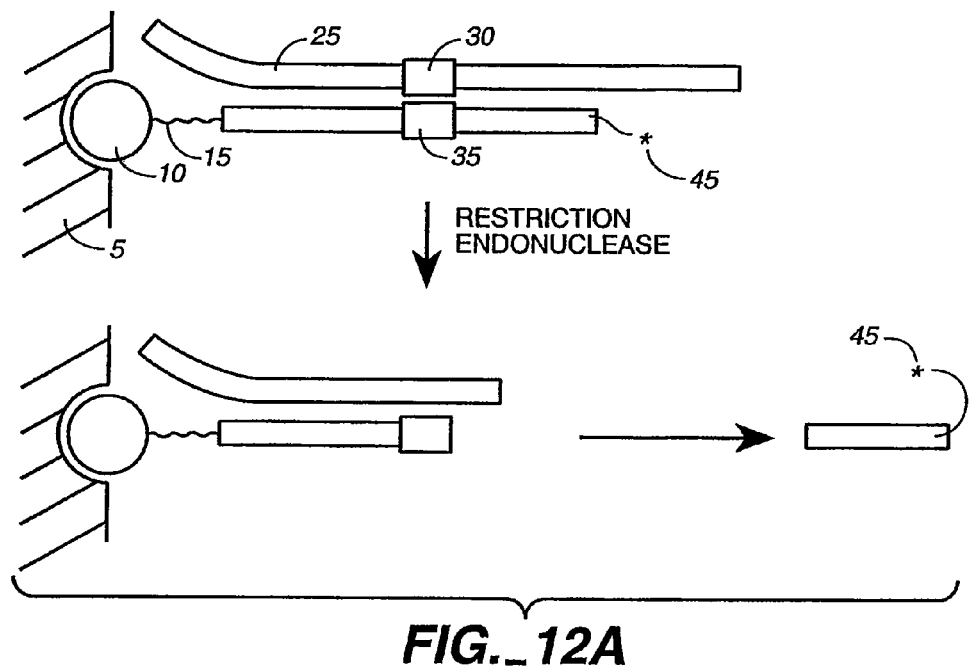
FIG._12A
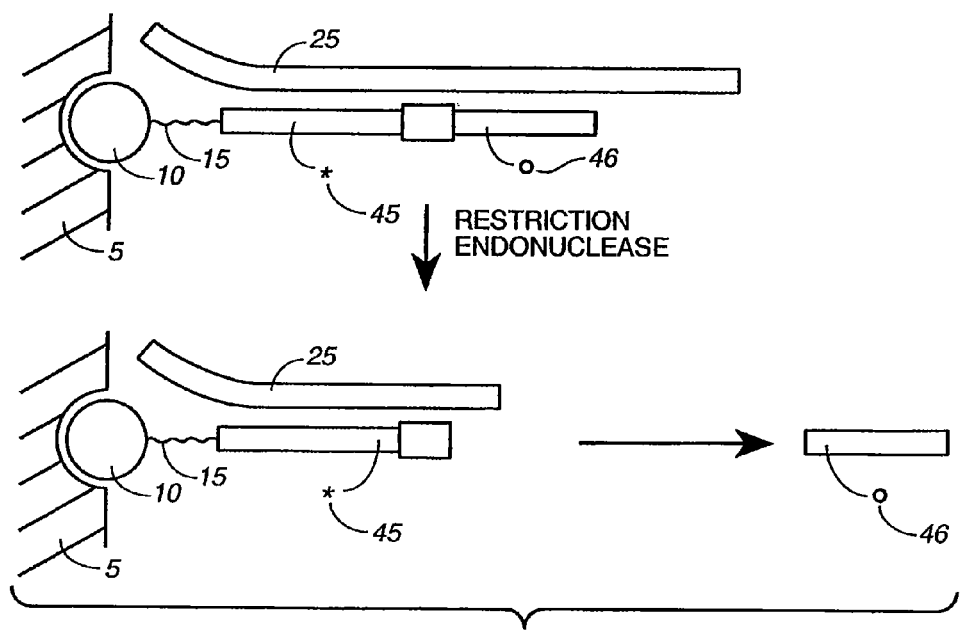
FIG._12B

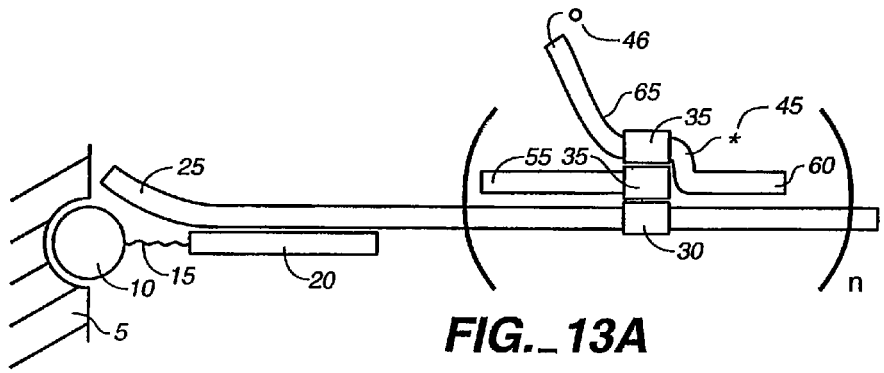
FIG._13A
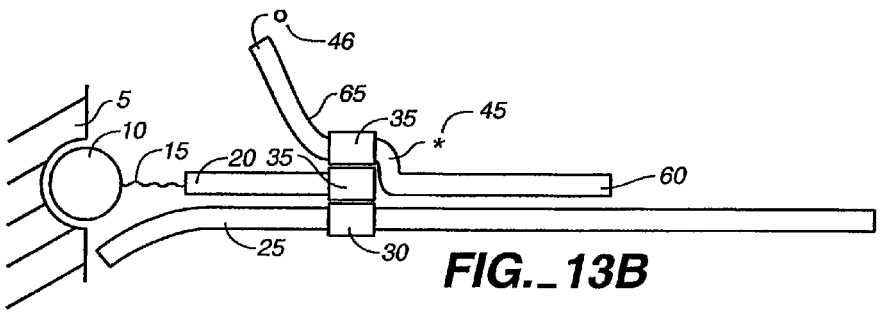
FIG._13B
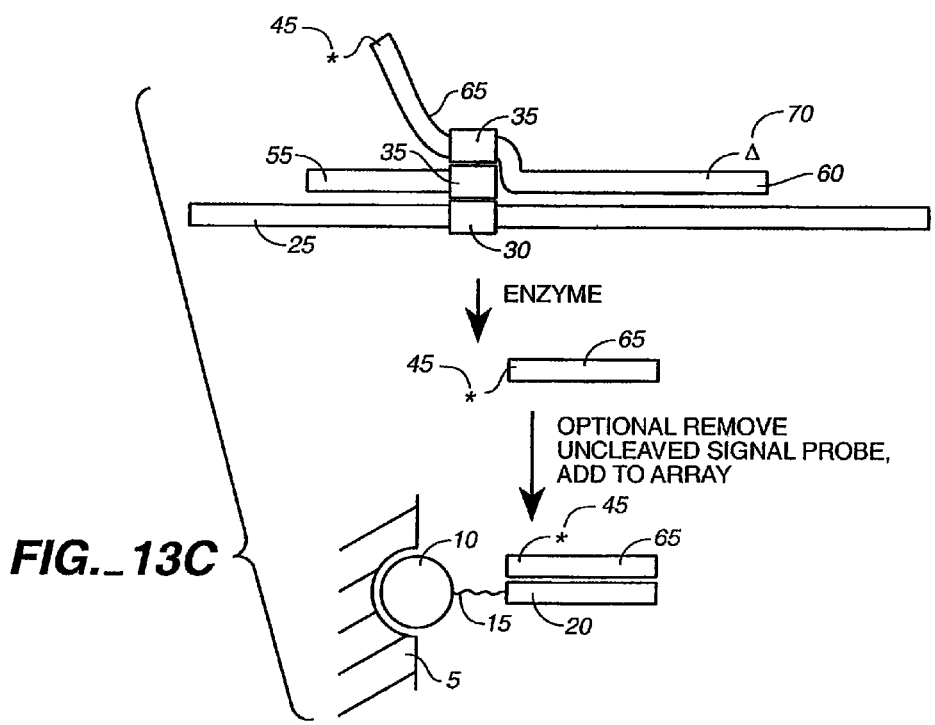
FIG._13C

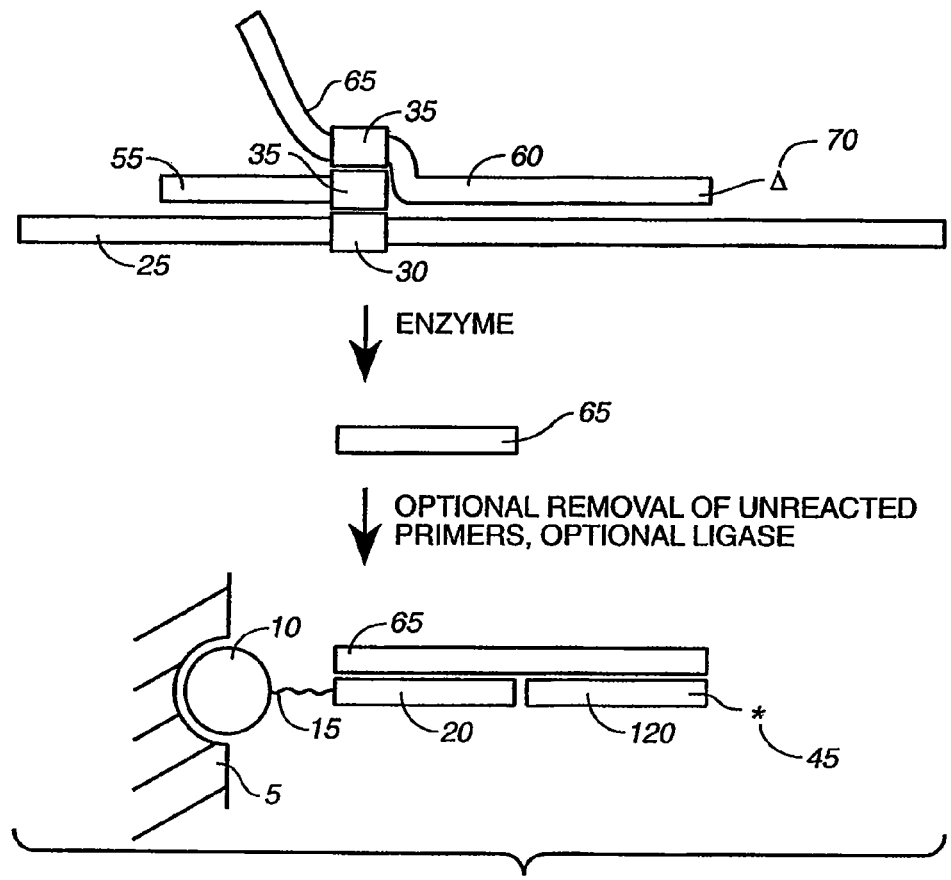
FIG._13D
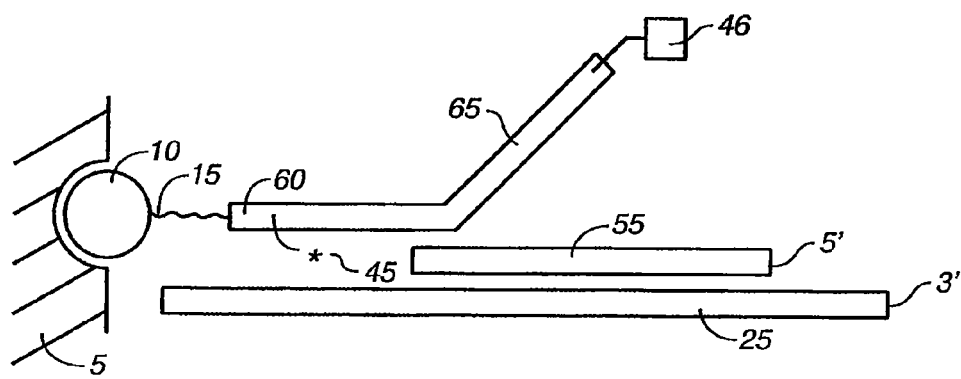
FIG._13E

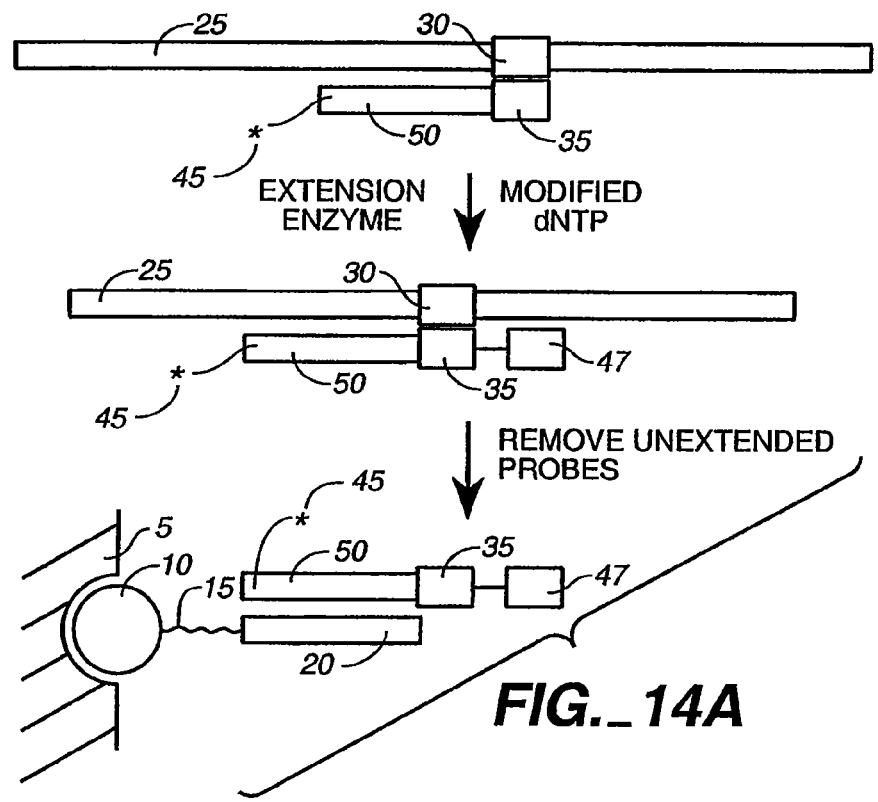
FIG._14A
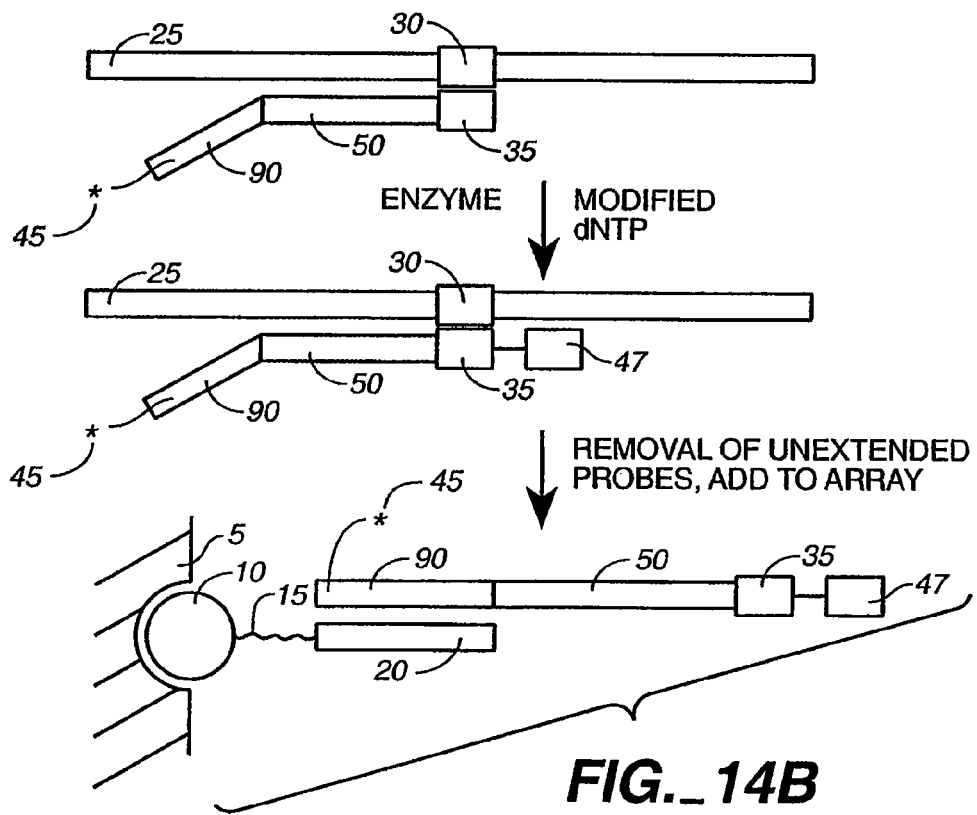
FIG._14B

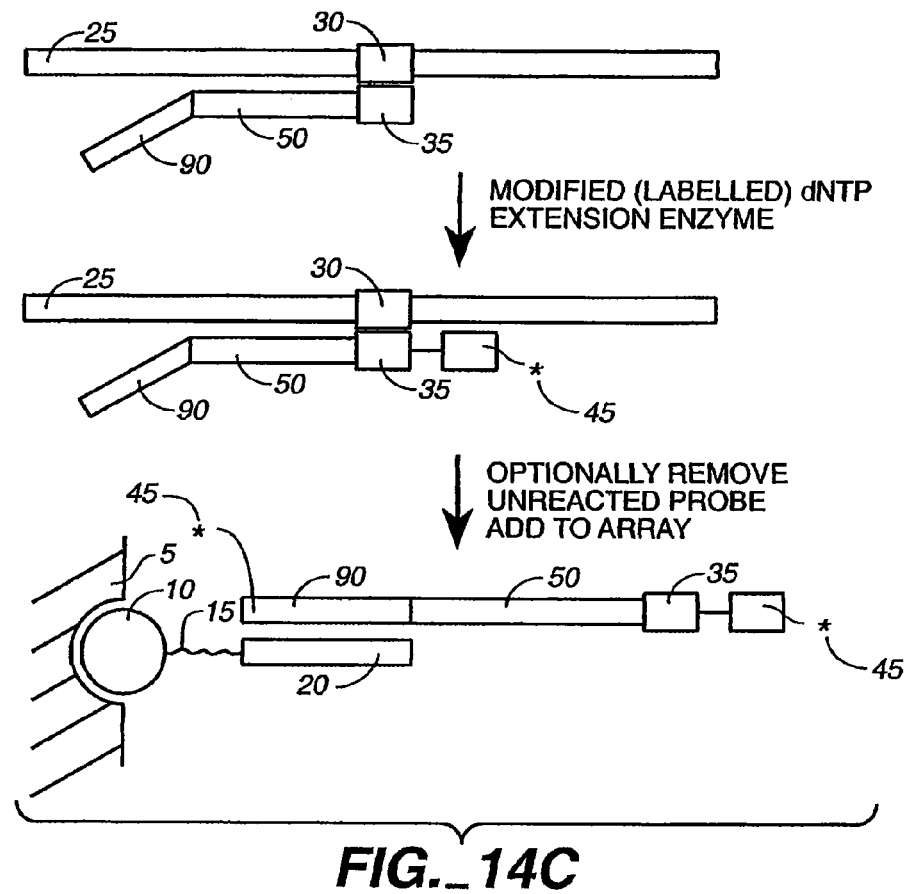
FIG._14C
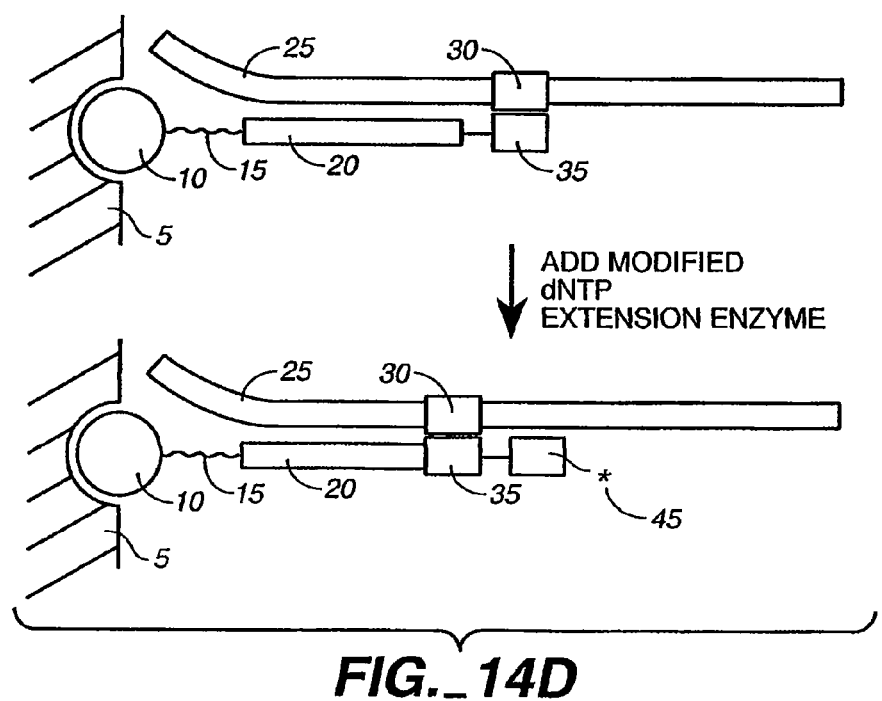
FIG._14D

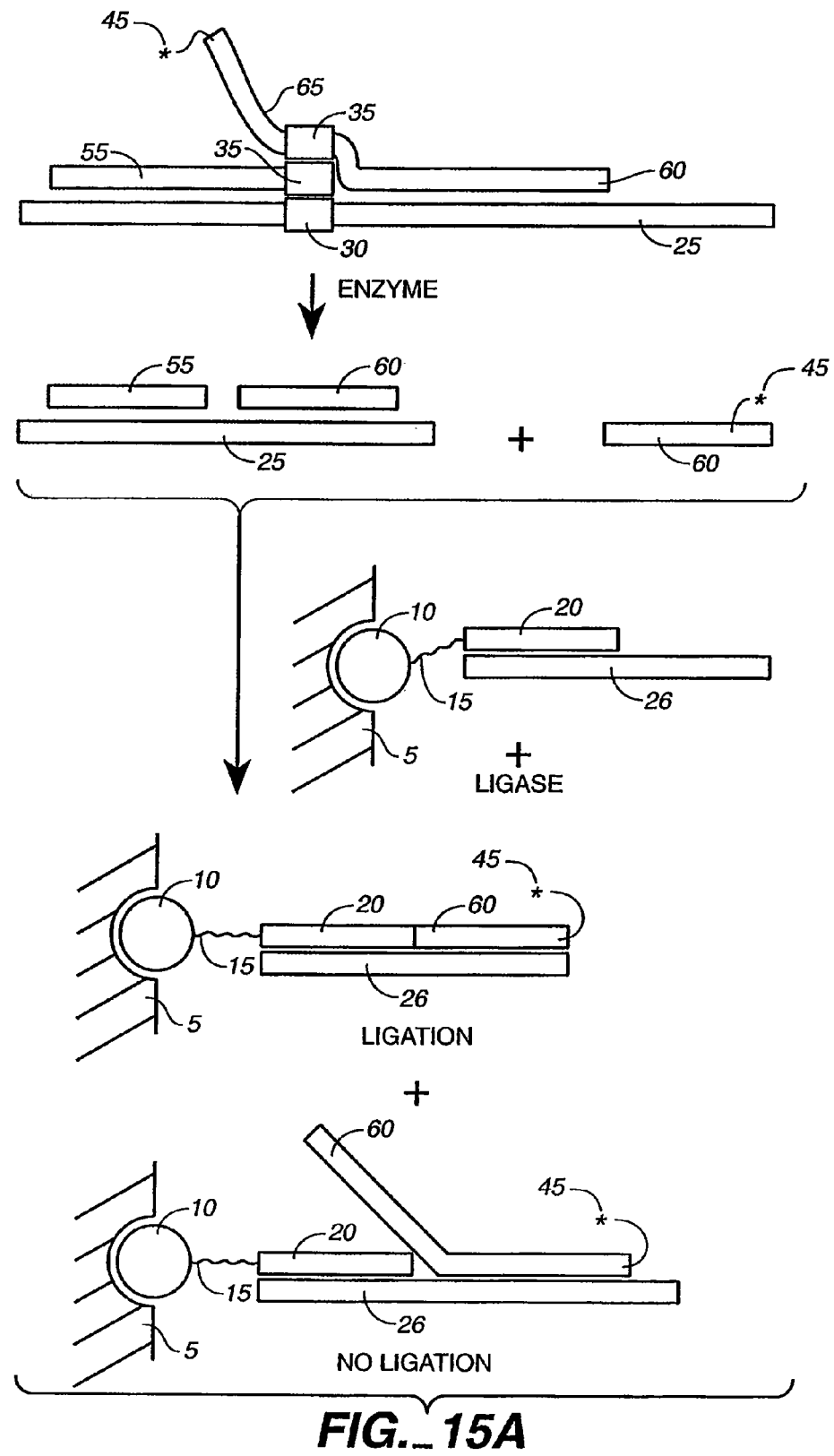
FIG._15A

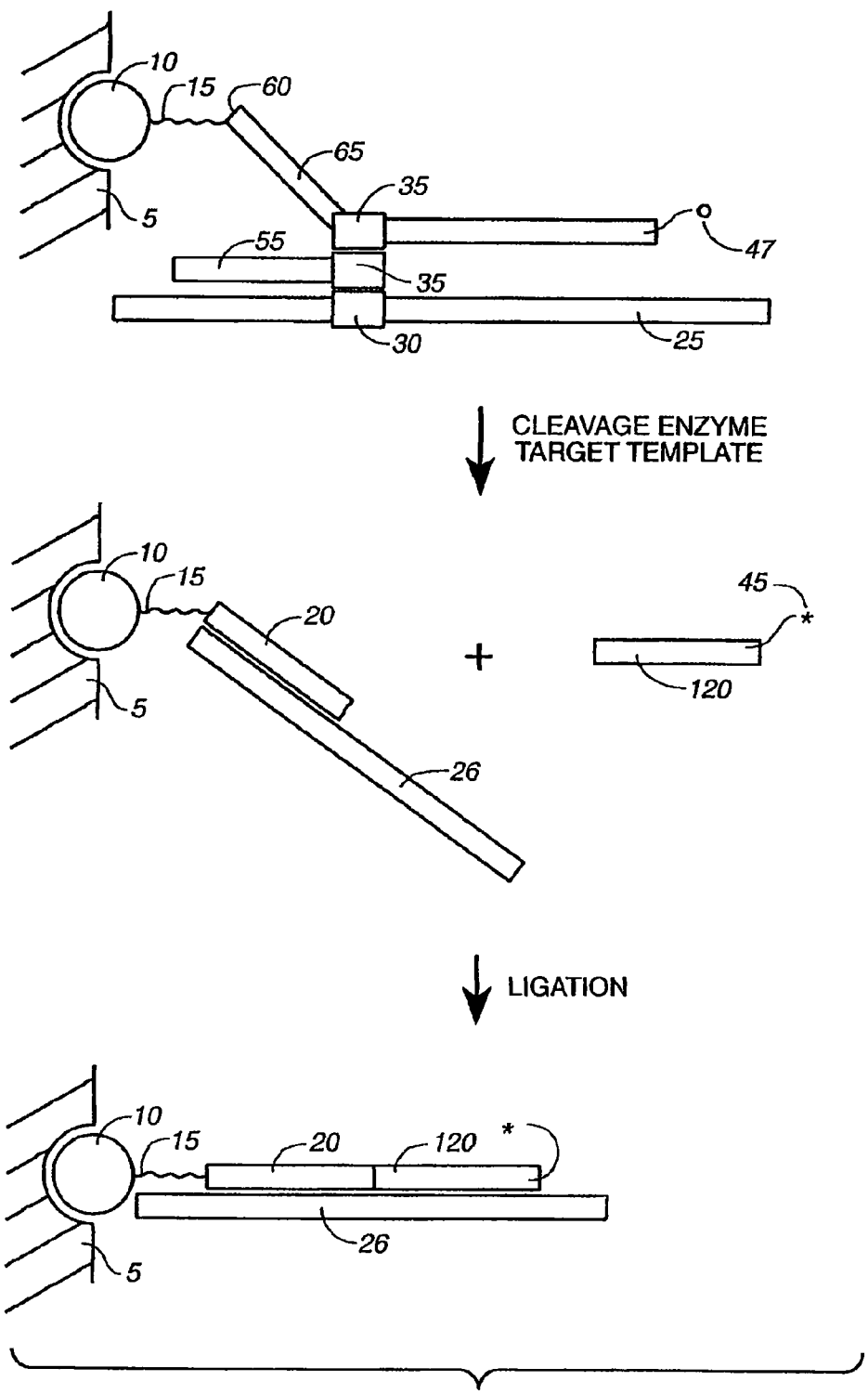
FIG._15B

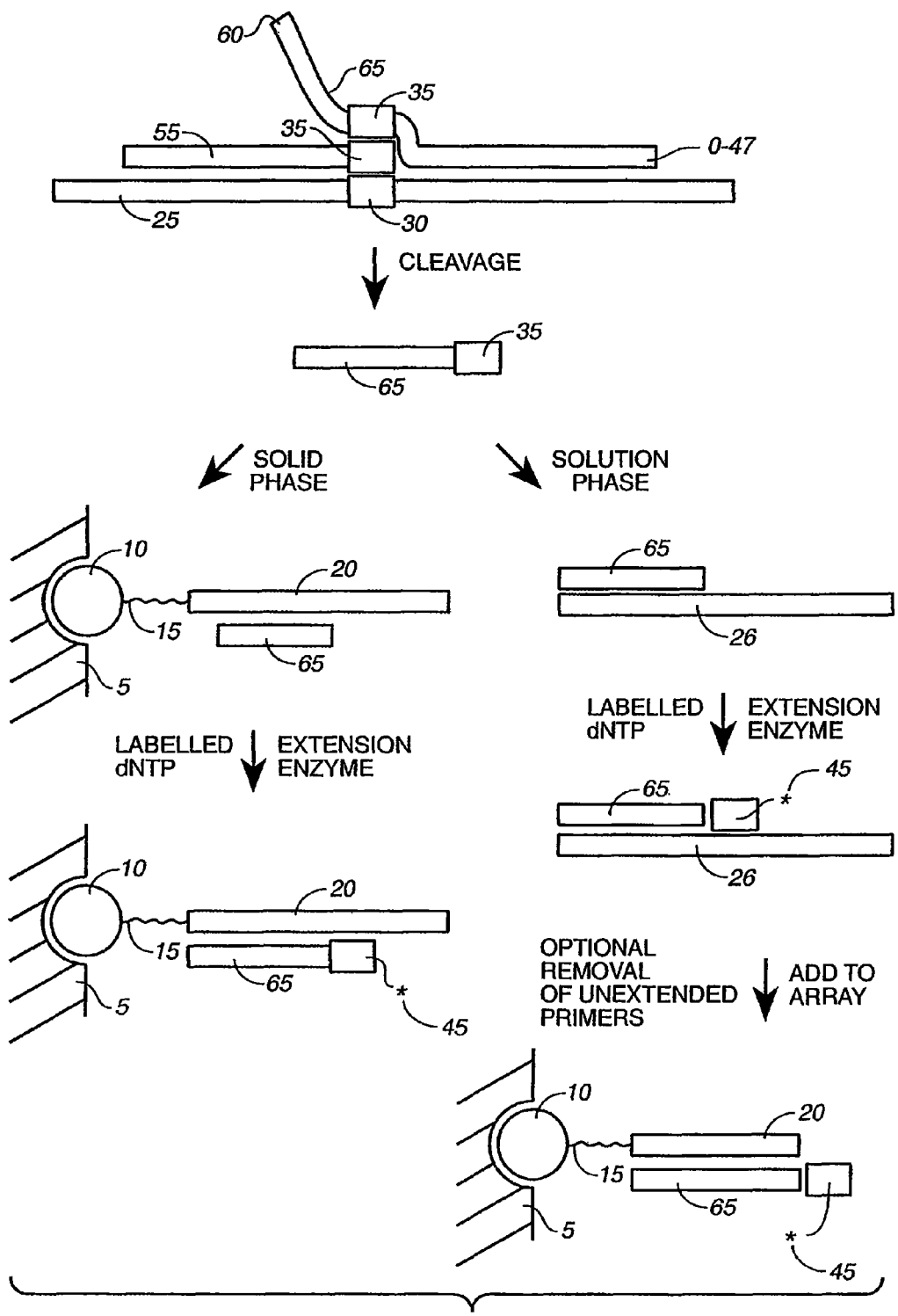
FIG._16A

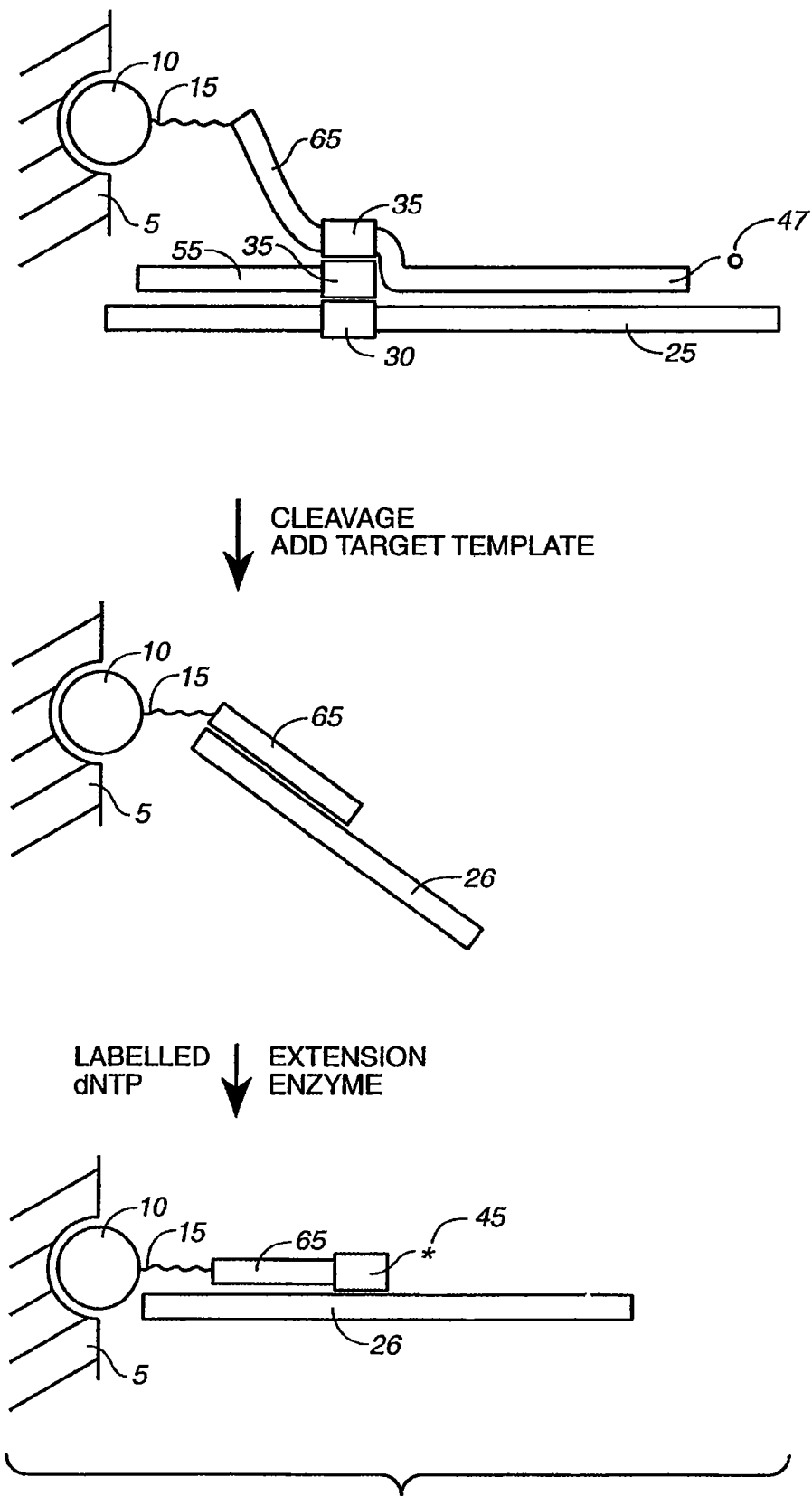
FIG._16B

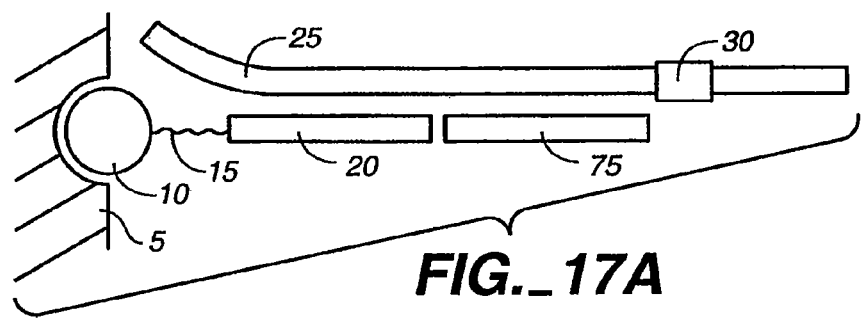
FIG._17A
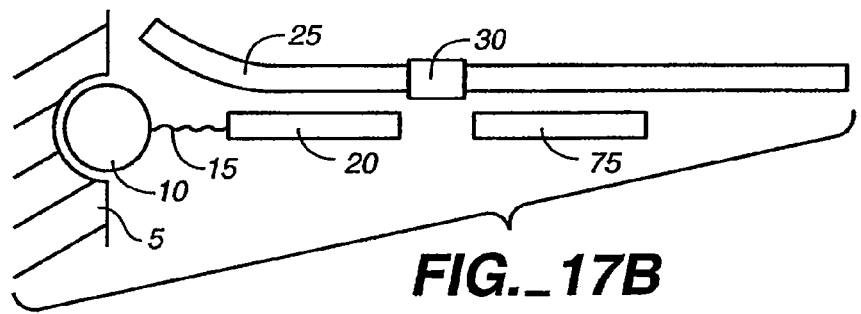
FIG._17B
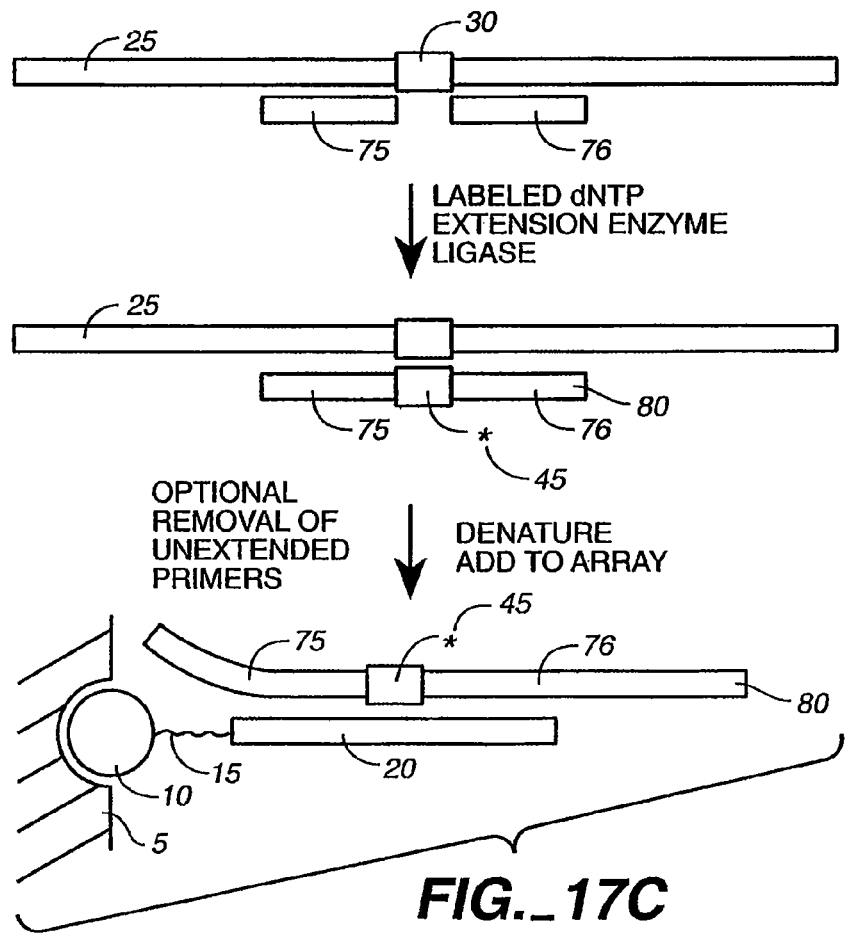
FIG._17C

DETECTION OF NUCLEIC ACID REACTIONS ON BEAD ARRAYS

This application is a continuation of Ser. No. 11/238,826, filed Sep. 28, 2005 now abandoned, which is a continuation of U.S. application Ser. No. 09/553,993, filed Apr. 20, 2000 now abandoned, which is a continuation of U.S. application Ser. No. 09/535,854, filed Mar. 27, 2000, now abandoned, which is a continuation-in-part of U.S. application Ser. No. 09/517,945, filed Mar. 3, 2000, which issued as U.S. Pat. No. 6,355,431, which is a continuation-in-part of U.S. application Ser. No. 09/513,362, filed Feb. 25, 2000 now abandoned, which is a continuation-in-part of U.S. application Ser. No. 09/425,633, filed Oct. 22, 1999, now abandoned, which is based on, and claims the benefit of, U.S. provisional application Ser. Nos. 60/161,148, filed Oct. 22, 1999; 60/160,927, filed Oct. 22, 1999; 60/160,917, filed Oct. 22, 1999; 60/135,051, filed May 20, 1999; 60/135,053, filed May 20, 1999; 60/135,123, filed May 20, 1999; and 60/130,089, filed Apr. 20, 1999, each of which is expressly incorporated herein by reference in their entirety.

FIELD OF THE INVENTION

The present invention is directed to methods and compositions for the use of microsphere arrays to detect and quantify a number of nucleic acid reactions. The invention finds use in genotyping, i.e. the determination of the sequence of nucleic acids, particularly alterations such as nucleotide substitutions (mismatches) and single nucleotide polymorphisms (SNPs). Similarly, the invention finds use in the detection and quantification of a nucleic acid target using a variety of amplification techniques, including both signal amplification and target amplification. The methods and compositions of the invention can be used in nucleic acid sequencing reactions as well. All applications can include the use of adapter sequences to allow for universal arrays.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48-51 (1993)). The requirement for sensitivity (i.e. low detection limits) has been greatly alleviated by the development of the polymerase chain reaction PCR) and other amplification technologies which allow researchers to amplify exponentially a specific nucleic acid sequence before analysis (for a review, see Abramson et al., Current Opinion in Biotechnology, 4:41-47 (1993)).

Sensitivity, i.e. detection limits, remain a significant obstacle in nucleic acid detection systems, and a variety of techniques have been developed to address this issue. Briefly, these techniques can be classified as either target amplification or signal amplification. Target amplification involves the amplification (i.e. replication) of the target sequence to be detected, resulting in a significant increase in the number of target molecules. Target amplification strategies include the polymerase chain reaction (PCR), strand displacement amplification (SDA), and nucleic acid sequence based amplification (NASBA).

Alternatively, rather than amplify the target, alternate techniques use the target as a template to replicate a signalling probe, allowing a small number of target molecules to result in a large number of signalling probes, that then can be detected. Signal amplification strategies include the ligase chain reaction (LCR), cycling probe technology (CPT), invasive cleavage techniques such as Invader™ technology, Q-Beta replicase (Q(3R) technology, and the, use of "amplification probes" such as "branched DNA" that result in multiple label probes binding to a single target sequence.

The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", allelic PCR (see Newton et al. Nucl. Acid Res. 17:2503 91989); "reverse transcriptase PCR" or "RT-PCR", "biotin capture PCR", "vectorette PCR". "panhandle PCR", and "PCR select cDNA, subtraction", among others.

Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

Nucleic acid sequence based amplification (NASBA) is generally described in U.S. Pat. No. 5,409,818 and "Profiting from Gene-based Diagnostics", CTB International Publishing Inc., N.J., 1996, both of which are incorporated by reference.

Cycling probe technology (CPT) is a nucleic acid detection system based on signal or probe amplification rather than target amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667, all of which are specifically incorporated herein by reference.

The oligonucleotide ligation assay (OLA; sometimes referred to as the ligation chain reaction (LCR)) involve the ligation of at least two smaller probes into a single long probe, using the target sequence as the template for the ligase. See generally U.S. Pat. Nos. 5,185,243, 5,679,524 and 5,573,907; EP 0 320 308 B1; EP 0 336 731 B1; EP 0 439 182 B1; WO 90/01069; WO 89112696; and WO 89/09835, all of which are incorporated by reference.

Invader™ technology is based on structure-specific polymerases that cleave nucleic acids in a site-specific manner. Two probes are used: an "invader" probe and a "signalling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

"Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) Nuc. Acids Res. 26:5073-5078; Barany, F. (1991) Proc. Natl. Acad. Sci. USA 88:189-193; and Lizardi et al. (1998) Nat. Genet. 19:225-232, all of which are incorporated by reference in their entirety.

"Branched DNA" signal amplification relies on the synthesis of branched nucleic acids, containing a multiplicity of nucleic acid "arms" that function to increase the amount of label that can be put onto one probe. This technology is generally described in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

Similarly, dendrimers of nucleic acids serve to vastly increase the amount of label that can be added to a single molecule, using a similar idea but different compositions. This technology is as described in U.S. Pat. No. 5,175,270 and Nilsen et al., J. Theor. Biol. 187:273 (1997), both of which are incorporated herein by reference.

Specificity, in contrast, remains a problem in many currently available gene probe assays. The extent of molecular complementarity between probe and target defines the specificity of the interaction. In a practical sense, the degree of similarity between the target and other sequences in the sample also has an impact on specificity. Variations in the concentrations of probes, of targets and of salts in the hybridization medium, in the reaction temperature, and in the length of the probe may alter or influence the specificity of the probe/target interaction.

it may be possible under some circumstances to distinguish targets with perfect complementarity from targets with mismatches; this is generally very difficult using traditional technology such as filter hybridization, in situ hybridization etc., since small variations in the reaction conditions will alter the hybridization, although this may not be a problem if appropriate mismatch controls are provided. New experimental techniques for mismatch detection with standard probes include DNA ligation assays where single point mismatches prevent ligation and probe digestion assays in which mismatches create sites for probe cleavage.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art.

There are a variety of particular techniques that are used to detect sequence, including mutations and SNPs. These include, but are not limited to, ligation based assays, cleavage based assays (mismatch and invasive cleavage such as Invader™), single base extension methods (see WO 92/15712, EP 0 371 437 B1, EP 0317 074 B1; Pastinen et al., Genome Res. 7:606-614 (1997); Syvänen, Clinica Chimica Acta 226:225-236 (1994); and WO 91/13075), and competitive probe analysis (e.g. competitive sequencing by hybridization; see below).

In addition, DNA sequencing is a crucial technology in biology today, as the rapid sequencing of genomes, including the human genome, is both a significant goal and a significant hurdle. Thus there is a significant need for robust, high-throughput methods. Traditionally, the most common method of DNA sequencing has been based on polyacrylamide gel fractionation to resolve a population of chain-terminated fragments (Sanger et al., Proc. Natl. Acad. Sci. USA 74:5463 (1977); Maxam & Gilbert). The population of fragments, terminated at each position in the DNA sequence, can be generated in a number of ways. Typically, DNA polymerase is used to incorporate dideoxynucleotides that serve as chain terminators.

Several alternative methods have been developed to increase the speed and ease of DNA sequencing. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others). Similarly, sequencing by synthesis is an alternative to gel-based sequencing. These methods add and read only one base (or at most a few bases, typically of the same type) prior to polymerization of the next base. This can be referred to as "time resolved" sequencing, to contrast from "gel-resolved" sequencing. Sequencing by synthesis has been described in U.S. Pat. No. 4,971,903 and Hyman, Anal. Biochem. 174:423 (1968); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996), Nyren et al., Anal. Biochem. 151:504 (1985). Detection of ATP sulfurylase activity is described in Karamohamed and Nyren, Anal. Biochem. 271:81 (1999). Sequencing using reversible chain terminating nucleotides is described in U.S. Pat. Nos. 5,902,723 and 5,547,839, and Canard and Arzumanov, Gene 11:1 (1994), and Dyatkina and Arzumanov, Nucleic Acids Symp Ser 18:117 (1987). Reversible chain termination with DNA ligase is described in U.S. Pat. No. 5,403,708. Time resolved sequencing is described in Johnson et al., Anal. Biochem. 136:192 (1984). Single molecule analysis is described in U.S. Pat. No. 5,795,782 and Elgen and Rigler, Proc. Natl. Acad Sci USA 91(13):5740 (1994), all of which are hereby expressly incorporated by reference in their entirety.

One promising sequencing by synthesis method is based on the detection of the pyrophosphate (PPi) released during the DNA polymerase reaction. As nucleotriphosphates are added to a growing nucleic acid chain, they release PPi. This release can be quantitatively measured by the conversion of PPi to ATP by the enzyme sulfurylase, and the subsequent production of visible light by firefly luciferase.

Several assay systems have been described that capitalize on this mechanism. See for example WO93/23564, WO 98/28440 and WO98/13523, all of which are expressly incorporated by reference. A preferred method is described in Ronaghi et al., Science 281:363 (1998). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase, luciferase, and optionally a nucleotide-degrading enzyme such as apyrase. A dNTP is only incorporated into the growing DNA strand if it is complementary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

In some cases the DNA template is associated with a solid support. To this end, there are a wide variety of known methods of attaching DNAs to solid supports. Recent work has focused on the attachment of binding ligands, including nucleic acid probes, to microspheres that are randomly distributed on a surface, including a fiber optic bundle, to form high density arrays. See for example PCTs US98/21193, PCT US99114387 and PCT US98/05025; WO98/50782; and U.S. Ser. Nos. 09/287,573, 09/151,877, 09/256,943, 09/316,154, 60/119,323, 09/315,584; all of which are expressly incorporated by reference.

An additional technique utilizes sequencing by hybridization. For example, sequencing by hybridization has been described (Drmanac et al., Genomics 4:114 (1989); U.S. Pat. Nos. 5,525,464; 5,202,231 and 5,695,940, among others, all of which are hereby expressly incorporated by reference in their entirety).

In addition, sequencing using mass spectrometry techniques has been described; see Koster et al., Nature Biotechnology 14:1123 (1996).

Finally, the use of adapter-type sequences that allow the use of universal arrays has been described in limited contexts; see for example Chee et al., Nucl. Acid Res. 19:3301 (1991); Shoemaker et al., Nature Genetics 14:450 (1998); Barany, F. (1991) Proc. Natl. Acad. Sci. USA 88:189-193; EP 0 799 897 A1; WO 97/31256, all of which are expressly incorporated by reference.

PCTs US98/21193, PCT US99/14387 and PCT US98105025; WO98/50782; and U.S. Ser. Nos. 09/287,573, 09/151,877, 09/256,943, 09/316,154, 60/119,323, 09/315, 584; all of which are expressly incorporated by reference, describe novel compositions utilizing substrates with microsphere arrays, which allow for novel detection methods of nucleic acid hybridization.

Accordingly, it is an object of the present invention to provide detection and quantification methods for a variety of nucleic acid reactions, including genotyping, amplification reactions and sequencing reactions, utilizing microsphere arrays.

SUMMARY OF THE INVENTION

In accordance with the above objects, the present invention provides methods of determining the identity of a nucleotide at a detection position in a target sequence. The methods comprise providing a hybridization complex comprising the target sequence and a capture probe covalently attached to a microsphere on a surface of a substrate. The methods comprise determining the nucleotide at the detection position. The hybridization complex can comprise the capture probe, a capture extender probe, and the target sequence. In addition, the target sequence may comprise exogeneous adapter sequences.

In an additional aspect, the method comprises contacting the microspheres with a plurality of detection probes each comprising a unique nucleotide at the readout position and a unique detectable label. The signal from at least one of the detectable labels is detected to identify the nucleotide at the detection position.

In an additional aspect, the detection probe does not contain detection label, but rather is identified based on its characteristic mass, for example via mass spectrometry. In addition, the detection probe comprises a unique label that is detected based on its characteristic mass.

In a further aspect, the invention provides methods wherein the target sequence comprises a first target domain directly 5' adjacent to the detection position. The hybridization complex comprises the target sequence, a capture probe and an extension primer hybridized to the first target domain of the target sequence. The determination step comprises contacting the microspheres with a polymerase enzyme, and a plurality of NTPs each comprising a covalently attached detectable label, under conditions whereby if one of the NTPs basepairs with the base at the detection position, the extension primer is extended by the enzyme to incorporate the label. As is known to those in the art, dNTPs and ddNTPs are the preferred substrates for DNA polymerases. NTPs are the preferred substrates for RNA polymerases. The base at the detection position is then identified.

In an additional aspect, the invention provides methods wherein the target sequence comprises a first target domain directly 5' adjacent to the detection position, wherein the capture probe serves as an extension primer and is hybridized to the first target domain of the target sequence. The determination step comprises contacting the microspheres with a polymerase enzyme, and a plurality of NTPs each comprising a covalently attached detectable label, under conditions whereby if one of the NTPs basepairs with the base at the detection position, the extension primer is extended by the enzyme to incorporate the label. The base at the detection position is thus identified.

In a further aspect, the invention provides methods wherein the target sequence comprises (5' to 3'), a first target domain comprising an overlap domain comprising at least a nucleotide in the detection position and a second target domain contiguous with the detection position. The hybridization complex comprises a first probe hybridized to the first target domain, and a second probe hybridized to the second target domain. The second probe comprises a detection sequence that does not hybridize with the target sequence, and a detectable label. If the second probe comprises a base that is perfectly complementary to the detection position a cleavage structure is formed. The method further comprises contacting the hybridization complex with a cleavage enzyme that will cleave the detection sequence from the signalling probe and then forming an assay complex with the detection sequence, a capture probe covalently attached to a microsphere on a surface of a substrate, and at least one label. The base et the detection position is thus identified.

In an additional aspect, the invention provides methods of determining the identification of a nucleotide at a detection position in a target sequence comprising a first target domain comprising the detection position and a second target domain adjacent to the detection position. The method comprises hybridizing a first ligation probe to the first target domain, and hybridizing a second ligation probe to the second target domain. If the second ligation probe comprises a base that is perfectly complementary to the detection position a ligation structure is formed. A ligation enzyme is provided that will ligate the first and the second ligation probes to form a ligated probe. An assay complex is formed with the ligated probe, a capture probe covalently attached to a microsphere on a surface of a substrate, and at least one label. The base at the detection position is thus identified.

In a further aspect, the present invention provides methods of sequencing a plurality of target nucleic acids. The methods comprise providing a plurality of hybridization complexes each comprising a target sequence and a sequencing primer that hybridizes to the first domain of the target sequence, the hybridization complexes are attached to a surface of a substrate. The methods comprise extending each of the primers by the addition of a first nucleotide to the first detection position using an enzyme to form an extended primer. The methods comprise detecting the release of pyrophosphate (PPi) to determine the type of the first nucleotide added onto the primers. In one aspect the hybridization complexes are attached to microspheres distributed on the surface. In an additional aspect the sequencing primers are attached to the surface. The hybridization complexes comprise the target sequence, the sequencing primer and a capture probe covalently attached to the surface. The hybridization complexes also comprise an adapter probe.

In an additional aspect, the method comprises extending the extended primer by the addition of a second nucleotide to the second detection position using an enzyme and detecting the release of pyrophosphate to determine the type of second nucleotide added onto the primers. In an additional aspect, the pyrophosphate is detected by contacting the pyrophosphate with a second enzyme that converts pyrophosphate into ATP, and detecting the ATP using a third enzyme. In one aspect, the second enzyme is sulfurylase and/or the third enzyme is luciferase.

In an additional aspect, the invention provides methods of sequencing a target nucleic acid comprising a first domain and an adjacent second domain, the second domain comprising a plurality of target positions. The method comprises providing a hybridization complex comprising the target sequence and a capture probe covalently attached to microspheres on a surface of a substrate and determining the identity of a plurality of bases at the target positions. The hybridization complex comprises the capture probe, an adapter probe, and the target sequence. In one aspect the sequencing primer is the capture probe.

In an additional aspect of the invention, the determining comprises providing a sequencing primer hybridized to the second domain, extending the primer by the addition of first nucleotide to the first detection position using a first enzyme to form an extended primer, detecting the release of pyrophosphate to determine the type of the first nucleotide added onto the primer, extending the primer by the addition of a second nucleotide to the second detection position using the enzyme, and detecting the release of pyrophosphate to determine the type of the second nucleotide added onto the primer. In an additional aspect pyrophosphate is detected by contacting the pyrophosphate with the second enzyme that converts pyrophosphate into ATP, and detecting the ATP using a third enzyme. In one aspect the second enzyme is sulfurylase and/or the third enzyme is luciferase.

In an additional aspect of the method for sequencing, the determining comprises providing a sequencing primer hybridized to the second domain, extending the primer by the addition of a first protected nucleotide using a first enzyme to form an extended primer, determining the identification of the first protected nucleotide, removing the protection group, adding a second protected nucleotide using the enzyme, and determining the identification of the second protected nucleotide.

In an additional aspect the invention provides a kit for nucleic acid sequencing comprising a composition comprising a substrate with a surface comprising discrete sites and a population of microspheres distributed on the sites, wherein the microspheres comprise capture probes. The kit also comprises an extension enzyme and dNTPs. The kit also comprises a second enzyme for the conversion of pyrophosphate to ATP and a third enzyme for the detection of ATP. In one aspect the dNTPs are labeled. In addition each dNTP comprises a different label.

In a further aspect, the present invention provides methods of detecting a target nucleic acid sequence comprising attaching a first adapter nucleic acid to a first target nucleic acid sequence to form a modified first target nucleic acid sequence, and contacting the modified first target nucleic acid sequence with an array as outlined herein. The presence of the modified first target nucleic acid sequence is then detected.

In an additional aspect, the methods further comprise attaching a second adapter nucleic acid to a second target nucleic acid sequence to form a modified second target nucleic acid sequence and contacting the modified second target nucleic acid sequence with the array.

In a further aspect, the invention provides methods of detecting a target nucleic acid sequence comprising hybridizing a first primer to a first portion of a target sequence, wherein the first primer further comprises an adapter sequence and hybridizing a second primer to a second portion of the target sequence. The first and second primers are ligated together to form a modified primer, and the adapter sequence of the modified primer is contacted with an array of the invention, to allow detection of the presence of the modified primer.

In an additional embodiment, the present invention provides a method for detecting a first target nucleic acid sequence. In one aspect the method comprises hybridizing at least a first primer nucleic acid to the first target sequence to form a first hybridization complex, contacting the first hybridization complex with a first enzyme to form a modified first primer nucleic acid, disassociating the first hybridization complex, contacting the modified first primer nucleic acid with an array comprising a substrate with a surface comprising discrete sites and a population of microspheres comprising at least a first subpopulation comprising a first capture probe such that the first capture probe and the modified primer form an assay complex, wherein the microspheres are distributed on the surface, and detecting the presence of the modified primer nucleic acid.

In addition the method further comprises hybridizing at least a second primer nucleic acid to a second target sequence that is substantially complementary to the first target sequence to form a second hybridization complex, contacting the second hybridization complex with the first enzyme to form modified second primer nucleic acid, disassociating the second hybridization complex and forming a second assay complex comprising the modified second primer nucleic acid and a second capture probe on a second subpopulation.

In an additional aspect of the invention the primer forms a circular probe following hybridization with the target nucleic acid to form a first hybridization complex and contacting the first hybridization complex with a first enzyme comprising a ligase such that the oligonucleotide ligation assay (OLA) occurs. This is followed by adding the second enzyme, a polymerase, such that the circular probe is amplified in a rolling circle amplification (RCA) assay.

In an additional aspect of the invention, the first enzyme comprises a DNA polymerase and the modification is an extension of the primer such that the polymerase chain reaction (PCR) occurs. In an additional aspect of the invention the first enzyme comprises a ligase and the modification comprises a ligation of the first primer which hybridizes to a first domain of the first target sequence, to a third primer which hybridizes to a second adjacent domain of the first target sequence such that the ligase chain reaction (LCR) occurs.

In an additional aspect of the invention, the first primer comprises a first probe sequence, a first scissile linkage and a second probe sequence, wherein the first enzyme will cleave the scissile linkage resulting in the separation of the first and second probe sequences and the disassociation of the first hybridization complex, leaving the first target sequence intact such that the cycling probe technology (CPT) reaction occurs.

In addition, wherein the first enzyme is a polymerase that extends the first primer and the modified first primer comprises a first newly synthesized strand, the method further comprises the addition of a second enzyme comprising a nicking enzyme that nicks the extended first primer leaving the first target sequence intact, and extending from the nick using the polymerase, and thereby displacing the first newly synthesized strand and generating a second newly synthesized strand such that strand displacement amplification (SBA) occurs.

In addition, wherein the first target sequence is an RNA target sequence, the first primer nucleic acid is a DNA primer comprising an RNA polymerase promoter, the first enzyme is a reverse-transcriptase that extends the first primer to form a first newly synthesized DNA strand, the method further comprises the addition of a second enzyme comprising an RNA degrading enzyme that degrades the first target sequence, the addition of a third primer that hybridizes to the first newly synthesized DNA strand, the addition of a third enzyme comprising a DNA polymerase that extends the third primer to form a second newly synthesized DNA strand, to form a newly synthesized DNA hybrid, the addition of a fourth enzyme comprising an RNA polymerase that recognizes the RNA polymerase promoter and generates at least one newly synthesized RNA strand from the DNA hybrid, such that nucleic acid sequence-based amplification (NASBA) occurs.

In addition, wherein the first primer is an invader primer, the method further comprises hybridizing a signalling primer to the target sequence, the enzyme comprises a structure-specific cleaving enzyme and the modification comprises a cleavage of said signalling primer, such that the invasive cleavage reaction occurs.

An additional aspect of the invention is a method for detecting a target nucleic acid sequence comprising hybridizing a first primer to a first target sequence to form a first hybridization complex, contacting the first hybridization complex with a first enzyme to extend the first primer to form a first newly synthesized strand and form a nucleic acid hybrid that comprises an RNA polymerase promoter, contacting the hybrid with an RNA polymerase that recognizes the RNA polymerase promoter and generates at least one newly synthesized RNA strand, contacting the newly synthesized RNA strand with an array comprising a substrate with a surface comprising discrete sites and a population of microspheres comprising at least a first subpopulation comprising a first capture probe; such that the first capture probe and the modified primer form an assay complex; wherein the microspheres are distributed on the surface and detecting the presence of the newly synthesized RNA strand.

In addition, when the target nucleic acid sequence is an RNA sequence, and prior to hybridizing a first primer to a first target sequence to form a first hybridization complex, method comprises hybridizing a second primer comprising an RNA polymerase promoter sequence to the RNA sequence to form a second hybridization complex, contacting the second hybridization complex with a second enzyme to extend the second primer to form a second newly synthesized strand and form a nucleic acid hybrid; and degrading the RNA sequence to leave the second newly synthesized strand as the first target sequence. In one aspect of the invention the degrading is done by the addition of an RNA degrading enzyme. In an additional aspect of the invention the degrading is done by RNA degrading activity of reverse transcriptase.

In addition, when the target nucleic acid sequence is a DNA sequence, and prior to hybridizing a first primer to a first target sequence to form a first hybridization complex, the method comprises hybridizing a second primer comprising an RNA polymerase promoter sequence to the DNA sequence to form a second hybridization complex, contacting the second hybridization complex with a second enzyme to extend the second primer to form a second newly synthesized strand and form a nucleic acid hybrid, and denaturing the nucleic acid hybrid such that the second newly synthesized strand is the first target sequence.

An additional aspect of the invention is a kit for the detection of a first target nucleic acid sequence. The kit comprises at least a first nucleic acid primer substantially complementary to at least a first domain of the target sequence, at least a first enzyme that will modify the first nucleic acid primer, and an array comprising a substrate with a surface comprising discrete sites, and a population of microspheres comprising at least a first and a second subpopulation, wherein each subpopulation comprises a bioactive agent, wherein the microspheres are distributed on the surface.

In an additional aspect of the invention, is a kit for the detection of a PCR reaction wherein the first enzyme is a thermostable DNA polymerase.

In an additional aspect of the invention, is a kit for the detection of a LCR reaction wherein the first enzyme is a ligase and the kit comprises a first nucleic acid primer substantially complementary to a first domain of the first target sequence and a third nucleic acid primer substantially complementary to a second adjacent domain of the first target sequence.

In an additional aspect of the invention, is a kit for the detection of a strand displacement amplification (SDA) reaction wherein the first enzyme is a polymerase and the kit further comprises a nicking enzyme.

In an additional aspect of the invention, is a kit for the detection of a NASBA reaction wherein the first enzyme is a reverse transcriptase, and the kit comprises a second enzyme comprising an RNA degrading enzyme, a third primer, a third enzyme comprising a DNA polymerase and a fourth enzyme comprising an RNA polymerase.

In an additional aspect of the invention, is a kit for the detection of an invasive cleavage reaction wherein the first enzyme is a structure-specific cleaving enzyme, and the kit comprises a signaling primer.

BRIEF DESCRIPTION OF THE DRAWINGS

FIGS. 1A, 1B and 1C depict three different embodiments for attaching a target sequence to an array. The solid support 5 has microsphere 10 with capture probe 20 linked via a linker 15. FIG. 1A depicts direct attachment; the capture probe 20 hybridizes to a first portion of the target sequence 25. FIG. 1B depicts the use of a capture extender probe 30 that has a first portion that hybridizes to the capture probe 20 and a second portion that hybridizes to a first domain of the target sequence 25. FIG. 1C shows the use of an adapter sequence 35, that has been added to the target sequence, for example during an amplification reaction as outlined herein.

FIGS. 2A and 2B depict two preferred embodiments of SBE amplification. FIG. 2A shows extension primer 40 hybridized to the target sequence 25. Upon addition of the extension enzyme and labelled nucleotides, the extension primer is modified to form a labelled primer 41. The reaction can be repeated and then the labelled primer is added to the array as above. FIG. 2B depicts the same reaction but using adapter sequences.

FIGS. 3A and 3B depict two preferred embodiments of OLA amplification. FIG. 3A depicts a first ligation probe 45 and a second ligation probe 50 with a label 55. Upon addition of the ligase, the probes are ligated. The reaction can be repeated and then the ligated primer is added to the array as above. FIG. 3B depicts the same reaction but using adapter sequences.

FIG. 4 depicts a preferred embodiment of the invasive cleavage reaction. In this embodiment, the signaling probe 65 comprises two portions, a detection sequence 67 and a signaling portion 66. The signaling portion can serve as an adapter sequence. In addition, the signaling portion generally comprises the label 55, although as will be appreciated by those in the art, the label may be on the detection sequence as well. In addition, for optional removal of the uncleaved probes, a capture tag 60 may also be used. Upon addition of the enzyme, the structure is cleaved, releasing the signaling portion 66. The reaction can be repeated and then the signaling portion is added to the array as above.

FIGS. 5A and 5B depict two preferred embodiments of CPT amplification. A CPT primer 70 comprising a label 55, a first probe sequence 71 and a second probe sequence 73, separated by a scissile linkage 72, and optionally comprising a capture tag 60, is hybridized to the target sequence 25. Upon addition of the enzyme, the scissile linkage is cleaved. The reaction can be repeated and then the probe sequence comprising the label is added to the array as above. FIG. 5B depicts the same reaction but using adapter sequences.

FIG. 6 depicts OLA/RCA amplification using a single "padlock probe" 57. The padlock probe is hybridized with a target sequence 25. When the probe 57 is complementary to the target sequence 26, ligation of the probe termini occurs forming a circular probe 28. When the probe 57 is not complementary to the target sequence 27, ligation does not occur. Addition of polymerase and nucleotides to the circular probe results amplification of the probe 58. Cleavage of the amplified probe 58 yields fragments 59 that hybridize with an identifier probe 21 immobilized on a microsphere 10.

FIG. 7 depicts an alternative method of OLA/RCA. An immobilized first OLA primer 45 is hybridized with a target sequence 25 and a second OLA primer 50. Following the addition of ligase, the first and second OLA primers are ligated to form a ligated oligonucleotide 56. Following denaturation to remove the target nucleic acid, the immobilized ligated oligonucleotide is distributed on an array. An RCA probe 57 and polymerase are added to the array resulting in amplification of the circular RCA probe 58.

FIGS. 8A, 8B, 8C, 8D and 8E schematically depict the use of readout probes for genotyping. FIG. 8A shows a "sandwich" format. Substrate 5 has a discrete site with a microsphere 10 comprising a capture probe 20 attached via a linker 15. The target sequence 25 has a first domain that hybridizes to the capture probe 20 and a second domain comprising a detection position 30 that hybridizes to a readout probe 40 with readout position 35. As will be appreciated by those in the art, FIG. 8A depicts a single detection position; however, depending on the system, a plurality of different probes can hybridize to different target domains; hence n is an integer of 1 or greater. FIG. 8B depicts the use of a capture probe 20 that also serves as a readout probe. FIG. 8C depicts the use of an adapter probe 100 that binds to both the capture probe 20 and the target sequence 25. As will be appreciated by those in the art, the figure depicts that the capture probe 20 and target sequence 25 bind adjacently and as such may be ligated; however, as will be appreciated by those in the art, there may be a "gap" of one or more nucleotides. FIG. 8D depicts a solution based assay. Two readout probes 40, each with a different readout position (35 and 36) and different labels (45 and 46) are added to target sequence 25 with detection position 35, to form a hybridization complex with the match probe. This is added to the array; FIG. 8D depicts the use of a capture probe 20 that directly hybridizes to a first domain of the target sequence, although other attachments may be done. FIG. 8E depicts the direct attachment of the target sequence to the array.

FIGS. 9A, 9B, 9C, 9D, 9E, 9F and 9G depict preferred embodiments for SBE genotyping. FIG. 9A depicts a "sandwich" assay, in which substrate 5 has a discrete site with a microsphere 10 comprising a capture probe 20 attached via a linker 15. The target sequence 25 has a first domain that hybridizes to the capture probe 20 and a second domain comprising a detection position 30 that hybridizes to an extension primer 50. As will be appreciated by those in the art, FIG. 9A depicts a single detection position; however, depending on the system, a plurality of different primers can hybridize to different target domains; hence n is an integer of 1 or greater. In addition, the first domain of the target sequence may be an adapter sequence. FIG. 9B depicts the use of a capture probe 20 that also serves as an extension primer. FIG. 9C depicts the solution reaction. FIG. 9D depicts the use of a capture extender probe 100, that has a first domain that will hybridize to the capture probe 20 and a second domain that will hybridize to a first domain of the target sequence 25. FIG. 9E depicts the addition of a ligation step prior to extension of the extension probe. FIG. 9F depicts the addition of a ligation step after the extension of the extension probe. FIG. 9G depicts the SBE solution reaction followed by hybridization of the product of the reaction to the bead array to capture an adapter sequence.

FIGS. 10A, 10B, 10C, 10D and 10E depict some of the OLA genotyping embodiments of the reaction. FIG. 10A depicts the solution reaction, wherein the target sequence 25 with a detection position 30 hybridizes to the first ligation probe 75 with readout position 35 and second probe 76 with a detectable label 45. As will be appreciated by those in the art, the second ligation probe could also contain the readout position. The addition of a ligase forms a ligated probe 80, that can then be added to the array with a capture probe 20. FIG. 10B depicts an "on bead" assay, wherein the capture probe 20 serves as the first ligation probe. FIG. 10C depicts a sandwich assay, using a capture probe 20 that hybridizes to a first portion of the target sequence 25 (which may be an endogeneous sequence or an exogenous adapter sequence) and ligation probes 75 and 76 that hybridize to a second portion of the target sequence comprising the detection position 30. FIG. 10D depicts the use of a capture extender probe 100. FIG. 10E depicts a solution based assay with the use of an adapter sequence 110. FIGS. 11A, 11B and 11C depict the SPOLA reaction for genotyping. In FIG. 11A, two ligation probes are hybridized to a target sequence. As will be appreciated by those in the art, this system requires that the two ligation probes be attached at different ends, i.e. one at the 5' end and one at the 3' end. One of the ligation probes is attached via a cleavable linker. Upon formation of the assay complex and the addition of a ligase, the two probes will efficiently covalently couple the two ligation probes if perfect complementarity at the junction exists. In FIG. 11B, the resulting ligation difference between correctly matched probes and imperfect probes is shown. FIG. 11C shows that subsequent cleavage of the cleavable linker produces a reactive group, in this case an amine, that may be subsequently labeled as outlined herein. Alternatively, cleavage may leave an upstream oligo with a detectable label. If not ligated, this labeled oligo can be washed away.

FIGS. 12A and 12B depict two cleavage reactions for genotyping. FIG. 12A depicts a loss of signal assay, wherein a label 45 is cleaved off due to the discrimination of the cleavage enzyme such as a restriction endonuclease or resolvase type enzyme to allow single base mismatch discrimination. FIG. 12B depicts the use of a quencher 46.

FIGS. 13A, 13B, 13C, 13D, and 13E depict the use of invasive cleavage to determine the identity of the nucleotide at the detection position. FIGS. 13A and 13B depict a loss of signal assay. FIG. 13A depicts the invader probe 55 with readout position 35 hybridized to the target sequence 25 which is attached via a capture probe 20 to the surface. The signal probe 60 with readout position 35, detectable label 45 and detection sequence 65 also binds to the target sequence 25; the two probes form a cleavage structure. If the two readout positions 35 are capable of basepairing to the detection position 30 the addition of a structure-specific cleavage enzyme releases the detection sequence 65 and consequently the label 45, leading to a loss of signal. FIG. 13B is the same, except that the capture probe 20 also serves as the invader probe. FIG. 13C depicts a solution reaction, wherein the signalling probe can comprise a capture tag 70 to facilitate the removal of uncleaved signal probes. The addition of the cleaved signal probe (e.g. the detection sequence 65) with its associated label 45 results in detection. FIG. 13D depicts a solution based assay using a label probe 120. FIG. 13E depicts a preferred embodiment of an invasive cleavage reaction that utilizes a fluorophore-quencher reaction. FIG. 13E has the 3' end of the signal probe 60 is attached to the bead 10 and comprises a label 45 and a quencher 46. Upon formation of the assay complex and subsequent cleavage, the quencher 46 is removed, leaving the fluorophore 45.

FIGS. 14A, 14B, 14C and 14D depict genotyping assays based on the novel combination of competitive hybridization and extension. FIGS. 14A, 14B and 14C depict solution based assays. After hybridization of the extension probe 50 with a match base at the readout position 35, an extension enzyme and dNTP is added, wherein the dNTP comprises a blocking moiety (to facilitate removal of unextended primers) or a hapten to allow purification of extended primer, i.e. biotin, DNP, fluorescein, etc. FIG. 14B depicts the same reaction with the use of an adapter sequence 90; in this embodiment, the same adapter sequence 90 may be used for each readout probe for an allele. FIG. 14C depicts the use of different adapter sequences 90 for each readout probe; in this embodiment, unreacted primers need not be removed, although they may be. FIG. 14D depicts a solid phase reaction, wherein the dNTP added in the position adjacent to the readout position 35 is labeled.

FIGS. 15A and 15B depict genotyping assays based on the novel combination of invasive cleavage and ligation reactions. FIG. 15A is a solution reaction, with the signalling probe 60 comprising a detection sequence 65 with a detectable label 45. After hybridization with the target sequence 25 and cleavage, the free detection sequence can bind to an array (depicted herein as a bead array, although any nucleic acid array can be used), using a capture probe 20 and a template target sequence 26 for the ligation reaction. In the absence of ligation, the signalling probe is washed away. FIG. 15B depicts a solid phase assay. In this embodiment, the 5' end of the signalling probe is attached to the array (again, depicted herein as a bead array, although any nucleic acid array can be used), and a blocking moiety is used at the 3' end. After cleavage, a free 3 end is generated, that can then be used for ligation using a template target 26. As will be appreciated by those in the art, the orientation of this may be switched, such that the 3' end of the signalling probe 60 is attached, and a free 5' end is generated for the ligation reaction.

FIGS. 16A and 16B depict genotyping assays based on the novel combination of invasive cleavage and extension reactions. FIG. 16A depicts an initial solution based assay, using a signalling probe with a blocked 3' end. After cleavage, the detection sequence can be added to an array and a template target added, followed by extension to add a detectable label. Alternatively, the extension can also happen in solution, using a template target 26, followed by addition of the extended probe to the array. FIG. 16B depicts the solid phase reaction; as above, either the 3' or the 5' end can be attached. By using a blocking moiety 47, only the newly cleaved ends may be extended.

FIGS. 17A, 17B and 17C depict three configurations of the combination of ligation and extension ("Genetic Bit" analysis) for genotyping. FIG. 17A depicts a reaction wherein the capture probe 20 and the extension probe serve as two ligation probes, and hybridize adjacently to the target sequence, such that an additional ligation step may be done. A labeled nucleotide is added at the readout position. FIG. 17B depicts a preferred embodiment, wherein the ligation probes (one of which is the capture probe 20) are separated by the detection position 30. The addition of a labeled dNTP, extension enzyme and ligase thus serve to detect the readout position. FIG. 17C depicts the solution phase assay. As will be appreciated by those in the art, an extra level of specificity is added if the capture probe 20 spans the ligated probe 80.

DETAILED DESCRIPTION OF THE INVENTION

Figure 9E:
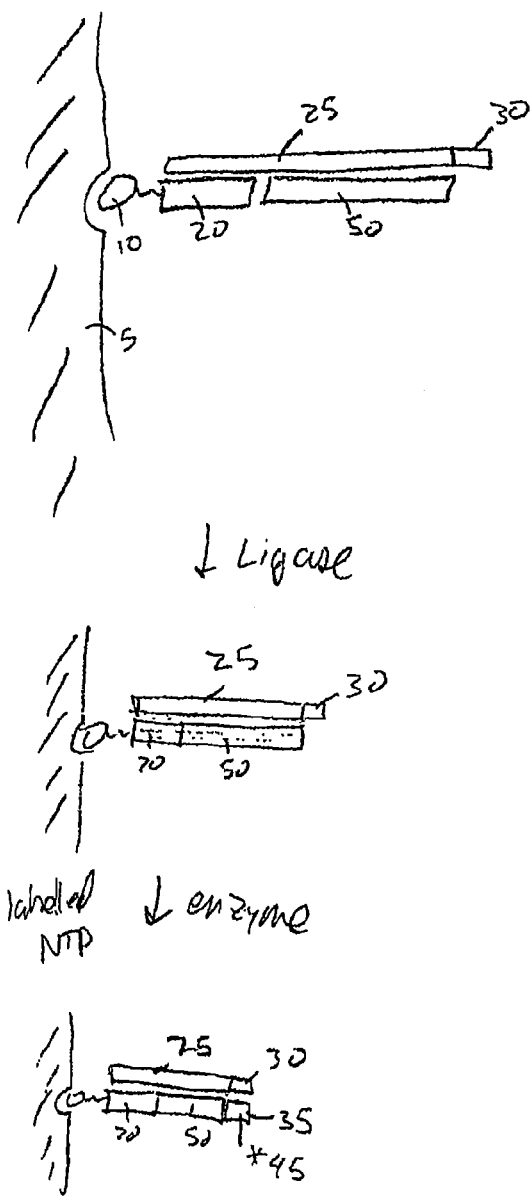

The present invention is directed to the detection and quantification of a variety of nucleic acid reactions, particularly using microsphere arrays. In particular, the invention relates to the detection of amplification, genotyping, and sequencing reactions. In addition, the invention can be utilized with adapter sequences to create universal arrays.

Accordingly, the present invention provides compositions and methods for detecting and/or quantifying the products of nucleic acid reactions, such as target nucleic acid sequences, in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples; purified samples, such as purified genomic DNA, RNA, proteins, etc.; raw samples (bacteria, virus, genomic DNA, etc. As will be appreciated by those in the art, virtually any experimental manipulation may have been done on the sample.

The present invention provides compositions and methods for detecting the presence or absence of target nucleic acid sequences in a sample. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., *Chemica Scripta* 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al:, Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997, page 35. All of these references are hereby expressly incorporated by reference. These modifications of the ribose-phosphate backbone may be done to facilitate the addition of labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The compositions and methods of the invention are directed to the detection of target sequences. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of a reaction such as a detection sequence from an invasive cleavage reaction, a ligated probe from an OLA reaction, an extended probe from a PCR or SBE reaction, etc. Thus, for example, a target sequence from a sample is amplified to produce a secondary target that is detected; alternatively, an amplification step is done using a signal probe that is amplified, again producing a secondary target that is detected. The target sequence may be any length, with the understanding that longer sequences are more specific. As will be appreciated by those in the art, the complementary target sequence may take many forms. For example, it may be contained within a larger nucleic acid sequence, i.e. all or part of a gene or mRNA; a restriction fragment of a plasmid or genomic DNA, among others. As is outlined more fully below, probes are made to hybridize to target sequences to determine the presence, absence or quantity of a target sequence in a sample. Generally speaking, this term will be understood by those skilled in the art. The target sequence may also be comprised of different target domains; for example, in "sandwich" type assays as outlined below, a first target domain of the sample target sequence may hybridize to a capture probe or a portion of capture extender probe, a second target domain may hybridize to a portion of an amplifier probe, a label probe, or a different capture or capture extender probe, etc. In addition, the target domains may be adjacent (i.e. contiguous) or separated. For example, when OLA techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below. The terms "first' and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain. in addition, as will be appreciated by those in the art, the probes on the surface of the array (e.g.

attached to the microspheres) may be attached in either orientation, either such that they have a free 3' end or a free 5' end; in some embodiments, the probes can be attached at one or more internal positions, or at both ends.

If required, the target sequence is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques may also be used.

As outlined herein; the invention provides a number of different primers and probes. By "primer nucleic acid" herein is meant a probe nucleic acid that will hybridize to some portion, i.e. a domain, of the target sequence. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions. A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The size of the primer nucleic acid may vary, as will be appreciated by those in the art, in general varying from 5 to 500 nucleotides in length, with primers of between 10 and 100 being preferred, between 15 and 50 being particularly preferred, and from 10 to 35 being especially preferred, depending on the use and amplification technique. In addition, the different amplification techniques may have further requirements of the primers, as is more fully described below.

In addition, as outlined herein, a variety of labeling techniques can be done.

Labeling Techniques

In general, either direct or indirect detection of the target products can be done. "Direct" detection as used in this context, as for the other reactions outlined herein, requires the incorporation of a label, in this case a detectable label, preferably an optical label such as a fluorophore, into the target sequence, with detection proceeding as outlined below. In this embodiment, the label(s) may be incorporated in a variety of ways: (1) the primers comprise the label(s), for example attached to the base, a ribose, a phosphate, or to analogous structures in a nucleic acid analog; (2) modified nucleosides are used that are modified at either the base or the ribose (or to analogous structures in a nucleic acid analog) with the label(s); these label-modified nucleosides are then converted to the triphosphate form and are incorporated into a newly synthesized strand by a polymerase; (3) modified nucleotides are used that comprise a functional group that can be used to add a detectable label; (4) modified primers are used that comprise a functional group that can be used to add a detectable label or (5) a label probe that is directly labeled and hybridizes to a portion of the target sequence can be used. Any of these methods result in a newly synthesized strand or reaction product that comprises labels, that can be directly detected as outlined below.

Thus, the modified strands comprise a detection label. By "detection label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as SBE, OLA, invasive cleavage reactions, etc; in addition, these techniques may be used with many of the other techniques described herein. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$-$10^{-9}$ $M^{-1}$ being preferred and less than about $10^{-7}$-$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

For removal of unextended primers, it is preferred that the other half of the binding pair is attached to a solid support. In this embodiment, the solid support may be any as described herein for substrates and microspheres, and the form is preferably microspheres as well; for example, a preferred embodiment utilizes magnetic beads that can be easily introduced to the sample and easily removed, although any affinity chromatography formats may be used as well. Standard methods are used to attach the binding partner to the solid support, and can include direct or indirect attachment methods. For example, biotin labeled antibodies to fluorophores can be attached to streptavidin coated magnetic beads.

Thus, in this embodiment, the extended primers comprise a binding partner that is contacted with its binding partner under conditions wherein the extended or reacted primers are separated from the unextended or unreacted primers. These modified primers can then be added to the array comprising capture probes as described herein.

Removal of Unextended Primers

In a preferred embodiment, it is desirable to remove the unextended or unreacted primers from the assay mixture, and particularly from the array, as unextended primers will compete with the extended (labeled) primers in binding to capture probes, thereby diminishing the signal. The concentration of the unextended primers relative to the extended primer may be relatively high, since a large excess of primer is usually required to generate efficient primer annealing. Accordingly, a number of different techniques may be used to facilitate the removal of unextended primers. While the discussion below applies specifically to SBE, these techniques may be used in any of the methods described herein.

in a preferred embodiment, the NTPs (or, in the case of other methods, one or more of the probes) comprise a secondary detectable label that can be used to separate extended and non-extended primers. As outlined above, detection labels may be primary labels (i.e. directly detectable) or secondary labels (indirectly detectable). A secondary label is one that is indirectly detected; for example, a secondary label can bind or react with a primary label for detection, or may allow the separation of the compound comprising the secondary label from unlabeled materials, etc. Secondary labels find particular use in systems requiring separation of labeled and unlabeled probes, such as SBE, OLA, invasive cleavage, etc. reactions; in addition, these techniques may be used with many of the other techniques described herein. Secondary labels include, but are not limited to, one of a binding partner pair; chemically modifiable moieties; nuclease inhibitors, etc.

In a preferred embodiment, the secondary label is a binding partner pair as outlined above. In a preferred embodiment, the binding partner pair comprises biotin or imino-biotin and streptavidin. Imino-biotin is particularly preferred when the methods require the later separation of the pair, as imino-biotin disassociates from streptavidin in pH 4.0 buffer while biotin requires harsh denaturants (e.g. 6 M guanidinium HCI, pH 1.5 or 90% formamide at 95° C.).

In addition, the use of streptavidin/biotin systems can be used to separate unreacted and reacted probes (for example in SBE, invasive cleavage, etc.). For example, the addition of streptavidin to a nucleic acid greatly increases its size, as well as changes its physical properties, to allow more efficient separation techniques. For example, the mixtures can be size fractionated by exclusion chromatography, affinity chromatography, filtration or differential precipitation. Alternatively, an 3' exonuclease may be added to a mixture of 3' labeled biotin/streptavidin; only the unreacted oligonucleotides will be degraded. Following exonuclease treatment, the exonuclease and the streptavidin can be degraded using a protease such as proteinase K. The surviving nucleic acids (i.e. those that were biotinylated) are then hybridized to the array.

In a preferred embodiment, the binding partner pair comprises a primary detection label (attached to the NTP and therefore to the extended primer) and an antibody that will specifically bind to the primary detection label.

In this embodiment, it is preferred that the other half of the binding pair is attached to a solid support. In this embodiment, the solid support may be any as described herein for substrates and microspheres, and the form is preferably microspheres as well; for example, a preferred embodiment utilizes magnetic beads that can be easily introduced to the sample and easily removed, although any affinity chromatography formats may be used as well. Standard methods are used to attach the binding partner to the solid support, and can include direct or indirect attachment methods. For example, biotin labeled antibodies to fluorophores can be attached to streptavidin coated magnetic beads.

Thus, in this embodiment, the extended primers comprise a binding member that is contacted with its binding partner under conditions wherein the extended primers are separated from the unextended primers. These extended primers can then be added to the array comprising capture probes as described herein.

In a preferred embodiment, the secondary label is a chemically modifiable moiety. In this embodiment, labels comprising reactive functional groups are incorporated into the nucleic acid.

In a preferred embodiment, the secondary label is a nuclease inhibitor. In this embodiment, the chain-terminating NTPs are chosen to render extended primers resistant to nucleases, such as 3'-exonucleases. Addition of an exonuclease will digest the non-extended primers leaving only the extended primers to bind to the capture probes on the array. This may also be done with OLA, wherein the ligated probe will be protected but the unprotected ligation probe will be digested.

In this embodiment, suitable 3'-exonucleases include, but are not limited to, exo I, exo III, exo VII, etc.

The present invention provides a variety of amplification reactions that can be detected using the arrays of the invention.

Amplification Reactions

In this embodiment, the invention provides compositions and methods for the detection (and optionally quantification) of products of nucleic acid amplification reactions, using bead arrays for detection of the amplification products. Suitable amplification methods include both target amplification and signal amplification and include, but are not limited to, polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA), and invasive cleavage technology. All of these methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a target nucleic acid is added to a reaction mixture that comprises the necessary amplification components, and a modified primer is formed.

In general, the modified primer comprises a detectable label, such as a fluorescent label, which is either incorporated by the enzyme or present on the original primer. As required, the unreacted primers are removed, in a variety of ways, as will be appreciated by those in the art and outlined herein. The hybridization complex is then disassociated, and the modified primer is detected and optionally quantitated by a microsphere array. In some cases, the newly modified primer serves as a target sequence for a secondary reaction, which then produces a number of amplified strands, which can be detected as outlined herein.

Accordingly, the reaction starts with the addition of a primer nucleic acid to the target sequence which forms a hybridization complex. Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identity of the enzyme will depend on the amplification technique used, as is more fully outlined below. Similarly, the modification will depend on the amplification technique, as outlined below.

Once the enzyme has modified the primer to form a modified primer, the hybridization complex is disassociated. In one aspect, dissociation is by modification of the assay conditions. In another aspect, the modified primer no longer hybridizes to the target nucleic acid and dissociates. Either one or both of these aspects can be employed in signal and target amplification reactions as described below. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred.

After a suitable time of amplification, unreacted primers are removed, in a variety of ways, as will be appreciated by those in the art and described below, and the hybridization complex is disassociated. In general, the modified primer comprises a detectable label, such as a fluorescent label, which is either incorporated by the enzyme or present on the original primer, and the modified primer is added to a microsphere array such as is generally described in U.S. Ser. Nos. 09/189,543; 08/944,850; 09/033,462; 09/287,573; 09/151,877; 09/187,289 and 09/256,943; and PCT applications US98/09163 and US99/14387; US98/21193; US99/04473 and US98/05025, all of which are hereby incorporated by reference. The microsphere array comprises subpopulations of microspheres that comprise capture probes that will hybridize to the modified primers. Detection proceeds via detection of the label as an indication of the presence, absence or amount of the target sequence, as is more fully outlined below.

Target Amplification

In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), transcription mediated amplification (TMA) and nucleic acid sequence based amplification (NASBA).

Polymerase Chain Reaction Amplification

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-POR", "PCR single strand conformational polymorphism" or "PCR-SSCP", "reverse transcriptase PCR" qr "RT-PCR", "biotin capture PCR", "vectorette PCR", "panhandle PCR", and "PCR select cDNA subtraction", "allele-specific PCR", among others. In some embodiments, PCR is not preferred.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostable polymerase such as Taq I polymerase and thermal cycling.

Accordingly, the PCR reaction requires at least one PCR primer, a polymerase, and a set of dNTPs. As outlined herein, the primers may comprise the label, or one or more of the dNTPs may comprise a label.

In general, as is more fully outlined below, the capture probes on the beads of the array are designed to be substantially complementary to the extended part of the primer; that is, unextended primers will not bind to the capture probes. Alternatively, as further described below, unreacted probes may be removed prior to addition to the array.

Strand Displacement Amplification (SDA)

In a preferred embodiment, the target amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In general, SDA may be described as follows. A single stranded target nucleic acid, usually a DNA target sequence, is contacted with an SDA primer. An "SDA primer" generally has a length of 25-100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target sequence. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2'deoxyadenosine 5'—O-(1-thiotriphosphate), 5-methyldeoxycytidine 5'-triphosphate, 2'-deoxyuridine 5'-triphosphate, and 7-deaza-2'-deoxyguanosine 5'-triphosphate. In addition, the substitution of the dNTP may occur after Incorporation into a newly synthesized strand; for example, a methylase may be used to add methyl groups to the synthesized strand. In addition, if all the nucleotides are substituted, the polymerase may have 5'-3' exonuclease activity. However, if less than all the nucleotides are substituted, the polymerase preferably lacks 5'-3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincI, HindIII, AvaI, Fnu4HI, TthIIII, NcII, BstXI, BamHlI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'-•3', thereby creating another newly synthesized strand. The polymerase chosen should be able to initiate 5',3' polymerization at a nick site, should also displace the polymerized strand downstream from the nick, and should lack 5'-'3' exonuclease activity (this may be additionally accomplished by the addition of a blocking agent). Thus, suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified. Again, as outlined above for PCR, preferred embodiments utilize capture probes complementary to the newly synthesized portion of the primer, rather than the primer region, to allow unextended primers to be removed.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, as for most of the amplification techniques described herein, a second amplification reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands.

Nucleic Acid Sequence Based Amplification (NASBA) and Transcription Mediated Amplification (TMA)

In a preferred embodiment, the target amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In general, these techniques may be described as follows. A single stranded target nucleic acid, usually an RNA target sequence (sometimes referred to herein as "the first target sequence" or "the first template"), is contacted with a first primer, generally referred to herein as a "NASBA primer" (although "TMA primer" is also suitable). Starting with a DNA target sequence is described below. These primers generally have a length of 25-100 nucleotides, with NASBA primers of approximately 50-75 nucleotides being preferred. The first primer is preferably a DNA primer that has at its 3' end a sequence that is substantially complementary to the 3' end of the first template. The first primer also has an RNA polymerase promoter at its 5' end (or its complement (antisense), depending on the configuration of the system). The first primer is then hybridized to the first template to form a first hybridization complex. The reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMV RT") and the Moloney murine leukemia virus RT. When the amplification reaction is TMA, the reverse transcriptase enzyme further comprises a RNA degrading activity as outlined below.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from *E. coli* and calf thymus.

The ribonuclease activity degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a. template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage cpII, *Salmonella* phage sp6, or Pseudomonase phage gh-1.

In some embodiments, TMA and NASBA are used with starting DNA target sequences. In this embodiment, it is necessary to utilize the first primer comprising the RNA polymerase promoter and a DNA polymerase enzyme to generate a double stranded DNA hybrid with the newly synthesized strand comprising the promoter sequence. The hybrid is then denatured and the second primer added.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

Accordingly, the TMA reaction requires, in no particular order, a first TMA primer, a second TMA primer comprising an antisense sequence of an RNA polymerase promoter, an RNA polymerase that recognizes the promoter, a reverse transcriptase with RNA degrading activity, a DNA polymerase, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

As outlined herein, the detection of the newly synthesized strands can proceed in several ways. Direct detection can be done when the newly synthesized strands comprise detectable labels, either by incorporation into the primers or by incorporation of modified labelled nucleotides into the growing strand. Alternatively, as is more fully outlined below, indirect detection of unlabelled strands (which now serve as "targets" in the detection mode) can occur using a variety of sandwich assay configurations. As will be appreciated by those in the art, any of the newly synthesized strands can serve as the "target" for form an assay complex on a surface with a capture probe. In NASBA and TMA, it is preferable to utilize the newly formed RNA strands as the target, as this is where significant amplification occurs.

In this way, a number of secondary target molecules are made. As is more fully outlined below, these reactions (that is, the products of these reactions) can be detected in a number of ways.

Signal Amplification Techniques

In a preferred embodiment, the amplification technique is signal amplification. Signal amplification involves the use of limited number of target molecules as templates to either generate multiple signalling probes or allow the use of multiple signalling probes. Signal amplification strategies include LCR, CPT, Q-3R, invasive cleavage technology, and the use of amplification probes in sandwich assays.

Single Base Extension (SBE)

In a preferred embodiment, single base extension (SBE; sometimes referred to as "minisequencing") is used for amplification. It should also be noted that SBE finds use in genotyping, as is described below. Briefly, SBE is a technique that utilizes an extension primer that hybridizes to the target nucleic acid. A polymerase (generally a DNA polymerase) is used to extend the 3' end of the primer with a nucleotide analog labeled a detection label as described herein. Based on the fidelity of the enzyme, a nucleotide is only incorporated into the extension primer if it is complementary to the adjacent base in the target strand. Generally, the nucleotide is derivatized such that no further extensions can occur, so only a single nucleotide is added. However, for amplification reactions, this may not be necessary. Once the labeled nucleotide is added, detection of the label proceeds as outlined herein. See generally Sylvanen et al., Genomics 8:684-692 (1990); U.S. Pat. Nos. 5,846,710 and 5,888,819; Pastinen et al., Genomics Res. 7(6):606-614 (1997); all of which are expressly incorporated herein by reference.

The reaction is initiated by introducing the assay complex comprising the target sequence (i.e. the array) to a solution comprising a first nucleotide, frequently an nucleotide analog. By "nucleotide analog" in this context herein is meant a deoxynucleoside-triphosphate (also called deoxynucleotides or dNTPs, i.e. dATP, dTTP, dCTP and dGTP), that is further derivatized to be chain terminating. As will be appreciated by those in the art, any number of nucleotide analogs may be used, as long as a polymerase enzyme will still incorporate the nucleotide at the interrogation position. Preferred embodiments utilize dideoxy-triphosphate nucleotides (ddNTPs). Generally, a set of nucleotides comprising ddATP, ddCTP, ddGTP and ddTTP is used, at least one of which includes a label, and preferably all four. For amplification rather than genotyping reactions, the labels may all be the same; alternatively, different labels may be used.

In a preferred embodiment, the nucleotide analogs comprise a detectable label, which can be either a primary or secondary detectable label. Preferred primary labels are those outlined above. However, the enzymatic incorporation of nucleotides comprising fluorophores is poor under many conditions; accordingly, preferred embodiments utilize secondary detectable labels. In addition, as outlined below, the use of secondary labels may also facilitate the removal of unextended probes.

In addition to a first nucleotide, the solution also comprises an extension enzyme, generally a DNA polymerase. Suitable DNA polymerases include, but are not limited to, the Klenow fragment of DNA polymerase 1, SEQUENASE 1.0 and SEQUENASE 2.0 (U.S. Biochemical), T5 DNA polymerase and Phi29 DNA polymerase. If the NTP is complementary to the base of the detection position of the target sequence, which is adjacent to the extension primer, the extension enzyme will add it to the extension primer. Thus, the extension primer is modified, i.e. extended, to form a modified primer, sometimes referred to herein as a "newly synthesized strand".

A limitation of this method is that unless the target nucleic acid is in sufficient concentration, the amount of unextended primer in the reaction greatly exceeds the resultant extended-labeled primer. The excess of unextended primer competes with the detection of the labeled primer in the assays described herein. Accordingly, when SBE is used, preferred embodiments utilize methods for the removal of unextended primers as outlined herein.

One method to overcome this limitation is thermocycling minisequencing in which repeated cycles of annealing, primer extension, and heat denaturation using a thermocycler and thermo-stable polymerase allows the amplification of the extension probe which results in the accumulation of extended primers. For example, if the original unextended primer to target nucleic acid concentration is 100:1 and 100 thermocycles and extensions are performed, a majority of the primer will be extended.

As will be appreciated by those in the art, the configuration of the SBE system can take on several forms. As for the LCR reaction described below, the reaction may be done in solution, and then the newly synthesized strands, with the base-specific detectable labels, can be detected. For example, they can be directly hybridized to capture probes that are complementary to the extension primers, and the presence of the label is then detected.

Alternatively, the SBE reaction can occur on a surface. For example, a target nucleic acid may be captured using a first capture probe that hybridizes to a first target domain of the target, and the reaction can proceed at a second target domain. The extended labeled primers are then bound to a second capture probe and detected.

Thus, the SBE reaction requires, in no particular order, an extension primer, a polymerase and dNTPs, at least one of which is labeled.

Oligonucleotide Ligation Amplification (,OLA)

In a preferred embodiment, the signal amplification technique is OLA. OLA, which is referred to as the ligation chain reaction (LCR) when two-stranded substrates are used, involves the ligation of two smaller probes into a single long probe, using the target sequence as the template. In LCR, the ligated probe product becomes the predominant template as the reaction progresses. The method can be run in two different ways; in a first embodiment, only one strand of a target sequence is used as a template for ligation; alternatively, both strands may be used. See generally U.S. Pat. Nos. 5,185,243, 5,679,524 and 5,573,907; EP 0 320 308 B1; EP 0 336 731 B1;

EP 0 439 182 131; WO 90/01069; WO 89/12696; WO 97/31256; and WO 89/09835, and U.S. Ser. Nos. 60/078,102 and 60/073,011, all of which are incorporated by reference.

In a preferred embodiment, the single-stranded target sequence comprises a first target domain and a second target domain, which are adjacent and contiguous. A first OLA primer and a second OLA primer nucleic acids are added, that are substantially complementary to their respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two OLA primers are then covalently attached, for example using a ligase enzyme such as is known in the art, to form a modified primer. This forms a first hybridization complex comprising the ligated probe and the target sequence. This hybridization complex is then denatured (disassociated), and the process is repeated to generate a pool of ligated probes.

In a preferred embodiment, OLA is done for two strands of a double-stranded target sequence. The target sequence is denatured, and two sets of probes are added: one set as outlined above for one strand of the target, and a separate set (i.e. third and fourth primer probe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

As will be appreciated by those in the art, the ligation product can be detected in a variety of ways. In a preferred embodiment, the ligation reaction is run in solution. In this embodiment, only one of the primers carries a detectable label, e.g. the first ligation probe, and the capture probe on the bead is substantially complementary to the other probe, e.g. the second ligation probe. In this way, unextended labeled ligation primers will not interfere with the assay. That is, in a preferred embodiment, the ligation product is detected by solid-phase oligonucleotide probes. The solid-phase probes are preferably complementary to at least a portion of the ligation product. In a preferred embodiment, the solid-phase probe is complementary to the 5' detection oligonucleotide portion of the ligation product. This substantially reduces or eliminates false signal generated by the optically-labeled 3' primers. Preferably, detection is accomplished by removing the unligated 5' detection oligonucleotide from the reaction before application to a capture probe. In one embodiment, the unligated 5' detection oligonucleotides are removed by digesting 3 non-protected oligonucleotides with a 3' exonuclease, such as, exonuclease I. The ligation products are protected from exo I digestion by including, for example, 4-phosphorothioate residues at their 3' terminus, thereby, rendering them resistant to exonuclease digestion. The unligated detection oligonucleotides are not protected and are digested.

Alternatively, the target nucleic acid is immobilized on a solid-phase surface. The ligation assay is performed and unligated oligonucleotides are removed by washing under appropriate stringency to remove unligated oligonucleotides. The ligated oligonucleotides are eluted from the target nucleic acid using denaturing conditions, such as, 0.1 N NaOH, and detected as described herein.

Again, as outlined above, the detection of the LCR reaction can also occur directly, In the case where one or both of the primers comprises at least one detectable label, or indirectly, using sandwich assays, through the use of additional probes; that is, the ligated probes can serve as target sequences, and detection may utilize amplification probes, capture probes, capture extender probes, label probes, and label extender probes, etc.

Rolling-Circle Amplification (RCA)

In a preferred embodiment the signal amplification technique is RCA. Rolling-circle amplification is generally described in Baner et al. (1998) Nuc. Acids Res. 26:5073-5078; Barany, F. (1991) Proc. Na!!. Acad. Sc!. USA 88:189-193; and Lizardi et al. (1998) Nat. Genet. 19:225-232, all of which are incorporated by reference in their entirety.

In general, RCA may be described in two ways. First, as is outlined in more detail below, a single probe is hybridized with a target nucleic acid. Each terminus of the probe hybridizes adjacently on the target nucleic acid and the OLA assay as described above occurs. When ligated, the probe is circularized while hybridized to the target nucleic acid. Addition of a polymerase results in extension of the circular probe. However, since the probe has no terminus, the polymerase continues to extend the probe repeatedly. Thus results in amplification of the circular probe.

A second alternative approach involves OLA followed by RCA. In this embodiment, an immobilized primer is contacted with a target nucleic acid. Complementary sequences will hybridize with each other resulting in an immobilized duplex. A second primer is contacted with the target nucleic acid. The second primer hybridizes to the target nucleic acid adjacent to the first primer. An OLA assay is performed as described above. Ligation only occurs if the primer are complementary to the target nucleic acid. When a mismatch occurs, particularly at one of the nucleotides to be ligated, ligation will not occur. Following ligation of the oligonucleotides, the ligated, immobilized, oligonucleotide is then hybridized with an RCA probe. This is a circular probe that is designed to specifically hybridize with the ligated oligonucleotide and will only hybridize with an oligonucleotide that has undergone ligation. RCA is then performed as is outlined in more detail below.

Accordingly, in an preferred embodiment, a single oligonucleotide is used both for OLA and as the circular template for RCA (referred to herein as a "padlock probe" or a "RCA probe"). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent to the first domain. Hybridization of the oligonucleotide to the target nucleic acid results in the formation of a hybridization complex. Ligation of the "primers" (which are the discrete ends of a single oligonucleotide) results in the formation of a modified hybridization complex containing a circular probe i.e. an RCA template complex. That is, the oligonucleotide is circularized while still hybridized with the target nucleic acid. This serves as a circular template for RCA. Addition of a polymerase to the RCA template complex results in the formation of an amplified product nucleic acid. Following RCA, the amplified product nucleic acid is detected (FIG. 6). This can be accomplished in a variety of ways; for example, the polymerase may incorporate labelled nucleotides, or alternatively, a label probe is used that is substantially complementary to a portion of the RCA probe and comprises at least one label is used.

The polymerase can be any polymerase, but is preferably one lacking 3' exonuclease activity (3'exo'). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

In a preferred embodiment, the RCA probe contains an adapter sequence as outlined herein, with adapter capture probes on the array, for example on a microsphere when microsphere arrays are being used. Alternatively, unique portions of the RCA probes, for example all or part of the sequence corresponding to the target sequence, can be used to bind to a capture probe.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA, the product nucleic acid is contacted with the appropriate restriction endonuclease. This results in cleavage of the product nucleic acid into smaller fragments. The fragments are then hybridized with the capture probe that is immobilized resulting in a concentration of product fragments onto the microsphere. Again, as outlined herein, these fragments can be detected in one of two ways: either labelled nucleotides are incorporated during the replication step, or an additional label probe is added.

Thus, in a preferred embodiment, the padlock probe comprises a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

The padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

Thus, the padlock probe of the invention contains at each terminus, sequences corresponding to OLA primers. The intervening sequence of the padlock probe contain in no particular order, an adapter sequence and a restriction endonuclease site. In addition, the padlock probe contains a RCA priming site.

Thus, in a preferred embodiment the OLA/RCA is performed in solution followed by restriction endonuclease cleavage of the RCA product. The cleaved product is then applied to an array comprising beads, each bead comprising a probe complementary to the adapter sequence located in the padlock probe. The amplified adapter sequence correlates with a particular target nucleic acid. Thus the incorporation of an endonuclease site allows the generation of short, easily hybridizable sequences. Furthermore, the unique adapter sequence in each rolling circle padlock probe sequence allows diverse sets of nucleic acid sequences to be analyzed in parallel on an array, since each sequence is resolved on the basis of hybridization specificity.

In an alternative OLA/RCA method, one of the OLA primers is immobilized on the microsphere; the second primer is added in solution. Both primers hybridize with the target nucleic acid forming a hybridization complex as described above for the OLA assay.

As described herein, the microsphere is distributed on an array. In a preferred embodiment, a plurality of microspheres each with a unique OLA primer is distributed on the array.

Following the OLA assay, and either before, after or concurrently with distribution of the beads on the array, a segment of circular DNA is hybridized to the bead-based ligated oligonucleotide forming a modified hybridization complex. Addition of an appropriate polymerase (3'exo'), as is known in the art, and corresponding reaction buffer to the array leads to amplification of the circular DNA. Since there is no terminus to the circular DNA, the polymerase continues to travel around the circular template generating extension product until it detaches from the template. Thus, a polymerase with high processivity can create several hundred or thousand copies of the circular template with all the copies linked in one contiguous strand.

Again, these copies are subsequently detected by one of two methods; either hybridizing a labeled oligo complementary to the circular target or via the incorporation of labeled nucleotides in the amplification reaction. The label is detected using conventional label detection methods as described herein.

In one embodiment, when the circular DNA contains sequences complementary to the ligated oligonucleotide it is preferable to remove the target DNA prior to contacting the ligated oligonucleotide with the circular DNA (See FIG. 7). This is done by denaturing the double-stranded DNA by methods known in the art. In an alternative embodiment, the double stranded DNA is not denatured prior to contacting the circular DNA.

In an alternative embodiment, when the circular DNA contains sequences complementary to the target nucleic acid, it is preferable that the circular DNA is complementary at a site distinct from the site bound to the ligated oligonucleotide. In this embodiment it is preferred that the duplex between the ligated oligonucleotide and target nucleic acid is not denatured or disrupted prior to the addition of the circular DNA so that the target DNA remains immobilized to the bead.

Hybridization and washing conditions are well known in the art; various degrees of stringency can be used. In some embodiments it is not necessary to use stringent hybridization or washing conditions as only microspheres containing the ligated probes will effectively hybridize with the circular DNA; microspheres bound to DNA that did not undergo ligation (those without the appropriate target nucleic acid) will not hybridize as strongly with the circular DNA as those primers that were ligated. Thus, hybridization and/or washing conditions are used that discriminate between binding of the circular DNA to the ligated primer and the unligated primer.

Alternatively, when the circular probe is designed to hybridize to the target nucleic acid at a site distinct from the site bound to the ligated oligonucleotide, hybridization and washing conditions are used to remove or dissociate the target nucleic acid from unligated oligonucleotides while target nucleic acid hybridizing with the ligated oligonucleotides will remain bound to the beads. In this embodiment, the circular probe only hybridizes to the target nucleic acid when the target nucleic acid is hybridized with a ligated oligonucleotide that is immobilized on a bead.

As is well known in the art, an appropriate polymerase (3' exo) is added to the array. The polymerase extends the sequence of a single-stranded DNA using double-stranded DNA as a primer site. In one embodiment, the circular DNA that has hybridized with the appropriate OLA reaction product serves as the primer for the polymerase. In the presence of an appropriate reaction buffer as is known in the art, the polymerase will extend the sequence of the primer using the single-stranded circular DNA as a template. As there is no terminus of the circular DNA, the polymerase will continue to extend the sequence of the circular DNA. In an alternative embodiment, the RCA probe comprises a discrete primer site located within the circular probe. Hybridization of primer nucleic acids to this primer site forms the polymerase template allowing RCA to proceed.

In a preferred embodiment, the polymerase creates more than 100 copies of the circular DNA. In more preferred embodiments the polymerase creates more than 1000 copies of the circular DNA; while in a most preferred embodiment the polymerase creates more than 10,000 copies or more than 50,000 copies of the template.

The amplified circular DNA sequence is then detected by methods known in the art and as described herein. Detection is accomplished by hybridizing with a labeled probe. The probe is labeled directly or indirectly. Alternatively, labeled nucleotides are incorporated into the amplified circular DNA product. The nucleotides can be labeled directly, or indirectly as is further described herein.

The RCA as described herein finds use in allowing highly specific and highly sensitive detection of nucleic acid target sequences. In particular, the method finds use in improving the multiplexing ability of DNA arrays and eliminating costly sample or target preparation. As an example, a substantial savings in cost can be realized by directly analyzing genomic DNA on an array, rather than employing an intermediate PCR amplification step. The method finds use in examining genomic DNA and other samples including mRNA.

In addition the RCA finds use in allowing rolling circle amplification products to be easily detected by hybridization to probes in a solid-phase format (e.g. an array of beads). An additional advantage of the RCA is that it provides the capability of multiplex analysis so that large numbers of sequences can be analyzed in parallel. By combining the sensitivity of RCA and parallel detection on arrays, many sequences can be analyzed directly from genomic DNA.

Chemical Ligation Techniques

A variation of LCR utilizes a "chemical ligation" of sorts, as is generally outlined in U.S. Pat. Nos. 5,616,464 and 5,767,259, both of which are hereby expressly incorporated by reference in their entirety. In this embodiment, similar to enzymatic ligation, a pair of primers are utilized, wherein the first primer is substantially complementary to a first domain of the target and the second primer is substantially complementary to an adjacent second domain of the target (although, as for enzymatic ligation, if a "gap" exists, a polymerase and dNTPs may be added to "fill in" the gap). Each primer has a portion that acts as a "side chain" that does not bind the target sequence and acts as one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes.

At least one of the side chains of the primers comprises an activatable cross-linking agent, generally covalently attached to the side chain, that upon activation, results in a chemical cross-link or chemical ligation. The activatable group may comprise any moiety that will allow cross-linking of the side chains, and include groups activated chemically, photonically and thermally, with photoactivatable groups being preferred. In some embodiments a single activatable group on one of the side chains is enough to result in cross-linking via interaction to a functional group on the other side chain; in alternate embodiments, activatable groups are required on each side chain.

Once the hybridization complex is formed, and the cross-linking agent has been activated such that the primers have been covalently attached, the reaction is subjected to conditions to allow for the disassociation of the hybridization complex, thus freeing up the target to serve as a template for the next ligation or cross-linking. In this way, signal amplification occurs, and can be detected as outlined herein.

Invasive Cleavage Techniques

In a preferred embodiment, the signal amplification technique is invasive cleavage technology, which is described in a number of patents and patent applications, including U.S. Pat. Nos. 5,846,717; 5,614,402; 5,719,028; 5,541,311; and 5,843,669, all of which are hereby incorporated by reference in their entirety. Invasive cleavage technology is based on structure-specific nucleases that cleave nucleic acids in a site-specific manner. Two probes are used: an "invader" probe and a "signalling" probe, that adjacently hybridize to a target sequence with overlap. For mismatch discrimination, the invader technology relies on complementarity at the overlap position where cleavage occurs. The enzyme cleaves at the overlap, and releases the "tail" which may or may not be labeled. This can then be detected.

Generally, invasive cleavage technology may be described as follows. A target nucleic acid is recognized by two distinct probes. A first probe, generally referred to herein as an "invader" probe, is substantially complementary to a first portion of the target nucleic acid. A second probe, generally referred to herein as a "signal probe", is partially complementary to the target nucleic acid; the 3' end of the signal oligonucleotide is substantially complementary to the target sequence while the 5' end is non-complementary and preferably forms a single-stranded "tail" or "arm". The non-complementary end of the second probe preferably comprises a generic or "unique" sequence, frequently referred to herein as a "detection sequence", that is used to indicate the presence or absence of the target nucleic acid, as described below. The detection sequence of the second probe preferably comprises at least one detectable label, although as outlined herein, since this detection sequence can function as a target sequence for a capture probe, sandwich configurations utilizing label probes as described herein may also be done.

Hybridization of the first and second oligonucleotides near or adjacent to one another on the target nucleic acid forms a number of structures. In a preferred embodiment, a forked cleavage structure forms and is a substrate of a nuclease which cleaves the detection sequence from the signal oligonucleotide. The site of cleavage is controlled by the distance or overlap between the 3' end of the invader oligonucleotide and the downstream fork of the signal oligonucleotide. Therefore, neither oligonucleotide is subject to cleavage when misaligned or when unattached to target nucleic acid.

In a preferred embodiment, the nuclease that recognizes the forked cleavage structure and catalyzes release of the tail is thermostable, thereby, allowing thermal cycling of the cleavage reaction, if desired. Preferred nucleases derived from thermostable DNA polymerases that have been modified to have reduced synthetic activity which is an undesirable side-reaction during cleavage are disclosed in U.S. Pat. Nos. 5,719,028 and 5,843,669, hereby expressly by reference. The synthetic activity of the DNA polymerase is reduced to a level where it does not interfere with detection of the cleavage reaction and detection of the freed tail. Preferably the DNA polymerase has no detectable polymerase activity. Examples of nucleases are those derived from *Thermus aquaticus, Thermus flavus*, or *Thermus thermophilus*.

In another embodiment, thermostable structure-specific nucleases are Flap endonucleases (FENs) selected from FEN-1 or FEN-2 like (e.g. XPG and RAD2 nucleases) from Archaebacterial species, for example, FEN-1 from *Methanococcus jannaschif, Pyrococcus furiosis, Pyrococcus woesei*, and *Archaeoglobus fulgidus*. (U.S. Pat. No. 5,843,669 and Lyamichev et al. 1999. Nature Biotechnology 17:292-297; both of which are hereby expressly by reference).

In a preferred embodiment, the nuclease is AfuFEN1 or PfuFEN1 nuclease. To cleave a forked structure, these nucleases require at least one overlapping nucleotide between the signal and invasive probes to recognize and cleave the 5' end of the signal probe. To effect cleavage the 3'-terminal nucleotide of the invader oligonucleotide is not required to be complementary to the target nucleic acid. In contest, mismatch of the signal probe one base upstream of the cleavage site prevents creation of the overlap and cleavage. The specificity of the nuclease reaction allows single nucleotide polymorphism (SNP) detection from, for example, genomic DNA, as outlined below (Lyamichev et al.).

The invasive cleavage assay is preferably performed on an array format. In a preferred embodiment, the signal probe has a detectable label, attached 5' from the site of nuclease cleavage (e.g. within the detection sequence) and a capture tag, as described below (e.g. biotin or other hapten) 3' from the site of nuclease cleavage. After the assay is carried out, the 3' portion of the cleaved signal probe (e.g. the detection sequence) are extracted, for example, by binding to streptavidin beads or by crosslinking through the capture tag to produce aggregates or by antibody to an attached hapten. By "capture tag" herein is a meant one of a pair of binding partners as described above, such as antigen/antibody pairs, digoxygenenin, dinitrophenol, etc.

The cleaved 5' region, e.g. the detection sequence, of the signal probe, comprises a label and is detected and optionally quantitated. In one embodiment, the cleaved 5' region is hybridized to a probe on an array (capture probe) and optically detected. As described below, many signal probes can be analyzed in parallel by hybridization to their complementary probes in an array.

In a preferred embodiment, the invasive cleavage reaction is configured to utilize a fluorophore-quencher reaction. A signalling probe comprising both a fluorophore and a quencher is used, with the fluorophore and the quencher on opposite sides of the cleavage site. As will be appreciated by those in the art, these will be positioned closely together. Thus, in the absence of cleavage, very little signal is seen due to the quenching reaction. After cleavage, however, the distance between the two is large, and thus fluorescence can be detected. Upon assembly of an assay complex, comprising the target sequence, an invader probe, and a signalling probe, and the introduction of the cleavage enzyme, the cleavage of the complex results in the disassociation of the quencher from the complex, resulting in an increase in fluorescence.

In this embodiment, suitable fluorophore-quencher pairs are as known in the art. For example, suitable quencher molecules comprise Dabcyl.

As will be appreciated by those in the art, this system can be configured in a variety of conformations, as discussed in FIG. 4, In a preferred embodiment, to obtain higher specificity and reduce the detection of contaminating uncleaved signal probe or incorrectly cleaved product, an additional enzymatic recognition step is introduced in the array capture procedure. For example, the cleaved signal probe binds to a capture probe to produce a double-stranded nucleic acid in the array. In this embodiment, the 3' end of the cleaved signal probe is adjacent to the 5' end of one strand of the capture probe, thereby, forming a substrate for DNA ligase (Broude et al. 1991. PNAS 91: 3072-3076). Only correctly cleaved product is ligated to the capture probe. Other incorrectly hybridized and non-cleaved signal probes are removed, for example, by heat denaturation, high stringency washes, and other methods that disrupt base pairing.

Cycling Probe Techniques (CPT)

In a preferred embodiment, the signal amplification technique is CPT. CPT technology is described in a number of patents and patent applications, including U.S. Pat. Nos. 5,011,769, 5,403,711, 5,660,988, and 4,876,187, and PCT published applications WO 95/05480, WO 95/1416, and WO 95/00667, and U.S. Ser. No. 09/014,304, all of which are expressly incorporated by reference in their entirety.

Generally, CPT may be described as follows. A CPT primer (also sometimes referred to herein as a "scissile primer"), comprises two probe sequences separated by a scissile linkage. The CPT primer is substantially complementary to the target sequence and thus will hybridize to it to form a hybridization complex. The scissile linkage is cleaved, without cleaving the target sequence, resulting in the two probe sequences being separated. The two probe sequences can thus be more easily disassociated from the target, and the reaction can be repeated any number of times. The cleaved primer is then detected as outlined herein.

By "scissile linkage" herein is meant a linkage within the scissile probe that can be cleaved when the probe is part of a hybridization complex, that is, when a double-stranded complex is formed. It is important that the scissile linkage cleave only the scissile probe and not the sequence to which it is hybridized (i.e. either the target sequence or a probe sequence), such that the target sequence may be reused in the reaction for amplification of the signal. As used herein, the scissile linkage, is any connecting chemical structure which joins two probe sequences and which is capable of being selectively cleaved without cleavage of either the probe sequences or the sequence to which the scissile probe is hybridized. The scissile linkage may be a single bond, or a multiple unit sequence. As will be appreciated by those in the art, a number of possible scissile linkages may be used.

In a preferred embodiment, the scissile linkage comprises RNA. This system, previously described in as outlined above, is based on the fact that certain double-stranded nucleases, particularly ribonucleases, will nick or excise RNA nucleosides from a RNA:DNA hybridization complex. Of particular use in this embodiment is RNAseH, Exo III, and reverse transcriptase.

In one embodiment, the entire scissile probe is made of RNA, the nicking is facilitated especially when carried out with a double-stranded ribonuclease, such as RNAseH or Exo III. RNA probes made entirely of RNA sequences are particularly useful because first, they can be more easily produced enzymatically, and second, they have more cleavage sites which are accessible to nicking or cleaving by a nicking agent, such as the ribonucleases. Thus, scissile probes made entirely of RNA do not rely on a scissile linkage since the scissile linkage is inherent in the probe.

In a preferred embodiment, when the scissile linkage is a nucleic acid such as RNA, the methods of the invention may be used to detect mismatches, as is generally described in U.S. Pat. No. 5,660,988, and WO 95/14106, hereby expressly incorporated by reference. These mismatch detection methods are based on the fact that RNAseH may not bind to and/or cleave an RNA:DNA duplex if there are mismatches present in the sequence. Thus, in the $NA_1$-R-$NA_2$ embodiments, $NA_1$ and $NA_2$ are non-RNA nucleic acids, preferably DNA. Preferably, the mismatch is within the RNA:DNA duplex, but in some embodiments the mismatch is present in an adjacent sequence very close to the desired sequence, close enough to affect the RNAseH (generally within one or two bases). Thus, in this embodiment, the nucleic acid scissile linkage is designed such that the sequence of the scissile linkage reflects the particular sequence to be detected, i.e. the area of the putative mismatch.

In some embodiments of mismatch detection, the rate of generation of the released fragments is such that the methods provide, essentially, a yes/no result, whereby the detection of virtually any released fragment indicates the presence of the desired target sequence. Typically, however, when there is only a minimal mismatch (for example, a 1-, 2- or 3-base mismatch, or a 3-base deletion), there is some generation of cleaved sequences even though the target sequence is not present. Thus, the rate of generation of cleaved fragments, and/or the final amount of cleaved fragments, is quantified to indicate the presence or absence of the target. In addition, the use of secondary and tertiary scissile probes may be particularly useful in this embodiment, as this can amplify the differences between a perfect match and a mismatch. These methods may be particularly useful in the determination of homozygotic or heterozygotic states of a patient.

In this embodiment, it is an important feature of the scissile linkage that its length is determined by the suspected difference between the target and the probe. In particular, this means that the scissile linkage must be of sufficient length to encompass the suspected difference, yet short enough so that the scissile linkage cannot inappropriately "specifically hybridize" to the selected nucleic acid molecule when the suspected difference is present; such inappropriate hybridization would permit excision and thus cleavage of scissile linkages even though the selected nucleic acid molecule was not fully complementary to the nucleic acid probe. Thus in a preferred embodiment, the scissile linkage is between 3 to 5 nucleotides in length, such that a suspected nucleotide difference from 1 nucleotide to 3 nucleotides is encompassed by the scissile linkage, and 0, 1 or 2 nucleotides are on either side of the difference.

Thus, when the scissile linkage is nucleic acid, preferred embodiments utilize from 1 to about 100 nucleotides, with from about 2 to about 20 being preferred and from about 5 to about 10 being particularly preferred.

CPT may be done enzymatically or chemically. That is, in addition to RNAseH, there are several other cleaving agents which may be useful in cleaving RNA (or other nucleic acid) scissile bonds. For example, several chemical nucleases have been reported; see for example Sigman et al., Annu. Rev. Biochem. 1990, 59, 207-236; Sigman et al., Chem. Rev. 1993, 93, 2295-2316; Bashkin et al., J. Org. Chem. 1990, 55, 5125-5132; and Sigman et al., Nucleic Acids and Molecular Biology, vol. 3, F. Eckstein and D. M. J. Lilley (Eds), Springer-Verlag, Heidelberg 1989, pp. 13-27; all of which are hereby expressly incorporated by reference.

Specific RNA hydrolysis is also an active area; see for example Chin, Acc. Chem. Res. 1991, 24, 145-152; Breslow et al., Tetrahedron, 1991, 47, 2365-2376; Anslyn et al., Angew. Chem. Int. Ed. Engl., 1997, 36, 432-450; and references therein, all of which are expressly incorporated by reference. Reactive phosphate centers are also of interest in developing scissile linkages, see Hendry et al., Prog. Inorg. Chem.: Bioinorganic Chem. 1990, 31, 201-258 also expressly incorporated by reference.

Current approaches to site-directed RNA hydrolysis include the conjugation of a reactive moiety capable of cleaving phosphodiester bonds to a recognition element capable of sequence-specifically hybridizing to RNA. In most cases, a metal complex is covalently attached to a DNA strand which forms a stable heteroduplex. Upon hybridization, a Lewis acid is placed in close proximity to the RNA backbone to effect hydrolysis; see Magda et al., J. Am. Chem. Soc. 1994, 116, 7439; Hall et al., Chem. Biology 1994, 1, 185-190; Bashkin et al., J. Am. Chem. Soc. 1994, 116, 5981-5982; Hall et al., Nucleic Acids Res. 1996, 24, 3522; Magda et al., J. Am. Chem. Soc. 1997, 119, 2293; and Magda et al., J. Am. Chem. Soc. 1997, 119, 6947, all of which are expressly incorporated by reference.

In a similar fashion, DNA-polyamine conjugates have been demonstrated to induce site-directed RNA strand scission; see for example, Yoshinari et al., J. Am. Chem. Soc. 1991, 113, 5899-5901; Endo et al., J. Org. Chem. 1997, 62, 846; and Barbier et al., J. Am. Chem. Soc. 1992, 114, 3511-3515, all of which are expressly incorporated by reference.

In a preferred embodiment, the scissile linkage is not necessarily RNA. For example, chemical cleavage moieties may be used to cleave basic sites in nucleic acids; see Belmont, et al., New J. Chem. 1997, 21, 47-54; and references therein, all of which are expressly incorporated herein by reference. Similarly, photocleavable moieties, for example, using transition metals, may be used; see Moucheron, et al., Inorg. Chem. 1997, 36, 584-592, hereby expressly by reference.

Other approaches rely on chemical moieties or enzymes; see for example Keck et al., Biochemistry 1995, 34, 12029-12037; Kirk et al., Chem. Commun. 1998, in press; cleavage of G-U basepairs by metal complexes; see Biochemistry, 1992, 31, 5423-5429; diamine complexes for cleavage of RNA; Komiyama, et al., J. Org. Chem. 1997, 62, 2155-2160; and Chow et al., Chem. Rev. 1997, 97, 1489-1513, and references therein, all of which are expressly incorporated herein by reference.

The first step of the CPT method requires hybridizing a primary scissile primer (also called a primary scissile probe) to the target. This is preferably done at a temperature that allows both the binding of the longer primary probe and disassociation of the shorter cleaved portions of the primary probe, as will be appreciated by those in the art. As outlined herein, this may be done in solution, or either the target or one or more of the scissile probes may be attached to a solid support. For example, it is possible to utilize "anchor probes" on a solid support which are substantially complementary to a portion of the target sequence, preferably a sequence that is not the same sequence to which a scissile probe will bind.

Similarly, as outlined herein, a preferred embodiment has one or more of the scissile probes attached to a solid support such as a bead. In this embodiment, the soluble target diffuses to allow the formation of the hybridization complex between the soluble target sequence and the support-bound scissile probe. In this embodiment, it may be desirable to include additional scissile linkages in the scissile probes to allow the release of two or more probe sequences, such that more than one probe sequence per scissile probe may be detected, as is outlined below, in the interests of maximizing the signal.

In this embodiment (and in other techniques herein), preferred methods utilize cutting or shearing techniques to cut the nucleic acid sample containing the target sequence into a size that will allow sufficient diffusion of the target sequence to the surface of a bead. This may be accomplished by shearing the nucleic acid through mechanical forces (e.g. sonication) or by cleaving the nucleic acid using restriction endonucleases. Alternatively, a fragment containing the target may be generated using polymerase, primers and the sample as a template, as in polymerase chain reaction (PCR). In addition, amplification of the target using PCR or LCR or related methods may also be done; this may be particularly useful when the target sequence is present in the sample at extremely low copy numbers. Similarly, numerous techniques are known in the art to increase the rate of mixing and hybridization including agitation, heating, techniques that increase the overall concentration such as precipitation, drying, dialysis, centrifugation, electrophoresis, magnetic bead concentration, etc.

In general, the scissile probes are introduced in a molar excess to their targets (including both the target sequence or other scissile probes, for example when secondary or tertiary scissile probes are used), with ratios of scissile probe:target of at least about 100:1 being preferred, at least about 1000:1 being particularly preferred, and at least about 10,000:1 being especially preferred. In some embodiments the excess of probe:target will be much greater. In addition, ratios such as these may be used for all the amplification techniques outlined herein.

Once the hybridization complex between the primary scissile probe and the target has been formed, the complex is subjected to cleavage conditions. As will be appreciated, this depends on the composition of the scissile probe; if it is RNA, RNAseH is introduced. It should be noted that under certain circumstances, such as is generally outlined in WO 95/00666 and WO 95/00667, hereby incorporated by reference, the use of a double-stranded binding agent such as RNAseH may allow the reaction to proceed even at temperatures above the Tm of the primary probe:target hybridization complex. Accordingly, the addition of scissile probe to the target can be done either first, and then the cleavage agent or cleavage conditions introduced, or the probes may be added in the presence of the cleavage agent or conditions.

The cleavage conditions result in the separation of the two (or more) probe sequences of the primary scissile probe. As a result, the shorter probe sequences will no longer remain hybridized to the target sequence, and thus the hybridization complex will disassociate, leaving the target sequence intact.

The optimal temperature for carrying out the CPT reactions is generally from about 5° C. to about 25° C. below the melting temperatures of the probe:target hybridization complex. This provides for a rapid rate of hybridization and high degree of specificity for the target sequence. The Tm of any particular hybridization complex depends on salt concentration, G-C content, and length of the complex, as is known in the art and described herein.

During the reaction, as for the other amplification techniques herein, it may be necessary to suppress cleavage of the probe, as well as the target sequence, by nonspecific nucleases. Such nucleases are generally removed from the sample during the isolation of the DNA by heating or extraction procedures. A number of inhibitors of single-stranded nucleases such as vanadate, inhibitors it-ACE and RNAsin, a placental protein, do not affect the activity of RNAseH. This may not be necessary depending on the purity of the RNAseH and/or the target sample.

These steps are repeated by allowing the reaction to proceed for a period of time. The reaction is usually carried out for about 15 minutes to about 1 hour. Generally, each molecule of the target sequence will turnover between 100 and 1000 times in this period, depending on the length and sequence of the probe, the specific reaction conditions, and the cleavage method. For example, for each copy of the target sequence present in the test sample 100 to 1000 molecules will be cleaved by RNAseH. Higher levels of amplification can be obtained by allowing the reaction to proceed longer, or using secondary, tertiary, or quaternary probes, as is outlined herein.

Upon completion of the reaction, generally determined by time or amount of cleavage, the uncleaved scissile probes must be removed or neutralized prior to detection, such that the uncleaved probe does not bind to a, detection probe, causing false positive signals. This may be done in a variety of ways, as is generally described below.

In a preferred embodiment, the separation is facilitated by the use of beads containing the primary probe. Thus, when the scissile probes are attached to beads, removal of the beads by filtration, centrifugation, the application of a magnetic field, electrostatic interactions for charged beads, adhesion, etc., results in the removal of the uncleaved probes.

In a preferred embodiment, the separation is based on strong acid precipitation. This is useful to separate long (generally greater than 50 nucleotides) from smaller fragments (generally about 10 nucleotides). The introduction of a strong acid such as trichloroacetic acid into the solution causes the longer probe to precipitate, while the smaller cleaved fragments remain in solution. The solution can be centrifuged or filtered to remove the precipitate, and the cleaved probe sequences can be quantitated.

In a preferred embodiment, the scissile probe contains both a detectable label and an affinity binding ligand or moiety, such that an affinity support is used to carry out. the separation. In this embodiment, it is important that the detectable label used for detection is not on the same probe sequence that contains the affinity moiety, such that removal of the uncleaved probe, and the cleaved probe containing the affinity moiety, does not remove all the detectable labels. Alternatively, the scissile probe may contain a capture tag; the binding partner of the capture tag is attached to a solid support such as glass beads, latex beads, dextrans, etc. and used to pull out the uncleaved probes, as is known in the art. The cleaved probe sequences, which do not contain the capture tag, remain in solution and then can be detected as outlined below.

In a preferred embodiment, similar to the above embodiment, a separation sequence of nucleic acid is included in the scissile probe, which is not cleaved during the reaction. A nucleic acid complementary to the separation sequence is attached to a solid support such as a bead and serves as a catcher sequence. Preferably, the separation sequence is added to the scissile probes, and is not recognized by the target sequence, such that a generalized catcher sequence may be utilized in a variety of assays.

After removal of the uncleaved probe, as required, detection proceeds via the addition of the cleaved probe sequences to the array compositions, as outlined below. In general, the cleaved probe is bound to a capture probe, either directly or indirectly, and the label is detected. In a preferred embodiment, no higher order probes are used, and detection is based on the probe sequence(s) of the primary primer. In a preferred embodiment, at least one, and preferably more, secondary probes (also referred to herein as secondary primers) are used; the secondary probes hybridize to the domains of the cleavage probes; etc.

Thus, CPT requires, again in no particular order, a first CPT primer comprising a first probe sequence, a scissile linkage and a second probe sequence; and a cleavage agent.

In this manner, CPT results in the generation of a large amount of cleaved primers, which then can be detected as outlined below.

Sandwich Assay Techniques

In a preferred embodiment, the signal amplification technique is a "sandwich" assay, as is generally described in U.S. Ser. No. 60/073,011 and in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. Although sandwich assays do not result in the alteration of primers, sandwich assays can be considered signal amplification techniques since multiple signals (i.e. label probes) are bound to a single target, resulting in the amplification of the signal. Sandwich assays may be used when the target sequence does not contain a label; or when adapters are used, as outlined below.

As discussed herein, it should be noted that the sandwich assays can be used for the detection of primary target sequences (e.g. from a patient sample), or as a method to detect the product of an amplification reaction as outlined above; thus for example, any of the newly synthesized strands outlined above, for example using PCR, LCR, NASBA, SDA, etc., may be used as the "target sequence" in a sandwich assay.

As will be appreciated by those in the art, the systems of the invention may take on a large number of different configurations. In general, there are three types of systems that can be used: (1) "non-sandwich" systems (also referred to herein as "direct" detection) in which the target sequence itself is labeled with detectable labels (again, either because the primers comprise labels or due to the incorporation of labels into the newly synthesized strand); (2) systems in which label probes directly bind to the target sequences; and (3) systems in which label probes are indirectly bound to the target sequences, for example through the use of amplifier probes.

The anchoring of the target sequence to the bead is done through the use of capture probes and optionally either capture extender probes (sometimes referred to as "adapter sequences" herein). When only capture probes are utilized, it is necessary to have unique capture probes for each target sequence; that is, the surface must be customized to contain unique capture probes; e.g. each bead comprises a different capture probe. Alternatively, capture extender probes may be used, that allow a "universal" surface, i.e. a surface containing a single type of capture probe that can be used to detect any target sequence. "Capture extender" probes have a first portion that will hybridize to all or part of the capture probe, and a second portion that will hybridize to a first portion of the target sequence. This then allows the generation of customized soluble probes, which as will be appreciated by those in the art is generally simpler and less costly. As shown herein, two capture extender probes may be used. This has generally been done to stabilize assay complexes for example when the target sequence is large, or when large amplifier probes (particularly branched or dendrimer amplifier probes) are used.

Detection of the amplification reactions of the invention, including the direct detection of amplification products and indirect detection utilizing label probes (i.e. sandwich assays), is preferably done by detecting assay complexes comprising detectable labels, which can be attached to the assay complex in a variety of ways, as is more fully described below.

Once the target sequence has preferably been anchored to the array, an amplifier probe is hybridized to the target sequence, either directly, or through the use of one or more label extender probes, which serves to allow "generic" amplifier probes to be made. As for all the steps outlined herein, this may be done simultaneously with capturing, or sequentially. Preferably, the amplifier probe contains a multiplicity of amplification sequences, although in some embodiments, as described below, the amplifier probe may contain only a single amplification sequence, or at least two amplification sequences. The amplifier probe may take on a number of different forms; either a branched conformation, a dendrimer conformation, or a linear "string" of amplification sequences. Label probes comprising detectable labels (preferably but not required to be fluorophores) then hybridize to the amplification sequences (or in some cases the label probes hybridize directly to the target sequence), and the labels detected, as is more fully outlined below.

Accordingly, the present invention provides compositions comprising an amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single-stranded nucleic acid amplification sequence, with a multiplicity of amplification sequences being preferred.

Amplifier probes comprise a first probe sequence that is used, either directly or indirectly, to hybridize to the target sequence. That is, the amplifier probe itself may have a first probe sequence that is substantially complementary to the target sequence, or it has a first probe sequence that is substantially complementary to a portion of an additional probe, in this case called a label extender probe, that has a first portion that is substantially complementary to the target sequence. In a preferred embodiment, the first probe sequence of the amplifier probe is substantially complementary to the target sequence.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

In a preferred embodiment, the amplifier probe does not hybridize to the sample target sequence directly, but instead hybridizes to a first portion of a label extender probe. This is particularly useful to allow the use of "generic" amplifier probes, that is, amplifier probes that can be used with a variety of different targets. This may be desirable since several of the amplifier probes require special synthesis techniques. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'-3' orientation of the target or probe sequences. For example, assuming a 5'-3' orientation of the complementary target sequence, the first portion may be located either 5' to the second portion, or 3' to the second portion. For convenience herein, the order of probe sequences are generally shown from left to right.

In a preferred embodiment, more than one label extender probe-amplifier probe pair may be used, that is, n is more than 1. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce non-specific binding, as is generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below. Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to which at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end either directly or with short intervening sequences to form a polymer. As with the other amplifier configurations, there may be additional sequences or moieties between the amplification sequences. In one embodiment, the linear amplifier probe has a single amplification sequence.

In addition, the amplifier probe may be totally linear, totally branched, totally dendrimeric, or any combination thereof.

The amplification sequences of the amplifier probe are used, either directly, or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

In addition, the compositions of the invention may include "preamplifier" molecules, which serves a bridging moiety between the label extender molecules and the amplifier probes. In this way, more amplifier and thus more labels are ultimately bound to the detection probes. Preamplifier molecules may be either linear or branched, and typically contain in the range of about 30-3000 nucleotides.

Thus, label probes are either substantially complementary to an amplification sequence or to a portion of the target sequence.

Detection of the amplification reactions of the invention, including the direct detection of amplification products and indirect detection utilizing label probes (i.e. sandwich assays), is done by detecting assay complexes comprising labels as is outlined herein.

In addition to amplification techniques, the present invention also provides a variety of genotyping reactions that can be similarly detected and/or quantified.

Genotyping

In this embodiment, the invention provides compositions and methods for the detection (and optionally quantification) of differences or variations of sequences (e.g. SNPs) using bead arrays for detection of the differences. That is, the bead array serves as a platform on which a variety of techniques may be used to elucidate the nucleotide at the position of interest ("the detection position"). In general, the methods described herein relate to the detection of nucleotide substitutions, although as will be appreciated by those in the art, deletions, insertions, inversions, etc. may also be detected.

These techniques fall into five general categories: (1) techniques that rely on traditional hybridization methods that utilize the variation of stringency conditions (temperature, buffer conditions, etc.) to distinguish nucleotides at the detection position; (2) extension techniques that add a base ("the base") to basepair with the nucleotide at the detection position; (3) ligation techniques, that rely on the specificity of ligase enzymes (or, in some cases, on the specificity of chemical techniques), such that ligation reactions occur preferentially if perfect complementarity exists at the detection position; (4) cleavage techniques, that also rely on enzymatic or chemical specificity such that cleavage occurs preferentially if perfect complementarity exists; and (5) techniques that combine these methods.

As outlined herein, in this embodiment the target sequence comprises a position for which sequence information is desired, generally referred to herein as the "detection position" or "detection locus". In a preferred embodiment, the detection position is a single nucleotide, although in some embodiments, it may comprise a plurality of nucleotides, either contiguous with each other or separated by one or more nucleotides. By "plurality" as used herein is meant at least two. As used herein, the base which basepairs with a detection position base in a hybrid is termed a "readout position" or an "interrogation position".

In some embodiments, as is outlined herein, the target sequence may not be the sample target sequence but instead is a product of a reaction herein, sometimes referred to herein as a "secondary" or "derivative" target sequence. Thus, for example, in SBE, the extended primer may serve as the target sequence; similarly, in invasive cleavage variations, the cleaved detection sequence may serve as the target sequence.

As above, if required, the target sequence is prepared using known techniques. Once prepared, the target sequence can be used in a variety of reactions for a variety of reasons. For example, in a preferred embodiment, genotyping reactions are done. Similarly, these reactions can also be used to detect the presence or absence of a target sequence. In addition, in any reaction, quantitation of the amount of a target sequence may be done. While the discussion below focuses on genotyping reactions, the discussion applies equally to detecting the presence of target sequences and/or their quantification.

Furthermore, as outlined below for each reaction, each of these techniques may be used in a solution based assay, wherein the reaction is done in solution and a reaction product is bound to the array for subsequent detection, or in solid phase assays, where the reaction occurs on the surface and is detected.

These reactions are generally classified into 5 basic categories, as outlined below.

Simple Hybridization Genotyping in a preferred embodiment, straight hybridization methods are used to elucidate the identity of the base at the detection position. Generally speaking, these techniques break down into two basic types of reactions: those that rely on competitive hybridization techniques, and those that discriminate using stringency parameters and combinations thereof.

Competitive Hybridization

In a preferred embodiment, the use of competitive hybridization probes is done to elucidate either the identity of the nucleotide(s) at the detection position or the presence of a mismatch. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

It should be noted in this context that "mismatch" is a relative term and meant to indicate a difference in the identity of a base at a particular position, termed the "detection position" herein, between two sequences. In general, sequences that differ from wild type sequences are referred to as mismatches. However, particularly in the case of SNPs, what constitutes "wild type" may be difficult to determine as multiple alleles can be relatively frequently observed in the population, and thus "mismatch" in this context requires the artificial adoption of one sequence as a standard. Thus, for the purposes of this invention, sequences are referred to herein as "match" and "mismatch". Thus, the present invention may be used to detect substitutions, insertions or deletions as compared to a wild-type sequence.

In a preferred embodiment, a plurality of probes (sometimes referred to herein as "readout probes") are used to identify the base at the detection position. In this embodiment, each different readout probe comprises a different detection label (which, as outlined below, can be either a primary label or a secondary label) and a different base at the position that will hybridize to the detection position of the target sequence (herein referred to as the readout position) such that differential hybridization will occur. That is, all other parameters being equal, a perfectly complementary readout probe (a "match probe") will in general be more stable and have a slower off rate than a probe comprising a mismatch (a "mismatch probe") at any particular temperature. Accordingly, by using different readout probes, each with a different base at the readout position and each with a different label, the identification of the base at the detection position is elucidated.

Accordingly, a detectable label is incorporated into the readout probe. In a preferred embodiment, a set of readout probes are used, each comprising a different base at the readout position. In some embodiments, each readout probe comprises a different label, that is distinguishable from the others.

For example, a first label may be used for probes comprising adenosine at the readout position, a second label may be used for probes comprising guanine at the readout position, etc. In a preferred embodiment, the length and sequence of each readout probe is identical except for the readout position, although this need not be true in all embodiments.

The number of readout probes used will vary depending on the end use of the assay. For example, many SNPs are biallelic, and thus two readout probes, each comprising an interrogation base that will basepair with one of the detection position bases. For sequencing, for example, for the discovery of SNPs, a set of four readout probes are used, although SNPs may also be discovered with fewer readout parameters.

As will be appreciated by those in the art and additionally outlined below, this system can take on a number of different configurations, including a solution phase assay and a solid phase assay.

Solution Phase Assay

A solution phase assay that is followed by attaching the target sequence to an array is depicted in FIG. 8D. In FIG. 8D, a reaction with two different readout probes is shown. After the competitive hybridization has occurred, the target sequence is added to the array, which may take on several configurations, outlined below.

Solid Phase Assay

In a preferred embodiment, the competition reaction is done on the array. This system may take on several configurations.

In a preferred embodiment, a sandwich assay of sorts is used. In this embodiment, the bead comprises a capture probe that will hybridize to a first target domain of a target sequence, and the readout probe will hybridize to a second target domain, as is generally depicted in FIG. 8A. In this embodiment, the first target domain may be either unique to the target, or may be an exogeneous adapter sequence added to the target sequence as outlined below, for example through the use of PCR reactions. Similarly, a sandwich assay that utilizes a capture extender probe, as described below, to attach the target sequence to the array is depicted in FIG. 8C.

Alternatively, the capture probe itself can be the readout probe as is shown in Figure BB; that is, a plurality of microspheres are used, each comprising a capture probe that has a different base at the readout position. In general, the target sequence then hybridizes preferentially to the capture probe most closely matched. In this embodiment, either the target sequence itself is labeled (for example, it may be the product of an amplification reaction) or a label probe may bind to the target sequence at a domain remote from the detection position. In this embodiment, since it is the location on the array that serves to identify the base at the detection position, different labels are not required.

In a further embodiment, the target sequence itself is attached to the array, as generally depicted for bead arrays in FIG. 8E and described below.

Stringency Variation

In a preferred embodiment, sensitivity to variations in stringency parameters are used to determine either the identity of the nucleotide(s) at the detection position or the presence of a mismatch. As a preliminary matter, the use of different stringency conditions such as variations in temperature and buffer composition to determine the presence or absence of mismatches in double stranded hybrids comprising a single stranded target sequence and a probe is well known.

With particular regard to temperature, as is known in the art, differences in the number of hydrogen bonds as a function of basepairing between perfect matches and mismatches can be exploited as a result of their different Tms (the temperature at which 50% of the hybrid is denatured). Accordingly, a hybrid comprising perfect complementarity will melt at a higher temperature than one comprising at least one mismatch, all other parameters being equal. (It should be noted that for the purposes of the discussion herein, all other parameters (i.e. length of the hybrid, nature of the backbone (i.e. naturally occurring or nucleic acid analog), the assay solution composition and the composition of the bases, including G-C content are kept constant). However, as will be appreciated by those in the art, these factors may be varied as well, and then taken into account.)

In general, as outlined herein, high stringency conditions are those that result in perfect matches remaining in hybridization complexes, while imperfect matches melt off. Similarly, low stringency conditions are those that allow the formation of hybridization complexes with both perfect and imperfect matches. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

As will be appreciated by those in the art, mismatch detection using temperature may proceed in a variety of ways, and is similar to the use of readout probes as outlined above. Again, as outlined above, a plurality of readout probes may be used in a sandwich format; in this embodiment, all the probes may bind at permissive, low temperatures (temperatures below the Tm of the mismatch); however, repeating the assay at a higher temperature (above the Tm of the mismatch) only the perfectly matched probe may bind. Thus, this system may be run with readout probes with different detectable labels, as outlined above. Alternatively, a single probe may be used to query whether a particular base is present.

Alternatively, as described above, the capture probe may serve as the readout probe; in this embodiment, a single label may be used on the target; at temperatures above the Tm of the mismatch, only signals from perfect matches will be seen, as the mismatch target will melt off.

Similarly, variations in buffer composition may be used to elucidate the presence or absence of a mismatch at the detection position. Suitable conditions include, but are not limited to, formamide concentration. Thus, for example, "low" or "permissive" stringency conditions include formamide concentrations of 0 to 10%, while "high" or "stringent" conditions utilize formamide concentrations of $\geq 40\%$. Low stringency conditions include NaCl concentrations of $\leq 1$ M, and high stringency conditions include concentrations of $\leq 0.3$ M. Furthermore, low stringency conditions include $MgCl_2$ concentrations of $\geq 10$ mM, moderate stringency as 1-10 mM, and high stringency conditions include concentrations of $\leq 1$ mM.

In this embodiment, as for temperature, a plurality of readout probes may be used, with different bases in the readout position (and optionally different labels). Running the assays under the permissive conditions and repeating under stringent conditions will allow the elucidation of the base at the detection position.

In one embodiment, the probes used as readout probes are "Molecular Beacon" probes as are generally described in Whitcombe et al., Nature Biotechnology 17:804 (1999), hereby incorporated by reference. As is known in the art, Molecular Beacon probes form "hairpin" type structures, with a fluorescent label on one end and a quencher on the other. In the absence of the target sequence, the ends of the hairpin hybridize, causing quenching of the label. In the presence of a target sequence, the hairpin structure is lost in favor of target sequence binding, resulting in a loss of quenching and thus an increase in signal.

In one embodiment, the Molecular Beacon probes can be the capture probes as outlined herein for readout probes. For example, different beads comprising labeled Molecular Beacon probes (and different bases at the readout position) are made optionally they comprise different labels. Alternatively, since Molecular Beacon probes can have spectrally resolvable signals, all four probes (if a set of four different bases with is used) differently labelled are attached to a single bead.

Extension Genotyping

In this embodiment, any number of techniques are used to add a nucleotide to the readout position of a probe hybridized to the target sequence adjacent to the detection position. By relying on enzymatic specificity, preferentially a perfectly complementary base is added. All of these methods rely on the enzymatic incorporation of nucleotides at the detection position. This may be done using chain terminating dNTPs, such that only a single base is incorporated (e.g. single base extension methods), or under conditions that only a single type of nucleotide is added followed by identification of the added nucleotide (extension and pyrosequencing techniques).

Single Base Extension

In a preferred embodiment, single base extension (SBE; sometimes referred to as "minisequencing") is used to determine the identity of the base at the detection position. SBE is as described above, and utilizes an extension primer that hybridizes to the target nucleic acid immediately adjacent to the detection position. A polymerase (generally a DNA polymerase) is used to extend the 3' end of the primer with a nucleotide analog labeled a detection label as described herein. Based on the fidelity of the enzyme, a nucleotide is only incorporated into the readout position of the growing nucleic acid strand if it is perfectly complementary to the base in the target strand at the detection position. The nucleotide may be derivatized such that no further extensions can occur, so only a single nucleotide is added. Once the labeled nucleotide is added, detection of the label proceeds as outlined herein.

The reaction is initiated by introducing the assay complex comprising the target sequence (i.e. the array) to a solution comprising a first nucleotide. In general, the nucleotides comprise a detectable label, which may be either a primary or a secondary label. In addition, the nucleotides may be nucleotide analogs, depending on the configuration of the system. For example, if the dNTPs are added in sequential reactions, such that only a single type of dNTP can be added, the nucleotides need not be chain terminating. In addition, in this embodiment, the dNTPs may all comprise the same type of label.

Alternatively, if the reaction comprises more than one dNTP, the dNTPs should be chain terminating, that is, they have a blocking or protecting group at the 3' position such that no further dNTPs may be added by the enzyme. As will be appreciated by those in the art, any number of nucleotide analogs may be used, as long as a polymerase enzyme will still incorporate the nucleotide at the readout position. Preferred embodiments utilize dideoxy-triphosphate nucleotides (ddNTPs) and halogenated dNTPs. Generally, a set of nucleotides comprising ddATP, ddCTP, ddGTP and ddTTP is used, each with a different detectable label, although as outlined herein, this may not be required. Alternative preferred embodiments use acyclo nucleotides (NEN). These chain terminating nucleotide analogs are particularly good substrates for Deep vent (exo') and thermosequenase.

In addition, as will be appreciated by those in the art, the single base extension reactions of the present invention allow the precise incorporation of modified bases into a growing nucleic acid strand. Thus, any number of modified nucleotides may be incorporated for any number of reasons, including probing structure-function relationships (e.g. DNA:DNA or DNA:protein interactions), cleaving the nucleic acid, crosslinking the nucleic acid, incorporate mismatches, etc.

As will be appreciated by those in the art, the configuration of the genotyping SBE system can take on several forms.

Solution Phase Assay

As for the OLA reaction described below, the reaction may be done in solution, and then the newly synthesized strands, with the base-specific detectable labels, can be detected. For example, they can be directly hybridized to capture probes that are complementary to the extension primers, and the presence of the label is then detected. This is schematically depicted in FIG. 9C. As will be appreciated by those in the art, a preferred embodiment utilizes four different detectable labels, i.e. one for each base, such that upon hybridization to the capture probe on the array, the identification of the base can be done isothermally. Thus, FIG. 9C depicts the readout position 35 as not necessarily hybridizing to the capture probe.

In a preferred embodiment, adapter sequences can be used in a solution format. In this embodiment, a single label can be used with a set of four separate primer extension reactions. In this embodiment, the extension reaction is done in solution; each reaction comprises a different dNTP with the label or labeled ddNTP when chain termination is desired. For each locus genotyped, a set of four different extension primers are used, each with a portion that will hybridize to the target sequence, a different readout base and each with a different adapter sequence of 15-40 bases, as is more fully outlined below. After the primer extension reaction is complete, the four separate reactions are pooled and hybridized to an array comprising complementary probes to the adapter sequences. A genotype is derived by comparing the probe intensities of the four different hybridized adapter sequences corresponding to a give locus.

In addition, since unextended primers do not comprise labels, the unextended primers need not be removed. However, they may be, if desired, as outlined below; for example, if a large excess of primers are used, there may not be sufficient signal from the extended primers competing for binding to the surface.

Alternatively, one of skill in the art could use a single label and temperature to determine the identity of the base; that is, the readout position of the extension primer hybridizes to a position on the capture probe. However, since the three mismatches will have lower Tms than the perfect match, the use of temperature could elucidate the identity of the detection position base.

Solid Phase Assay

Alternatively, the reaction may be done on a surface by capturing the target sequence and then running the SBE reaction, in a sandwich type format schematically depicted in FIG. 9A. In this embodiment, the capture probe hybridizes to a first domain of the target sequence (which can be endogeneous or an exogenous adapter sequence added during an amplification reaction), and the extension primer hybridizes to a second target domain immediately adjacent to the detection position. The addition of the enzyme and the required NTPs results in the addition of the interrogation base. In this embodiment, each NTP must have a unique label. Alternatively, each NTP reaction may be done sequentially on a different array. As is known by one of skill in the art, ddNTP and dNTP are the preferred substrates when DNA polymerase is the added enzyme; NTP is the preferred substrate when RNA polymerase is the added enzyme.

Furthermore, as is more fully outlined below and depicted in FIG. 9D, capture extender probes can be used to attach the target sequence to the bead. In this embodiment, the hybridization complex comprises the capture probe, the target sequence and the adapter sequence.

Similarly, the capture probe itself can be used as the extension probe, with its terminus being directly adjacent to the detection position. This is schematically depicted in FIG. 9B. Upon the addition of the target sequence and the SBE reagents, the modified primer is formed comprising a detectable label, and then detected. Again, as for the solution based reaction, each NTP must have a unique label, the reactions must proceed sequentially, or different arrays must be used. Again, as is known by one of skill in the art, ddNTP and dNTP are the preferred substrates when DNA polymerase is the added enzyme; NTP is the preferred substrate when RNA polymerase is the added enzyme.

In addition, as outlined herein, the target sequence may be directly attached to the array; the extension primer hybridizes to it and the reaction proceeds.

Figure 9F:
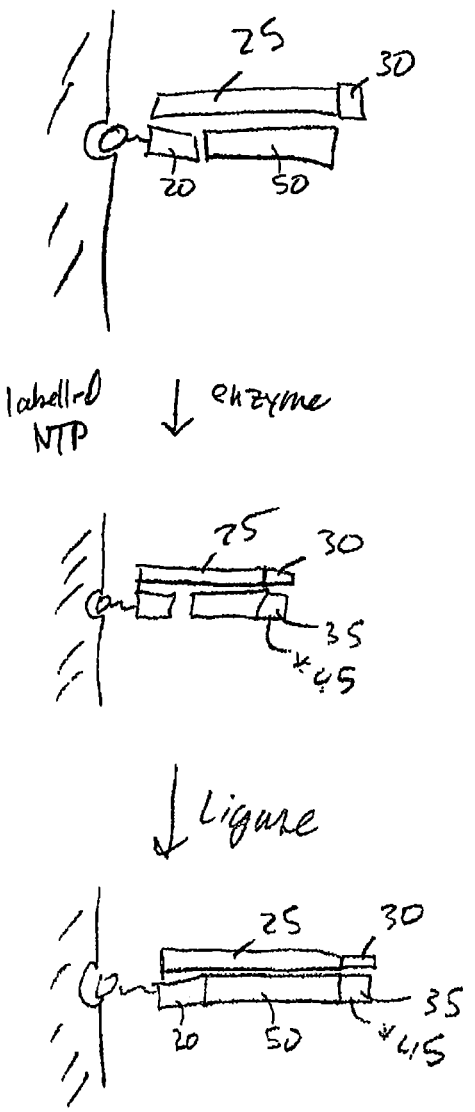

Variations on this are shown in FIGS. 9E and 9F, where the capture probe and the extension probe adjacently hybridize to the target sequence. Either before or after extension of the extension probe, a ligation step may be used to attach the capture and extension probes together for stability. These are further described below as combination assays.

Figure 9G:
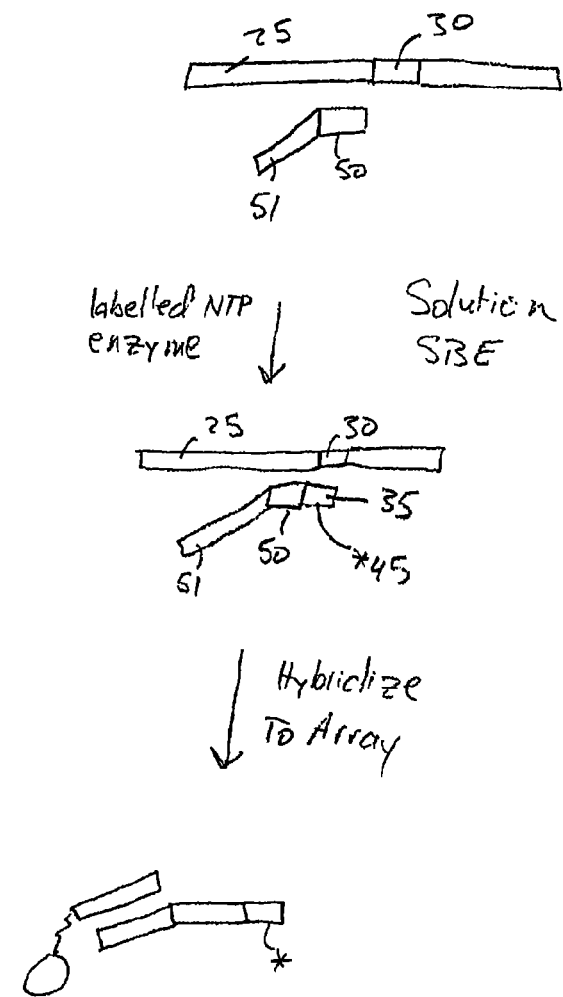

In addition, FIG. 9G depicts the SBE solution reaction followed by hybridization of the product of the reaction to the bead array to capture an adapter sequence.

As will be appreciated by those in the art, the determination of the base at the detection position can proceed in several ways. In a preferred embodiment, the reaction is run with all four nucleotides (assuming all four nucleotides are required), each with a different label, as is generally outlined herein. Alternatively, a single label is used, by using four reactions: this may be done either by using a single substrate and sequential reactions, or by using four arrays. For example, dATP can be added to the assay complex, and the generation of a signal evaluated; the dATP can be removed and dTTP added, etc. Alternatively, four arrays can be used; the first is reacted with dATP, the second with dTTP, etc., and the presence or absence of a signal evaluated. Alternatively, the reaction includes chain terminating nucleotides such as ddNTPs or acyclo-NTPS.

Alternatively, ratiometric analysis can be done; for example, two labels, "A" and "B", on two substrates (e.g. two arrays) can be done. In this embodiment, two sets of primer extension reactions are performed, each on two arrays, with each reaction containing a complete set of four chain terminating NTPs. The first reaction contains two "A" labeled nucleotides and two "B" labeled nucleotides (for example, A and C may be "A" labeled, and G and T may be "B" labeled). The second reaction also contains the two labels, but switched; for example, A and G are "A" labeled and T and C are "B" labeled. This reaction composition allows a biallelic marker to be ratiometrically scored; that is, the intensity of the two labels in two different "color" channels on a single substrate is compared, using data from a set of two hybridized arrays. For instance, if the marker is A/G, then the first reaction on the first array is used to calculate a ratiometric genotyping score; if the marker is A/C, then the second reaction on the second array is used for the calculation; if the marker is GIT, then the second array is used, etc. This concept can be applied to all possible biallelic marker combinations. "Scoring" a genotype using a single fiber ratiometric score allows a much more robust genotyping than scoring a genotype using a comparison of absolute or normalized intensities between two different arrays.

Removal of Unextended Primers

In a preferred embodiment, for both SBE as well as a number of other reactions outlined herein, it is desirable to remove the unextended or unreacted primers from the assay mixture, and particularly from the array, as unextended primers will compete with the extended (labeled) primers in binding to capture probes, thereby diminishing the signal. The concentration of the unextended primers relative to the extended primer may be relatively high, since a large excess of primer is usually required to generate efficient primer annealing. Accordingly, a number of different techniques may be used to facilitate the removal of unextended primers. As outlined above, these generally include methods based on removal of unreacted primers by binding to a solid support, protecting the reacted primers and degrading the unextended ones, and separating the unreacted and reacted primers.

Protection and Degradation

In this embodiment, the ddTNPs or dNTPs that are added during the reaction confer protection from degradation (whether chemical or enzymatic). Thus, after the assay, the degradation components are added, and unreacted primers are degraded, leaving only the reacted primers. Labeled protecting groups are particularly preferred; for example, 3'-substituted-2'-dNTPs can contain anthranylic derivatives that are fluorescent (with alkali or enzymatic treatment for removal of the protecting group).

In a preferred embodiment, the secondary label is a nuclease inhibitor, such as thiol NTPs. In this embodiment, the chain-terminating NTPs are chosen to render extended primers resistant to nucleases, such as 3'-exonucleases. Addition of an exonuclease will digest the non-extended primers leaving only the extended primers to bind to the capture probes on the array. This may also be done with OLA, wherein the ligated probe will be protected but the unprotected ligation probe will be digested.

In this embodiment, suitable 3'-exonucieases include, but are not limited to, exo I, exo III, exo VII, and 3'-5' exophosphodiesterases.

Alternatively, an 3' exonuclease may be added to a mixture of 3' labeled biotin/streptavidin; only the unreacted oligonucleotides will be degraded. Following exonuclease treatment, the exonuclease and the streptavidin can be degraded using a protease such as proteinase K. The surviving nucleic acids (i.e. those that were biotinylated) are then hybridized to the array.

Separation Systems

The use of secondary label systems (and even some primary label systems) can be used to separate unreacted and reacted probes; for example, the addition of streptavidin to a nucleic acid greatly increases its size, as well as changes its physical properties, to allow more efficient separation techniques. For example, the mixtures can be size fractionated by exclusion chromatography, affinity chromatography, filtration or differential precipitation.

Non-terminated Extension

In a preferred embodiment, methods of adding a single base are used that do not rely on chain termination. That is, similar to SBE, enzymatic reactions that utilize dNTPs and polymerases can be used; however, rather than use chain terminating dNTPs, regular dNTPs are used. This method relies on a time-resolved basis of detection; only one type of base is added during the reaction. Thus, for example, four different reactions each containing one of the dNTPs can be done; this is generally accomplished by using four different substrates, although as will be appreciated by those in the art, not all four reactions need occur to identify the nucleotide at a detection position. In this embodiment, the signals from single additions can be compared to those from multiple additions; that is, the addition of a single ATP can be distinguished on the basis of signal intensity from the addition of two or three ATPs. These reactions are accomplished as outlined above for SBE, using extension primers and polymerases; again, one label or four different labels can be used, although as outlined herein, the different NTPs must be added sequentially.

A preferred method of extension in this embodiment is pyrosequencing.

PyroSequencing

Pyrosequencing is an extension and sequencing method that can be used to add one or more nucleotides to the detection position(s); it is very similar to SBE except that chain terminating NTPs need not be used (although they may be). Pyrosequencing relies on the detection of a reaction product, PPi, produced during the addition of an NTP to a growing oligonucleotide chain, rather than on a label attached to the nucleotide. One molecule of PPi is produced per dNTP added to the extension primer. That is, by running sequential reactions with each of the nucleotides, and monitoring the reaction products, the identity of the added base is determined.

The release of pyrophosphate (PPi) during the DNA polymerase reaction can be quantitatively measured by many different methods and a number of enzymatic methods have been described; see Reeves et al., Anal. Biochem. 28:282 (1969); Guillory et al., Anal. Biochem. 39:170 (1971); Johnson et al., Anal. Biochem. 15:273 (1968); Cook et al., Anal. Biochem. 91:557 (1978); Drake et al., Anal. Biochem. 94:117 (1979); WO93/23564; WO 98128440; WO98/13523; Nyren et al., Anal. Biochem. 151:504 (1985); all of which are incorporated by reference. The latter method allows continuous monitoring of PPi and has been termed ELIDA (Enzymatic Luminometric Inorganic Pyrophosphate Detection Assay). A preferred embodiment utilizes any method which can result in the generation of an optical signal, with preferred embodiments utilizing the generation of a chemiluminescent or fluorescent signal.

A preferred method monitors the creation of PPi by the conversion of PPi to ATP by the enzyme sulfurylase, and the subsequent production of visible light by firefly luciferase (see Ronaghi et al., Science 281:363 (1998), incorporated by reference). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase, luciferase, and optionally a nucleotide-degrading enzyme such as apyrase. A dNTP is only incorporated into the growing DNA strand if it is complementary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

Accordingly, a preferred embodiment of the methods of the invention is as follows. A substrate comprising microspheres containing the target sequences and extension primers, forming hybridization complexes, is dipped or contacted with a reaction volume (chamber or well) comprising a single type of dNTP, an extension enzyme, and the reagents and enzymes necessary to detect PPi. If the dNTP is complementary to the base of the target portion of the target sequence adjacent to the extension primer, the dNTP is added, releasing PPi and generating detectable light, which is detected as generally described in U.S. Ser. Nos. 09/151,877 and 09/189,543, and PCT US98/09163, all of which are hereby incorporated by reference. If the dNTP is not complementary, no detectable signal results. The substrate is then contacted with a second reaction volume (chamber) comprising a different dNTP and the additional components of the assay. This process is repeated if the identity of a base at a second detection position is desirable.

In a preferred embodiment, washing steps, i.e. the use of washing chambers, may be done in between the dNTP reaction chambers, as required. These washing chambers may optionally comprise a nucleotide-degrading enzyme, to remove any unreacted dNTP and decreasing the background signal, as is described in WO 98/28440, incorporated herein by reference.

As will be appreciated by those in the art, the system can be configured in a variety of ways, including both a linear progression or a circular one; for example, four arrays may be used that each can dip into one of four reaction chambers arrayed in a circular pattern. Each cycle of sequencing and reading is followed by a 90 degree rotation, so that each substrate then dips into the next reaction well.

In a preferred embodiment, one or more internal control sequences are used. That is, at least one microsphere in the array comprises a known sequence that can be used to verify that the reactions are proceeding correctly. In a preferred embodiment, at least four control sequences are used, each of which has a different nucleotide at each position: the first control sequence will have an adenosine at position 1, the second will have a cytosine, the third a guanosine, and the fourth a thymidine, thus ensuring that at least one control sequence is "lighting up" at each step to serve as an internal control.

As for simple extension and SBE, the pyrosequencing systems may be configured in a variety of ways; for example, the target sequence may be attached to the bead in a variety of ways, including direct attachment of the target sequence; the use of a capture probe with a separate extension probe; the use of a capture extender probe, a capture probe and a separate extension probe; the use of adapter sequences in the target sequence with capture and extension probes; and the use of a capture probe that also serves as the extension probe.

One additional benefit of pyrosequencing for genotyping purposes is that since the reaction does not rely on the incorporation of labels into a growing chain, the unreacted extension primers need not be removed.

Allelic PCR

In a preferred embodiment, the method used to detect the base at the detection position is allelic PCR, referred to herein as "aPCR". As described in Newton et al., Nucl. Acid Res. 17:2503 (1989), hereby expressly incorporated by reference, allelic PCR allows single base discrimination based on the fact that the PCR reaction does not proceed well if the terminal 3'-nucieotide is mismatched, assuming the DNA polymerase being used lacks a 3'-exonuciease proofreading activity. Accordingly, the identification of the base proceeds by using allelic PCR primers (sometimes referred to herein as aPCR primers) that have readout positions at their 3' ends. Thus the target sequence comprises a first domain comprising at its 5' end a detection position.

In general, aPCR may be briefly described as follows. A double stranded target nucleic acid is denatured, generally by raising the temperature, and then cooled in the presence of an excess of a aPCR primer, which then hybridizes to the first target strand. If the readout position of the aPCR primer basepairs correctly with the detection position of the target sequence, a DNA polymerase (again, that lacks 3'-exonuciease activity) then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus aPCR steps are denaturation, annealing and extension. The particulars of aPCR are well known, and include the use of a thermostable polymerase such as Taq I polymerase and thermal cycling.

Accordingly, the aPCR reaction requires at least one aPCR primer, a polymerase, and a set of dNTPs. As outlined herein, the primers may comprise the label, or one or more of the dNTPs may comprise a label.

Furthermore, the aPCR reaction may be run as a competition assay of sorts. For example, for biallelic SNPs, a first aPCR primer comprising a first base at the readout position and a first label, and a second aPCR primer comprising a different base at the readout position and a second label, may be used. The PCR primer for the other strand is the same. The examination of the ratio of the two colors can serve to identify the base at the detection position.

In general, as is more fully outlined below, the capture probes on the beads of the array are designed to be substantially complementary to the extended part of the primer; that is, unextended primers will not bind to the capture probes.

Ligation Techniques for Genotyping

In this embodiment, the readout of the base at the detection position proceeds using a ligase. In this embodiment, it is the specificity of the ligase which is the basis of the genotyping; that is, ligases generally require that the 5' and 3' ends of the ligation probes have perfect complementarity to the target for ligation to occur. Thus, in a preferred embodiment, the identity of the base at the detection position proceeds utilizing OLA as described above, as is generally depicted in FIG. 10. The method can be run at least two different ways; in a first embodiment, only one strand of a target sequence is used as a template for ligation; alternatively, both strands may be used; the latter is generally referred to as Ligation Chain Reaction or LCR.

This method is based on the fact that two probes can be preferentially ligated together, if they are hybridized to a target strand and if perfect complementarity exists at the two bases being ligated together. Thus, in this embodiment, the target sequence comprises a contiguous first target domain comprising the detection position and a second target domain adjacent to the detection position. That is, the detection position is "between" the rest of the first target domain and the second target domain. A first ligation probe is hybridized to the first target domain and a second ligation probe is hybridized to the second target domain. If the first ligation probe has a base perfectly complementary to the detection position base, and the adjacent base on the second probe has perfect complementarity to its position, a ligation structure is formed such that the two probes can be ligated together to form a ligated probe. If this complementarity does not exist, no ligation structure is formed and the probes are not ligated together to an appreciable degree. This may be done using heat cycling, to allow the ligated probe to be denatured off the target sequence such that it may serve as a template for further reactions. In addition, as is more fully outlined below, this method may also be done using ligation probes that are separated by one or more nucleotides, if dNTPs and a polymerase are added (this is sometimes referred to as "Genetic Bit" analysis).

In a preferred embodiment, LCR is done for two strands of a double-stranded target sequence. The target sequence is denatured, and two sets of probes are added: one set as outlined above for one strand of the target, and a separate set (i.e. third and fourth primer probe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

As will be appreciated by those in the art, the ligation product can be detected in a variety of ways. Preferably, detection is accomplished by removing the unligated labeled probe from the reaction before application to a capture probe. In one embodiment, the unligated probes are removed by digesting 3' non-protected oligonucleotides with a 3' exonuclease, such as, exonuclease I. The ligation products are protected from exo I digestion by including, for example, the use of a number of sequential phosphorothioate residues at their 3' terminus (for example at least four), thereby, rendering them resistant to exonuclease digestion. The unligated detection oligonucleotides are not protected and are digested.

As for most or all of the methods described herein, the assay can take on a solution-based form or a solid-phase form.

Solution Based OLA

In a preferred embodiment, as shown in FIG. 10A, the ligation reaction is run in solution. In this embodiment, only one of the primers carries a detectable label, e.g. the first ligation probe, and the capture probe on the bead is substantially complementary to the other probe, e.g. the second ligation probe. In this way, unextended labeled ligation primers will not interfere with the assay. This substantially reduces or eliminates false signal generated by the optically-labeled 3' primers.

In addition, a solution-based OLA assay that utilizes adapter sequences may be done. In this embodiment, rather than have the target sequence comprise the adapter sequences, one of the ligation probes comprises the adapter sequence. This facilitates the creation of "universal arrays". For example, as depicted in FIG. 10E, the first ligation probe has an adapter sequence that is used to attach the ligated probe to the array.

Again, as outlined above for SBE, unreacted ligation primers, may be removed from the mixture as needed. For example, the first ligation probe may comprise the label (either a primary or secondary label) and the second may be blocked at its 3' end with an exonuclease blocking moiety; after ligation and the introduction of the nuclease, the labeled ligation probe will be digested, leaving the ligation product and the second probe; however, since the second probe is unlabeled, it is effectively silent in the assay. Similarly, the second probe may comprise a binding partner used to pull out the ligated probes, leaving unligated labeled ligation probes behind. The binding pair is then disassociated and added to the array.

Solid Phase Based OLA

Alternatively, the target nucleic acid is immobilized on a solid-phase surface. The OLA assay is performed and unligated oligonucleotides are removed by washing under appropriate stringency to remove unligated oligonucleotides and thus the label. For example, as depicted in FIG. 10B, the capture probe can comprise one of the ligation probes. Similarly, FIGS. 10C and 10D depict alternative attachments.

Again, as outlined above, the detection of the OLA reaction can also occur directly, in the case where one or both of the primers comprises at least one detectable label, or indirectly, using sandwich assays, through the use of additional probes; that is, the ligated probes can serve as target sequences, and detection may utilize amplification probes, capture probes, capture extender probes, label probes, and label extender probes, etc.

Solid Phase Oligonucleotide Ligation Assay (SPOLA)

In a preferred embodiment, a novel method of OLA is used, termed herein "solid phase oligonucleotide assay", or "SPOLA". In this embodiment, the ligation probes are both attached to the same site on the surface of the array (e.g. when microsphere arrays are used, to the same bead), one at its 5' end (the "upstream probe") and one at its 3' end (the "downstream probe"), as is generally depicted in FIG. 11. This may be done as is will be appreciated by those in the art. At least one of the probes is attached via a cleavable linker, that upon cleavage, forms a reactive or detectable (fluorophore) moiety. If ligation occurs, the reactive moiety remains associated with the surface; but if no ligation occurs, due to a mismatch, the reactive moiety is free in solution to diffuse away from the surface of the array. The reactive moiety is then used to add a detectable label.

Generally, as will be appreciated by those in the art, cleavage of the cleavable linker should result in asymmetrical products; i.e. one of the "ends" should be reactive, and the other should not, with the configuration of the system such that the reactive moiety remains associated with the surface if ligation occurred. Thus, for example, amino acids or succinate esters can be cleaved either enzymatically (via peptidases (aminopeptidase and carboxypeptidase) or proteases) or chemically (acid/base hydrolysis) to produce an amine and a carboxyl group. One of these groups can then be used to add a detectable label, as will be appreciated by those in the art and discussed herein.

Padlock Probe Ligation

In a preferred embodiment, the ligation probes are specialized probes called "padlock probes". Nilsson et al, 1994, Science 265:2085, hereby incorporated by reference. These probes have a first ligation domain that is identical to a first ligation probe, in that it hybridizes to a first target sequence domain, and a second ligation domain, identical to the second ligation probe, that hybridizes to an adjacent target sequence domain. Again, as for OLA, the detection position can be either at the 3' end of the first ligation domain or at the 5' end of the second ligation domain. However, the two ligation domains are connected by a linker, frequently nucleic acid. The configuration of the system is such that upon ligation of the first and second ligation domains of the padlock probe, the probe forms a circular probe, and forms a complex with the target sequence wherein the target sequence is "inserted" into the loop of the circle.

In this embodiment, the unligated probes may be removed through degradation (for example, through a nuclease), as there are no "free ends" in the ligated probe, Cleavage Techniques for Genotyping In a preferred embodiment, the specificity for genotyping is provided by a cleavage enzyme. There are a variety of enzymes known to cleave at specific sites, either based on sequence specificity, such as restriction endonucleases, or using structural specificity, such as is done through the use of invasive cleavage technology.

Endonuclease Techniques

In a preferred embodiment, enzymes that rely on sequence specificity are used. In general, these systems rely on the cleavage of double stranded sequence containing a specific sequence recognized by a nuclease, preferably an endonuclease including resolvases.

These systems may work in a variety of ways, as is generally depicted in FIG. 12. In one embodiment (FIG. 12A), a labeled readout probe (generally attached to a bead of the array) is used; the binding of the target sequence forms a double stranded sequence that a restriction endonuclease can then recognize and cleave, if the correct sequence is present. An enzyme resulting in "sticky ends" is shown in FIG. 12A. The cleavage results in the loss of the label, and thus a loss of signal.

Alternatively, as will be appreciated by those in the art, a labelled target sequence may be used as well; for example, a labelled primer may be used in the PCR amplification of the target, such that the label is incorporated in such a manner as to be cleaved off by the enzyme.

Alternatively, the readout probe (or, again, the target sequence) may comprise both a fluorescent label and a quencher, as is known in the art and depicted in FIG. 12B. In this embodiment, the label and the quencher are attached to different nucleosides, yet are close enough that the quencher molecule results in little or no signal being present. Upon the introduction of the enzyme, the quencher is cleaved off, leaving the label, and allowing signalling by the label.

In addition, as will be appreciated by those in the art, these systems can be both solution-based assays or solid-phase assays, as outlined herein.

Furthermore, there are some systems that do not require cleavage for detection; for example, some nucleic acid binding proteins will bind to specific sequences and can thus serve as a secondary label. For example, some transcription factors will bind in a highly sequence dependent manner, and can distinguish between two SNPs. Having bound to the hybridization complex, a detectable binding partner can be added for detection. In addition, mismatch binding proteins based on mutated transcription factors can be used.

In addition, as will be appreciated by those in the art, this type of approach works with other cleavage methods as well, for example the use of invasive cleavage methods, as outlined below.

Invasive Cleavage

In a preferred embodiment, the determination of the identity of the base at the detection position of the target sequence proceeds using invasive cleavage technology. As outlined above for amplification, invasive cleavage techniques rely on the use of structure-specific nucleases, where the structure can be formed as a result of the presence or absence of a mismatch. Generally, invasive cleavage technology may be described as follows. A target nucleic acid is recognized by two distinct probes. A first probe, generally referred to herein as an "invader" probe, is substantially complementary to a first portion of the target nucleic acid. A second probe, generally referred to herein as a "signal probe", is partially complementary to the target nucleic acid: the 3' end of the signal oligonucleotide is substantially complementary to the target sequence while the 5' end is non-complementary and preferably forms a single-stranded "tail" or "arm". The non-complementary end of the second probe preferably comprises a "generic" or "unique" sequence, frequently referred to herein as a "detection sequence", that is used to indicate the presence or absence of the target nucleic acid, as described below. The detection sequence of the second probe preferably comprises at least one detectable label. Alternative methods have the detection sequence functioning as a target sequence for a capture probe, and thus rely on sandwich configurations using label probes.

Hybridization of the first and second oligonucleotides near or adjacent to one another on the target nucleic acid forms a number of structures. In a preferred embodiment, a forked cleavage structure, as shown in FIG. 13, forms and is a substrate of a nuclease which cleaves the detection sequence from the signal oligonucleotide. The site of cleavage is controlled by the distance or overlap between the 3' end of the invader oligonucleotide and the downstream fork of the signal oligonucleotide. Therefore, neither oligonucleotide is subject to cleavage when misaligned or when unattached to target nucleic acid.

As above, the invasive cleavage assay is preferably performed on an array format. In a preferred embodiment, the signal probe has a detectable label, attached 5' from the site of nuclease cleavage (e.g. within the detection sequence) and a capture tag, as described herein for removal of the unreacted products (e.g. biotin or other hapten) 3' from the site of nuclease cleavage. After the assay is carried out, the uncleaved probe and the 3' portion of the cleaved signal probe (e.g. the detection sequence) may be extracted, for example, by binding to streptavidin beads or by crosslinking through the capture tag to produce aggregates or by antibody to an attached hapten. By "capture tag" herein is a meant one of a pair of binding partners as described above, such as antigen/antibody pairs, digoxygenenin, dinitrophenol, etc.

The cleaved 5' region, e.g. the detection sequence, of the signal probe, comprises a label and is detected and optionally quantitated. In one embodiment, the cleaved 5' region is hybridized to a probe on an array (capture probe) and optically detected (FIG. 13). As described below, many different signal probes can be analyzed in parallel by hybridization to their complementary probes in an array. In a preferred embodiment as depicted in FIG. 13, combination techniques are used to obtain higher specificity and reduce the detection of contaminating uncleaved signal probe or incorrectly cleaved product, an enzymatic recognition step is introduced in the array capture procedure. For example, as more fully outlined below, the cleaved signal probe binds to a capture probe to produce a double-stranded nucleic acid in the array. In this embodiment, the 3' end of the cleaved signal probe is adjacent to the 5' end of one strand of the capture probe, thereby, forming a substrate for DNA ligase (Broude et al. 1991. PNAS 91: 3072-3076). Only correctly cleaved product is ligated to the capture probe. Other incorrectly hybridized and non-cleaved signal probes are removed, for example, by heat denaturation, high stringency washes, and other methods that disrupt base pairing.

Accordingly, the present invention provides methods of determining the identity of a base at the detection position of a target sequence. In this embodiment, the target sequence comprises, 5' to 3', a first target domain comprising an overlap domain comprising at least a nucleotide in the detection position, and a second target domain contiguous with the detection position. A first probe (the "invader probe") is hybridized to the first target domain of the target sequence. A second probe (the "signal probe"), comprising a first portion that hybridizes to the second target domain of the target sequence and a second portion that does not hybridize to the target sequence, is hybridized to the second target domain. If the second probe comprises a base that is perfectly complementary to the detection position a cleavage structure is formed. The addition of a cleavage enzyme, such as is described in U.S. Pat. Nos. 5,846,717; 5,614,402; 5,719,029; 5,541,311 and 5,843,669, all of which are expressly incorporated by reference, results in the cleavage of the detection sequence from the signalling probe. This then can be used as a target sequence in an assay complex.

In addition, as for a variety of the techniques outlined herein, unreacted probes (i.e. signalling probes, in the case of invasive cleavage), may be removed using any number of techniques. For example, the use of a binding partner (70 in FIG. 13C) coupled to a solid support comprising the other member of the binding pair can be done. Similarly, after cleavage of the primary signal probe, the newly created cleavage products can be selectively labeled at the 3' or 5' ends using enzymatic or chemical methods.

Again, as outlined above, the detection of the invasive cleavage reaction can occur directly, in the case where the detection sequence comprises at least one label, or indirectly, using sandwich assays, through the use of additional probes; that is, the detection sequences can serve as target sequences, and detection may utilize amplification probes, capture probes, capture extender probes, label probes, and label extender probes, etc.

In addition, as for most of the techniques outlined herein, these techniques may be done for the two strands of a double-stranded target sequence. The target sequence is denatured, and two sets of probes are added: one set as outlined above for one strand of the target, and a separate set for the other strand of the target.

Thus, the invasive cleavage reaction requires, in no particular order, an invader probe, a signalling probe, and a cleavage enzyme.

As for other methods outlined herein, the invasive cleavage reaction may be done as a solution based assay or a solid phase assay.

Solution-based Invasive Cleavage

The invasive cleavage reaction may be done in solution, followed by addition of one of the components to an array, with optional (but preferable) removal of unreacted probes. For example, as depicted in FIG. 13C, the reaction is carried out in solution, using a capture tag (i.e. a member of a binding partner pair) that is separated from the label on the detection sequence with the cleavage site. After cleavage (dependent on the base at the detection position), the signalling probe is cleaved. The capture tag is used to remove the uncleaved probes (for example, using magnetic particles comprising the other member of the binding pair), and the remaining solution is added to the array. FIG. 13C depicts the direct attachment of the detection sequence to the capture probe. In this embodiment, the detection sequence can effectively act as an adapter sequence. In alternate embodiments, as depicted in FIG. 13D, the detection sequence is unlabelled and an additional label probe is used; as outlined below, this can be ligated to the hybridization complex.

Solid-phase Based Assays

The invasive cleavage reaction can also be done as a solid-phase assay. As depicted in FIG. 13A, the target sequence can be attached to the array using a capture probe (in addition, although not shown, the target sequence may be directly attached to the array). In a preferred embodiment, the signalling probe comprises both a fluorophore label (attached to the portion of the signalling probe that hybridizes to the target) and a quencher (generally on the detection sequence), with a cleavage site in between. Thus, in the absence of cleavage, very little signal is seen due to the quenching reaction. After cleavage, however, the detection sequence is removed, along with the quencher, leaving the unquenched fluorophore. Similarly, the invasive probe may be attached to the array, as depicted in FIG. 13B.

In a preferred embodiment, the invasive cleavage reaction is configured to utilize a fluorophore-quencher reaction. A signalling probe comprising both a fluorophore and a quencher is attached to the bead. The fluorophore is contained on the portion of the signalling probe that hybridizes to the target sequence, and the quencher is contained on a portion of the signalling probe that is on the other side of the cleavage site (termed the "detection sequence" herein). In a preferred embodiment, it is the 3' end of the signalling probe that is attached to the bead (although as will be appreciated by those in the art, the system can be configured in a variety of different ways, including methods that would result in a loss of signal upon cleavage). Thus, the quencher molecule is located 5' to the cleavage site. Upon assembly of an assay complex, comprising the target sequence, an invader probe, and a signalling probe, and the introduction of the cleavage enzyme, the cleavage of the complex results in the disassociation of the quencher from the complex, resulting in an increase in fluorescence.

In this embodiment, suitable fluorophore-quencher pairs are as known in the art. For example, suitable quencher molecules comprise Dabcyl.

Combination Techniques

It is also possible to combine two or more of these techniques to do genotyping, quantification, detection of sequences, etc.

Novel Combination of Competitive Hybridization and Extension

In a preferred embodiment, a combination of competitive hybridization and extension, particularly SBE, is used. This may be generally described as follows. In this embodiment, different extension primers comprising different bases at the readout position are used, These are hybridized to a target sequence under stringency conditions that favor perfect matches, and then an extension reaction is done. Basically, the readout probe that has the match at the readout position will be preferentially extended for two reasons; first, the readout probe will hybridize more efficiently to the target (e.g. has a slower off rate), and the extension enzyme will preferentially add a nucleotide to a "hybridized" base. The reactions can then be detected in a number of ways, as outlined herein.

The system can take on a number of configurations, depending on the number of labels used, the use of adapters, whether a solution-based or surface-based assay is done, etc. Several preferred embodiments are shown in FIG. 14.

In a preferred embodiment, at least two different readout probes are used, each with a different base at the readout position and each with a unique detectable label that allows the identification of the base at the readout position. As described herein, these detectable labels may be either primary or secondary labels, with primary labels being preferred. As for all the competitive hybridization reactions, a competition for hybridization exists with the reaction conditions being set to favor match over mismatch. When the correct match occurs, the 3' end of the hybridization complex is now double stranded and thus serves as a template for an extension enzyme to add at least one base to the probe, at a position adjacent to the readout position. As will be appreciated by those in the art, for most SNP analysis, the nucleotide next to the detection position will be the same in all the reactions.

In one embodiment, chain terminating nucleotides may be used; alternatively, non-terminating nucleotides may be used and multiple nucleotides may be added, if desired. The latter may be particularly preferred as an amplification step of sorts; if the nucleotides are labelled, the addition of multiple labels can result in signal amplification.

In a preferred embodiment, the nucleotides are analogs that allow separation of reacted and unreacted primers as described herein; for example, this may be done by using a nuclease blocking moiety to protect extended primers and allow preferentially degradation of unextended primers or biotin (or iminobiotin) to preferentially remove the extended primers (this is done in a solution based assay, followed by elution and addition to the array).

As for the other reactions outlined herein, this may be done as a solution based assay, or a solid phase assay. Solution based assays are generally depicted in FIGS. 14A, 14B and 14C. In a solid phase reaction, an example of which is depicted in FIG. 14D, the capture probe serves as the readout probe; in this embodiment, different positions on the array (e.g. different beads) comprise different readout probes. That is, at least two different capture/readout probes are used, with three and four also possible, depending on the allele. The reaction is run under conditions that favor the formation of perfect match hybridization complexes. In this embodiment, the dNTPs comprise a detectable label, preferably a primary label such as a fluorophore. Since the competitive readout probes are spatially defined in the array, one fluorescent label can distinguish between the alleles; furthermore, it is the same nucleotide that is being added in the reaction, since it is the position adjacent to the SNP that is being extended. As for all the competitive assays, relative fluorescence intensity distinguishes between the alleles and between homozygosity and heterozygosity. In addition, multiple extension reactions can be done to amplify the signal.

For both solution and solid phase reactions, adapters may be additionally used. In a preferred embodiment, as shown in FIG. 14B for the solution based assay (although as will be appreciated by those in the art, a solid phase reaction may be done as well), adapters on the 5' ends of the readout probes are used, with identical adapters used for each allele. Each readout probe has a unique detectable label that allows the determination of the base at the readout position. After hybridization and extension, the readout probes are added to the array; the adapter sequences direct the probes to particular array locations and the relative intensities of the two labels distinguishes between alleles.

Alternatively, as depicted in FIG. 14C for the solution based assay (although as will be appreciated by those in the art, a solid phase reaction may be done as well), a different adapter may be used for each readout probe. In this embodiment, a single label may be used, since spatial resolution is used to distinguish the alleles by having a unique adapter attached to each allelic probe. After hybridization and extension, the readout probes are added to the array; the unique adapter sequences direct the probes to unique array locations. In this embodiment, it is the relative intensities of two array positions that distinguishes between alleles.

As will be appreciated by those in the art, any array may be used in this novel method, including both ordered and random arrays. In a preferred embodiment, the arrays may be made through spotting techniques, photolithographic techniques, printing techniques, or preferably are bead arrays.

Combination of Competitive Hybridization and Invasive Cleavage

In a preferred embodiment, a combination of competitive hybridization and invasive cleavage is done. As will be appreciated by those in the art, this technique is invasive cleavage as described above, with at least two sets of probes comprising different bases in the readout position. By running the reactions under conditions that favor hybridization complexes with perfect matches, different alleles may be distinguished.

In a preferred embodiment, this technique is done on bead arrays.

Novel Combination of Invasive Cleavage and Ligation

In a preferred embodiment, invasive cleavage and ligation is done, as is generally depicted in FIG. 15. In this embodiment, the specificity of the invasive cleavage reaction is used to detect the nucleotide in the detection position, and the specificity of the ligase reaction is used to ensure that only cleaved probes give a signal; that is, the ligation reaction confers an extra level of specificity.

The detection sequence, comprising a detectable label, of the signal probe is cleaved if the correct basepairing is present, as outlined above. The detection sequence then serves as the "target sequence" in a secondary reaction for detection; it is added to a capture probe on a microsphere. The capture probe in this case comprises a first double stranded portion and a second single stranded portion that will hybridize to the detection sequence. Again, preferred embodiments utilize adjacent portions, although dNTPs and a polymerase to fill in the "gap" may also be done. A ligase is then added. As shown in FIG. 15A, only if the signal probe has been cleaved will ligation occur; this results in covalent attachment of the signal probe to the array. This may be detected as outlined herein; preferred embodiments utilize stringency conditions that will discriminate between the ligated and unligated systems.

As will be appreciated by those in the art, this system may take on a number of configurations, including solution based and solid based assays. In a preferred embodiment, as outlined above, the system is configured such that only if cleavage occurs will ligation happen. In a preferred embodiment, this may be done using blocking moieties; the technique can generally be described as follows. An invasive cleavage reaction is done, using a signalling probe that is blocked at the 3' end. Following cleavage, which creates a free 3' terminus, a ligation reaction is done, generally using a template target and a second ligation probe comprising a detectable label. Since the signalling probe has a blocked 3' end, only those probes undergoing cleavage get ligated and labelled.

Alternatively, the orientations may be switched; in this embodiment, a free 5' phosphate is generated and is available for labeling.

Accordingly, in this embodiment, a solution invasive cleavage reaction is done (although as will be appreciated by those in the art, a support bound invasive cleavage reaction may be done as well).

As will be appreciated by those in the art, any array may be used in this novel method, including both ordered (predefined) and random arrays. In a preferred embodiment, the arrays may be made through spotting techniques, photolithographic techniques, printing techniques, or preferably are bead arrays.

Combination of Invasive Cleavage and Extension

In a preferred embodiment, a combination of invasive cleavage and extension reactions are done, as generally depicted in FIG. 16. The technique can generally be described as follows. An invasive cleavage reaction is done, using a signalling probe that is blocked at the 3' end. Following cleavage, which creates a free 3' terminus, an extension reaction is done (either enzymatically or chemically) to add a detectable label. Since the signalling probe has a blocked 3' end, only those probes undergoing cleavage get labelled.

Alternatively, the orientations may be switched, for example when chemical extension or labeling is done. In this embodiment, a free 5' phosphate is generated and is available for labeling.

In a preferred embodiment, the invasive cleavage reaction is configured as shown in FIG. 16B. In this embodiment, the signalling probe is attached to the array at the 5' end (e.g. to the detection sequence) and comprises a blocking moiety at the 3' end. The blocking moiety serves to prevent any alteration (including either enzymatic alteration or chemical alteration) of the 3' end. Suitable blocking moieties include, but are not limited to, chain terminators, alkyl groups, halogens; basically any non-hydroxy moiety.

Upon formation of the assay complex comprising the target sequence, the invader probe, and the signalling probe, and the introduction of the cleavage enzyme, the portion of the signalling probe comprising the blocking moiety is removed. As a result, a free 3' OH group is generated. This can be extended either enzymatically or chemically, to incorporate a detectable label. For example, enzymatic extension may occur. In a preferred embodiment, a non-templated extension occurs, for example, through the use of terminal transferase. Thus, for example, a modified dNTP may be incorporated, wherein the modification comprises the presence of a primary label such as a fluor, or a secondary label such as biotin, followed by the addition of a labeled streptavidin, for example. Similarly, the addition of a template (e.g. a secondary target sequence that will hybridize to the detection sequence attached to the bead) allows the use of any number of reactions as outlined herein, such as simple extension, SBE, pyrosequencing, OLA, etc. Again, this generally (but not always) utilizes the incorporation of a label into the growing strand.

Alternatively, as will be appreciated by those in the art, chemical labelling or extension methods may be used to label the 3' OH group.

As for all the combination methods, there are several advantages to this method. First of all, the absence of any label on the surface prior to cleavage allows a high signal-to-noise ratio. Additionally, the signalling probe need not contain any labels, thus making synthesis easier. Furthermore, because the target-specific portion of the signalling probe is removed during the assay, the remaining detection sequence can be any sequence. This allows the use of a common sequence for all beads; even if different reactions are carried out in parallel on the array, the post-cleavage detection can be identical for all assays, thus requiring only one set of reagents. As will be appreciated by those in the art, it is also possible to have different detection sequences if required. In addition, since the label is attached post-cleavage, there is a great deal of flexibility in the type of label that may be incorporated. This can lead to significant signal amplification; for example, the use of highly labeled streptavidin bound to a biotin on the detection sequence can give an increased signal per detection sequence. Similarly, the use of enzyme labels such as alkaline phosphatase or horseradish peroxidase allow signal amplification as well.

A further advantage is the two-fold specificity that is built into the assay. By requiring specificity at the. cleavage step, followed by specificity at the extension step, increased signal-to-noise ratios are seen.

As will be appreciated by those in the art, while generally described as a solid phase assay, this reaction may also be done in solution; this is similar to the solution-based SBE reactions, wherein the detection sequence serves as the extension primer. This assay also may be performed with an extension primer/adaptor oligonucleotide as described for solution-based SBE assays. It should be noted that the arrays used to detect the invasive cleavage/extension reactions may be of any type, including, but not limited to, spotted and printed arrays, photolithographic arrays, and bead arrays.

Combination of Ligation and Extension

In a preferred embodiment, OLA and SBE are combined, as is sometimes referred to as "Genetic Bit" analysis and described in Nikforov et al., Nucleic Acid Res. 22:4167 (1994), hereby expressly incorporated by reference. In this embodiment, the two ligation probes do not hybridize adjacently; rather, they are separated by one or more bases. The addition of dNTPs and a polymerase, in addition to the ligation probes and the ligase, results in an extended, ligated probe. As for SBE, the dNTPs may carry different labels, or separate reactions can be run, if the SBE portion of the reaction is used for genotyping. Alternatively, if the ligation portion of the reaction is used for genotyping, either no extension occurs due to mismatch of the 3' base (such that the polymerase will not extend it), or no ligation occurs due to mismatch of the 5' base. As will be appreciated by those in the art, the reaction products are assayed using microsphere arrays. Again, as outlined herein, the assays may be solution based assays, with the ligated, extended probes being added to a microsphere array, or solid-phase assays. In addition, the unextended, unligated primers may be removed prior to detection as needed, as is outlined herein. Furthermore, adapter sequences may also be used as outlined herein for OLA.

Combination of OLA and PCR

In a preferred embodiment, OLA and PCR are combined. As will be appreciated by those in the art, the sequential order of the reaction is variable. That is, in some embodiments it is desired to perform the genotyping or OLA reaction first followed by PCR amplification. In an alternative embodiment, it is desirable to first amplify the target i.e. by PCR followed by the OLA assay.

In a preferred embodiment, this technique is done on bead arrays.

Combination of Competitive Hybridization and Ligation

In a preferred embodiment, a combination of competitive hybridization and ligation is done. As will be appreciated by those in the art, this technique is OLA as described above, with at least two sets of probes comprising different bases in the readout position. By running the reactions under conditions that favor hybridization complexes with perfect matches, different alleles may be distinguished.

In one embodiment, LCR is used to genotype a single genomic locus by incorporating two sets of two optically labeled AS oligonucleotides and a detection oligonucleotide in the ligation reaction. The oligonucleotide ligation step discriminates between the AS oligonucleotides through the efficiency of ligation between an oligonucleotide with a correct match with the target nucleic acid versus a mismatch base in the target nucleic acid at the ligation site. Accordingly, a detection oligonucleotide ligates efficiently to an AS oligonucleotide if there is complete base pairing at the ligation site. One 3' oligonucleotide (T base at 5' end) is optically labeled with FAM (green fluorescent dye) and the other 3' oligonucleotide (C base at 5' end) is labelled with TMR (yellow fluorescent dye). An A base in the target nucleic acid base pairs with the corresponding T resulting in efficient ligation of the FAM-labeled oligonucleotide. A G base in the target nucleic acid results in ligation of the TMR-labeled oligonucleotide. TMR and FAM have distinct emission spectrums. Accordingly, the wavelength of the oligonucleotide ligated to the 5' detection oligonucleotide indicates the nucleotide and thus the genotype of the target nucleic acid.

In a preferred embodiment, this technique is done on bead arrays.

Combination of Competitive Hybridization and Invasive Cleavage

In a preferred embodiment, a combination of competitive hybridization and invasive cleavage is done. As will be appreciated by those in the art, this technique is invasive cleavage as described above, with at least two sets of probes (either the invader probes or the signalling probes) comprising different bases in the readout position. By running the reactions under conditions that favor hybridization complexes with perfect matches, different alleles may be distinguished.

In a preferred embodiment, this technique is done on bead arrays.

In addition to the amplification and genotyping embodiments disclosed herein, the present invention further provides compositions and methods for nucleic acid sequencing.

Sequencing

The present invention is directed to the sequencing of nucleic acids, particularly DNA, by synthesizing nucleic acids using the target sequence (i.e. the nucleic acid for which the sequence is determined) as a template. These methods can be generally described as follows. A target sequence is attached to a solid support, either directly or indirectly, as outlined below. The target sequence comprises a first domain and an adjacent second domain comprising target positions for which sequence information is desired. A sequencing primer is hybridized to the first domain of the target sequence, and an extension enzyme is added, such as a polymerase or a ligase, as outlined below. After the addition of each base, the identity of each newly added base is determined prior to adding the next base. This can be done in a variety of ways, including controlling the reaction rate and using a fast detector, such that the newly added bases are identified in real time. Alternatively, the addition of nucleotides is controlled by reversible chain termination, for example through the use of photocleavable blocking groups. Alternatively, the addition of nucleotides is controlled, so that the reaction is limited to one or a few bases at a time. The reaction is restarted after each cycle of addition and reading. Alternatively, the addition of nucleotides is accomplished by carrying out a ligation reaction with oligonucleotides comprising chain terminating oligonucleotides. Preferred methods of sequencing-by-synthesis include, but are not limited to, pyrosequencing, reversible-chain termination sequencing, time-resolved sequencing, ligation sequencing, and single-molecule analysis, all of which are described below.

The advantages of these "sequencing-by-synthesis" reactions can be augmented through the use of array techniques that allow very high density arrays to be made rapidly and inexpensively, thus allowing rapid and inexpensive nucleic acid sequencing. By "array techniques" is meant techniques that allow for analysis of a plurality of nucleic acids in an array format. The maximum number of nucleic acids is limited only by the number of discrete loci on a particular array platform. As is more fully outlined below, a number of different array formats can be used.

The methods of the invention find particular use in sequencing a target nucleic acid sequence, i.e. identifying the sequence of a target base or target bases in a target nucleic acid, which can ultimately be used to determine the sequence of long nucleic acids.

As is outlined herein, the target sequence comprises positions for which sequence information is desired, generally referred to herein as the "target positions". In one embodiment, a single target position is elucidated; in a preferred embodiment, a plurality of target positions are elucidated. In general, the plurality of nucleotides in the target positions are contiguous with each other, although in some circumstances they may be separated by one or more nucleotides. By "plurality" as used herein is meant at least two. As used herein, the base which basepairs with the target position base in a hybrid is termed the "sequence position". That is, as more fully outlined below, the extension of a sequence primer results in nucleotides being added in the sequence positions, that are perfectly complementary to the nucleotides in the target positions. As will be appreciated by one of ordinary skill in the art, identification of a plurality of target positions in a target nucleotide sequence results in the determination of the nucleotide sequence of the target nucleotide sequence.

As will be appreciated by one of ordinary skill in the art, this system can take on a number of different configurations, depending on the sequencing method used, the method of attaching a target sequence to a surface, etc. In general, the methods of the invention rely on the attachment of different target sequences to a solid support (which, as outlined below, can be accomplished in a variety of ways) to form an array. The target sequences comprise at least two domains: a first domain, for which sequence information is not desired, and to which a sequencing primer can hybridize, and a second domain, adjacent to the first domain, comprising the target positions for sequencing. A sequencing primer is hybridized to the target sequence, forming a hybridization complex, and then the sequencing primer is enzymatically extended by the addition of a first nucleotide into the first sequence position of the primer. This first nucleotide is then identified, as is outlined below, and then the process is repeated, to add nucleotides to the second, third, fourth, etc. sequence positions. The exact methods depend on the sequencing technique utilized, as outlined below.

Once the target sequence is associated onto the array as outlined below, the target sequence can be used in a variety of sequencing by synthesis reactions. These reactions are generally classified into several categories, outlined below.

Sequencing by Synthesis

As outlined herein, a number of sequencing by synthesis reactions are used to elucidate the identity of a plurality of bases at target positions within the target sequence. All of these reactions rely on the use of a target sequence comprising at least two domains; a first domain to which a sequencing primer will hybridize, and an adjacent second domain, for which sequence information is desired. Upon formation of the assay complex, extension enzymes are used to add dNTPs to the sequencing primer, and each addition of dNTP is "read" to determine the identity of the added dNTP. This may proceed for many cycles.

Pyrosequencing

In a preferred embodiment, pyrosequencing methods are done to sequence the nucleic acids. As outlined above, pyrosequencing is an extension method that can be used to add one or more nucleotides to the target positions. Pyrosequencing relies on the detection of a reaction product, pyrophosphate (PPi), produced during the addition of an NTP to a growing oligonucleotide chain, rather than on a label attached to the nucleotide. One molecule of PPi is produced per dNTP added to the extension primer. The detection of the PPi produced during the reaction is monitored using secondary enzymes; for example, preferred embodiments utilize secondary enzymes that convert the PPi into ATP, which also may be detected in a variety of ways, for example through a chemiluminescent reaction using luciferase and luciferin, or by the detection of NADPH. Thus, by running sequential reactions with each of the nucleotides, and monitoring the reaction products, the identity of the added base is determined.

Accordingly, the present invention provides methods of pyrosequencing on arrays; the arrays may be any number of different array configurations and substrates, as outlined herein, with microsphere arrays being particularly preferred. In this embodiment, the target sequence comprises a first domain that is substantially complementary to a sequencing primer, and an adjacent second domain that comprises a plurality of target positions. By "sequencing primer" herein is meant a nucleic acid that is substantially complementary to the first target domain, with perfect complementarity being preferred. As will be appreciated by those in the art, the length of the sequencing primer will vary with the conditions used. In general, the sequencing primer ranges from about 6 to about 500 or more basepairs in length, with from about 8 to about 100 being preferred, and from about 10 to about 25 being especially preferred.

Once the sequencing primer is added and hybridized to the target sequence to form a first hybridization complex (also sometimes referred to herein as an "assay complex"), the system is ready to initiate sequencing-by-synthesis. The methods described below make reference to the use of fiber optic bundle substrates with associated microspheres, but as will be appreciated by those in the art, any number of other substrates or solid supports may be used, or arrays that do not comprise microspheres.

The reaction is initiated by introducing the substrate comprising the hybridization complex comprising the target sequence (i.e. the array) to a solution comprising a first nucleotide, generally comprising deoxynucleoside-triphosphates (dNTPs). Generally, the dNTPs comprise dATP, dTTP, dCTP and dGTP. The nucleotides may be naturally occurring, such as deoxynucleotides, or non-naturally occurring, such as chain terminating nucleotides including dideoxynucleotides, as long as the enzymes used in the sequencing/detection reactions are still capable of recognizing the analogs. In addition, as more fully outlined below, for example in other sequencing-by-synthesis reactions, the nucleotides may comprise labels. The different dNTPs are added either to separate aliquots of the hybridization complex or preferably sequentially to the hybridization complex, as is more fully outlined below. In some embodiments it is important that the hybridization complex be exposed to a single type of dNTP at a time.

In addition, as will be appreciated by those in the art, the extension reactions of the present invention allow the precise incorporation of modified bases into a growing nucleic acid strand. Thus, any number of modified nucleotides may be incorporated for any number of reasons, including probing structure-function relationships (e.g. DNA:DNA or DNA:protein interactions), cleaving the nucleic acid, crosslinking the nucleic acid, incorporate mismatches, etc.

In addition to a first nucleotide, the solution also comprises an extension enzyme, generally a DNA polymerase. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase. If the dNTP is complementary to the base of the target sequence adjacent to the extension primer, the extension enzyme will add it to the extension primer, releasing pyrophosphate (PPi). Thus, the extension primer is modified, i.e. extended, to form a modified primer, sometimes referred to herein as a "newly synthesized strand". The incorporation of a dNTP into a newly synthesized nucleic acid strand releases PPi, one molecule of PPi per dNTP incorporated.

The release of pyrophosphate (PPi) during the DNA polymerase reaction can be quantitatively measured by many different methods and a number of enzymatic methods have been described; see Reeves at al., Anal. Biochem. 28:282 (1969); Guillory et al., Anal. Biochem. 39:170 (1971); Johnson et al., Anal. Biochem. 15:273 (1968); Cook at al., Anal. Biochem. 91:557 (1978); Drake at al., Anal. Biochem. 94:117 (1979); Ronaghi et al. Science 281:363 (1998); Barshop et al., Anal. Biochem. 197(1):266-272 (1991) WO93/23564; WO 98/28440; WO98/13523; Nyren et al., Anal. Biochem. 151:504 (1985); all of which are incorporated by reference. The latter method allows continuous monitoring of PPi and has been termed ELIDA (Enzymatic Luminometric Inorganic Pyrophosphate Detection Assay). In a preferred embodiment, the PPi is detected utilizing UDP-glucose pyrophosphorylase, phosphoglucomutase and glucose 6-phosphate dehydrogenase. See Justesen, et al., Anal. Biochem. 207(1):90-93 (1992); Lust et al., Clin. Chem. Acta 66(2):241 (1976); and Johnson et al., Anal. Biochem. 26:137 (1968); all of which are hereby incorporated by reference. This reaction produces NADPH which can be detected fluoremetrically. A preferred embodiment utilizes any method which can result in the generation of an optical signal, with preferred embodiments utilizing the generation of a chemiluminescent or fluorescent signal.

Generally, these methods rely on secondary enzymes to detect the PPi; these methods generally rely on enzymes that will convert PPi into ATP, which can then be detected. A preferred method monitors the creation of PPi by the conversion of PPi to ATP by the enzyme sulfurylase, and the subsequent production of visible light by firefly luciferase (see Ronaghi at al., supra, and Barshop, supra). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase (and its substrate, adenosine 5'-phosphosulphate (APS)) luciferase (and its substrate luciferin), and optionally a nucleotide-degrading enzyme such as apyrase. A dNTP is only incorporated into the growing DNA strand if it is complementary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

As will be appreciated by those in the art, if the target sequence comprises two or more of the same nucleotide in a row, more than one dNTP will be incorporated; however, the amount of PPi generated is directly proportional to the number of dNTPs incorporated and thus these sequences can be detected.

In addition, in a preferred embodiment, the dATP that is added to the reaction mixture is an analog that can be incorporated by the DNA polymerase into the growing oligonucleotide strand, but will not serve as a substrate for the second enzyme; for example, certain thiol-containing dATP analogs find particular use.

Accordingly, a preferred embodiment of the methods of the invention is as follows. A substrate comprising microspheres containing the target sequences and extension primers, forming hybridization complexes, is dipped or contacted with a volume (reaction chamber or well) comprising a single type of dNTP, an extension enzyme, and the reagents and enzymes necessary to detect PPi. If the dNTP is complementary to the base of the target portion of the target sequence adjacent to the extension primer, the dNTP is added, releasing PPi and generating detectable light, which is detected as generally described in U.S. Ser. Nos. 09/151,877 and 09/189,543, and PCT US98/09163, all of which are hereby incorporated by reference. If the dNTP Is not complementary, no detectable signal results. The substrate is then contacted with a second reaction chamber comprising a different dNTP and the additional components of the assay. This process is repeated to generate a readout of the sequence of the target sequence.

In a preferred embodiment, washing steps, i.e. the use of washing chambers, may be done in between the dNTP reaction chambers, as required. These washing chambers may optionally comprise a nucleotide-degrading enzyme, to remove any unreacted dNTP and decreasing the background signal, as is described in WO 98/28440, incorporated herein by reference. In a preferred embodiment a flow cell is used as a reaction chamber; following each reaction the unreacted dNTP is washed away and may be replaced with an additional dNTP to be examined.

As will be appreciated by those in the art, the system can be configured in a variety of ways, including both a linear progression or a circular one; for example, four substrates may be used that each can dip into one of four reaction chambers arrayed in a circular pattern. Each cycle of sequencing and reading is followed by a 90 degree rotation, so that each substrate then dips into the next reaction well. This allows a continuous series of sequencing reactions on multiple substrates in parallel.

In a preferred embodiment, one or more internal control sequences are used. That is, at least one microsphere in the array comprises a known sequence that can be used to verify that the reactions are proceeding correctly. In a preferred embodiment, at least four control sequences are used, each of which has a different nucleotide at each position: the first control sequence will have an adenosine at position 1, the second will have a cytosine, the third a guanosine, and the fourth a thymidine, thus ensuring that at least one control sequence is "lighting up" at each step to serve as an internal control.

In a preferred embodiment, the reaction is run for a number of cycles until the signal-to-noise ratio becomes low, generally from 20 to 70 cycles or more, with from about 30 to 50 being standard. in some embodiments, this is sufficient for the purposes of the experiment; for example, for the detection of certain mutations, including single nucleotide polymorphisms (SNPs), the experiment is designed such that the initial round of sequencing gives the desired information. In other embodiments, it is desirable to sequence longer targets, for example in excess of hundreds of bases. In this application, additional rounds of sequencing can be done.

For example, after a certain number of cycles, it is possible to stop the reaction, remove the newly synthesized strand using either a thermal step or a chemical wash, and start the reaction over, using for example the sequence information that was previously generated to make a new extension primer that will hybridize to the first target portion of the target sequence. That is, the sequence information generated in the first round is transferred to an oligonucleotide synthesizer, and a second extension primer is made for a second round of sequencing. In this way, multiple overlapping rounds of sequencing are used to generate long sequences from template nucleic acid strands. Alternatively, when a single target sequence contains a number of mutational "hot spots", primers can be generated using the known sequences in between these hot spots.

Additionally, the methods of the invention find use in the decoding of random microsphere arrays. That is, as described in U.S. Ser. No. 09/189,543, nucleic acids can be used as bead identifiers. By using sequencing-by-synthesis to read out the sequence of the nucleic acids, the beads can be decoded in a highly parallel fashion.

In addition, the methods find use in simultaneous analysis of multiple target sequence positions on a single array. For example, four separate sequence analysis reactions are performed. In the first reaction, positions containing a particular nucleotide ("A", for example) in the target sequence are analyzed. In three other reactions, C, G, and T are analyzed. An advantage of analyzing one base per reaction is that the baseline or background is flattened for the three bases excluded from the reaction. Therefore, the signal is more easily detected and the sensitivity of the assay is increased. Alternatively, each of the four sequencing reactions (A, G, C and T) can be performed simultaneously with a nested set of primers providing a significant advantage in that primer synthesis can be made more efficient.

In another preferred embodiment each probe is represented by multiple beads in the array (see U.S. Ser. No. 09/287,573, filed Apr. 6, 1999, hereby expressly incorporated by reference). As a result, each experiment can be replicated many times in parallel. As outlined below, averaging the signal from each respective probe in an experiment also allows for improved signal to noise and increases the sensitivity of detecting subtle perturbations in signal intensity patterns. The use of redundancy and comparing the patterns obtained from two different samples (e.g. a reference and an unknown), results in highly paralleled and comparative sequence analysis that can be performed on complex nucleic acid samples.

As outlined herein, the pyrosequencing systems may be configured in a variety of ways; for example, the target sequence may be attached to the array (e.g. the beads) in a variety of ways, including the direct attachment of the target sequence to the array; the use of a capture probe with a separate extension probe; the use of a capture extender probe, a capture probe and a separate extension probe; the use of adapter sequences in the target sequence with capture and extension probes; and the use of a capture probe that also serves as the extension probe.

In addition, as will be appreciated by those in the art, the target sequence may comprise any number of sets of different first and second target domains; that is, depending on the number of target positions that may be elucidated at a time, there may be several "rounds" of sequencing occurring, each time using a different target domain.

One additional benefit of pyrosequencing for genotyping purposes is that since the reaction does not rely on the incorporation of labels into a growing chain, the unreacted extension primers need not be removed.

Thus, pyrosequencing kits and reactions require, in no particularly order, arrays comprising capture probes, sequencing primers, an extension enzyme, and secondary enzymes and reactants for the detection of PPi, generally comprising enzymes to convert PPi into ATP (or other NTPs), and enzymes and reactants to detect ATP.

Attachment of Enzymes to Arrays

In a preferred embodiment, particularly when secondary enzymes (i.e. enzymes other than extension enzymes) are used in the reaction, the enzyme(s) may be attached, preferably through the use of flexible linkers, to the sites on the array, e.g. the beads. For example, when pyrosequencing is done, one embodiment utilizes detection based on the generation of a chemiluminescent signal in the "zone" around the bead. By attaching the secondary enzymes required to generate the signal, an increased concentration of the required enzymes is obtained in the immediate vicinity of the reaction, thus allowing for the use of less enzyme and faster reaction rates for detection. Thus, preferred embodiments utilize the attachment, preferably covalently (although as will be appreciated by those in the art, other attachment mechanisms may be used), of the non-extension secondary enzymes used to generate the signal. In some embodiments, the extension enzyme (e.g. the polymerase) may be attached as well, although this is not generally preferred.

The attachment of enzymes to array sites, particularly beads, is outlined in U.S. Ser. No. 09/287,573, hereby incorporated by reference, and will be appreciated by those in the art. in general, the use of flexible linkers are preferred, as this allows the enzymes to interact with the substrates. However, for some types of attachment, linkers are not needed. Attachment proceeds on the basis of the composition of the array site (i.e. either the substrate or the bead, depending on which array system is used) and the composition of the enzyme. In a preferred embodiment, depending on the composition of the array site (e.g. the bead), it will contain chemical functional groups for subsequent attachment of other moieties. For example, beads comprising a variety of chemical functional groups such as amines are commercially available. Preferred functional groups for attachment are amino groups, carboxy groups, oxo groups and thiol groups, with amino groups being particularly preferred. Using these functional groups, the enzymes can be attached using functional groups on the enzymes. For example, enzymes containing amino groups can be attached to particles comprising amino groups, for example using linkers as are known in the art; for example, homo- or hetero-bifunctional linkers are well known (see 1994 Pierce Chemical Company catalog, technical section on cross-linkers, pages 155-200, incorporated herein by reference).

Reversible Chain Termination Methods

In a preferred embodiment, the sequencing-by-synthesis method utilized is reversible chain termination. In this embodiment, the rate of addition of dNTPs is controlled by using nucleotide analogs that contain a removable protecting group at the 3' position of the dNTP. The presence of the protecting group prevents further addition of dNTPs at the 3' end, thus allowing time for detection of the nucleotide added (for example, utilizing a labeled dNTP). After acquisition of the identity of the dNTP added, the protecting group is removed and the cycle repeated. In this way, dNTPs are added one at a time to the sequencing primer to allow elucidation of the nucleotides at the target positions. See U.S. Pat. Nos. 5,902,723; 5,547,839; Metzker et al., Nucl. Acid Res. 22(20): 4259 (1994); Canard et al., Gene 148(1):1-6 (1994); Dyatkina et al., Nucleic Acid Symp. Ser. 18:117-120 (1987); all of which are hereby expressly incorporated by reference.

Accordingly, the present invention provides methods and compositions for reversible chain termination sequencing-by-synthesis. Similar to pyrosequencing, the reaction requires the hybridization of a substantially complementary sequencing primer to a first target domain of a target sequence to form an assay complex.

The reaction is initiated by introducing the assay complex comprising the target sequence (i.e. the array) to a solution comprising a first nucleotide analog. By "nucleotide analog" in this context herein is meant a deoxynucleoside-triphosphate (also called deoxynucleotides or dNTPs, i.e. dATP, dTTP, dCTP and dGTP), that is further derivatized to be reversibly chain terminating. As will be appreciated by those in the art, any number of nucleotide analogs may be used, as long as a polymerase enzyme will still incorporate the nucleotide at the sequence position. Preferred embodiments utilize 3'—O-methyl-dNTPs (with photolytic removal of the protecting group), 3'-substituted-2'-dNTPs that contain anthranylic derivatives that are fluorescent (with alkali or enzymatic treatment for removal of the protecting group). The latter has the advantage that the protecting group is also the fluorescent label; upon cleavage, the label is also removed, which may serve to generally lower the background of the assay as well.

Again, the system may be configured and/or utilized in a number of ways. In a preferred embodiment, a set of nucleotide analogs such as derivatized dATP, derivatized dCTP, derivatized dGTP and derivatized dTTP is used, each with a different detectable and resolvable label, as outlined below. Thus, the identification of the base at the first sequencing position can be ascertained by the presence of the unique label.

Alternatively, a single label is used but the reactions are done sequentially. That is, the substrate comprising the array is first contacted with a reaction mixture of an extension enzyme and a single type of base with a first label, for example ddATP. The incorporation of the ddATP is monitored at each site on the array. The substrate is then contacted (with optional washing steps as needed) to a second reaction mixture comprising the extension enzyme and a second nucleotide, for example ddTTP. The reaction is then monitored; this can be repeated for each target position.

Once each reaction has been completed and the identification of the base at the sequencing position is ascertained, the terminating protecting group is removed, e.g. cleaved, leaving a free 3' end to repeat the sequence, using an extension enzyme to add a base to the 3' end of the sequencing primer when it is hybridized to the target sequence. As will be appreciated by those in the art, the cleavage conditions will vary with the protecting group chosen.

In a preferred embodiment, the nucleotide analogs comprise a detectable label as described herein, and this may be a primary label (directly detectable) or a secondary label (indirectly detectable).

In addition to a first nucleotide, the solution also comprises an extension enzyme, generally a DNA polymerase, as outlined above for pyrosequencing.

In a preferred embodiment, the protecting group also comprises a label. That is, as outlined in Canard et al., supra, the protecting group can serve as either a primary or secondary label, with the former being preferred. This is particularly preferred as the removal of the label at each round results in less background noise, less quenching and less crosstalk.

In this way, reversible chain termination sequencing is accomplished.

Time-resolved Sequencing

In a preferred embodiment, time-resolved sequencing is done. This embodiment relies on controlling the reaction rate of the extension reaction and/or using a fast imaging system. Basically, the method involves a simple extension reaction that is either "slowed down", or imaged using a fast system, or both. What is important is that the rate of polymerization (extension) is significantly slower than the rate of image capture.

To allow for real time sequencing, parameters such as the speed of the detector (millisecond speed is preferred), and rate of polymerization will be controlled such that the rate of polymerization is significantly slower than the rate of image capture. Polymerization rates on the order of kilobases per minute (e.g. −10 milliseconds/nucleotide), which can be adjusted, should allow a sufficiently wide window to find conditions where the sequential addition of two nucleotides can be resolved. The DNA polymerization reaction, which has been studied intensively, can easily be reconstituted in vitro and controlled by varying a number of parameters including reaction temperature and the concentration of nucleotide triphosphates.

In addition, the polymerase can be applied to the primer-template complex prior to initiating the reaction. This serves to synchronize the reaction. Numerous polymerases are available. Some examples include, but are not limited to polymerases with 3' to 5' exonuclease activity, other nuclease activities, polymerases with different processivity, affinities for modified and unmodified nucleotide triphosphates, temperature optima, stability, and the like.

Thus, in this embodiment, the reaction proceeds as outlined above. The target sequence, comprising a first domain that will hybridize to a sequencing primer and a second domain comprising a plurality of target positions, is attached to an array as outlined below. The sequencing primers are added, along with an extension enzyme, as outlined herein, and dNTPs are added. Again, as outlined above, either four differently labeled dNTPs may be used simultaneously or, four different sequential reactions with a single label are done. In general, the dNTPs comprise either a primary or a secondary label, as outlined above.

In a preferred embodiment, the extension enzyme is one that is relatively "slow". This may be accomplished in several ways. In one embodiment, polymerase variants are used that have a lower polymerization rate than wild-type enzymes. Alternatively, the reaction rate may be controlled by varying the temperature and the concentration of dNTPs.

In a preferred embodiment, a fast (millisecond) high-sensitivity imaging system is used.

In one embodiment, DNA polymerization (extension) is monitored using light scattering, as is outlined in Johnson et al., Anal. Biochem. 136(1):192 (1984), hereby expressly incorporated by reference.

Attachment of Target Sequences to Arrays

As is generally described herein, there are a variety of methods that can be used to attach target sequences to the solid supports of the invention, particularly to the microspheres that are distributed on a surface of a substrate. Most of these methods generally rely on capture probes attached to the array. However, the attachment may be direct or indirect. Direct attachment includes those situations wherein an endogeneous portion of the target sequence hybridizes to the capture probe, or where the target sequence has been manipulated to contain exogeneous adapter sequences that are added to the target sequence, for example during an amplification reaction. Indirect attachment utilizes one or more secondary probes, termed a "capture extender probe" as outlined herein.

In a preferred embodiment, direct attachment is done, as is generally depicted in FIG. 1A. In this embodiment, the target sequence comprises a first target domain that hybridizes to all or part of the capture probe.

In a preferred embodiment, direct attachment is accomplished through the use of adapters. The adapter is a chemical moiety that allows one to address the products of a reaction to a solid surface. The type of reaction includes the amplification, genotyping and sequencing reactions disclosed herein. The adapter chemical moiety is independent of the reaction. Because the adapters are independent of the reaction, sets of adapters can be reused to create a "universal" array that can detect a variety of products from a reaction by attaching the set of adapters that address to specific locations within the array to different reactants.

Typically, the adapter and the capture probe on an array are binding partners, as defined herein. Although the use of other binding partners are possible, preferred embodiments utilize nucleic acid adapters that are non-complementary to any reactants or target sequences, but are substantially complementary to all or part of the capture probe on the array.

Thus, an "adapter sequence" is a nucleic acid that is generally not native to the target sequence, i.e. is exogeneous, but is added or attached to the target sequence. it should be noted that in this context, the "target sequence" can include the primary sample target sequence, or can be a derivative target such as a reactant or product of the reactions outlined herein; thus for example, the target sequence can be a PCR product, a first ligation probe or a ligated probe in an OLA reaction, etc.

As will be appreciated by those in the art, the attachment, or joining, of the adapter sequence to the target sequence can be done in a variety of ways. In a preferred embodiment, the adapter sequences are added to the primers of the reaction (extension primers, amplification primers, readout probes, sequencing primers, Rolling Circle primers, etc.) during the chemical synthesis of the primers. The adapter then gets added to the reaction product during the reaction; for example, the primer gets extended using a polymerase to form the new target sequence that now contains an adapter sequence. Alternatively, the adapter sequences can be added enzymatically. Furthermore, the adapter can be attached to the target after synthesis; this post-synthesis attachment could be either covalent or non-covalent.

In this embodiment, one or more of the amplification primers comprises a first portion comprising the adapter sequence and a second portion comprising the primer sequence. Extending the amplification primer as is well known in the art results in target sequences that comprise the adapter sequences. The adapter sequences are designed to be substantially complementary to capture probes.

In addition, as will be appreciated by those in the art, the adapter can be attached either on the 3' or 5' ends, or in an internal position. For example, the adapter may be the detection sequence of an invasive cleavage probe. In the case of Rolling Circle probes, the adapter can be contained within the section between the probe ends. Adapters can also be attached to aptamers. Aptamers are nucleic acids that can be made to bind to virtually any target analyte; see Bock et al., Nature 355:564 (1992); Femulok et al., Current Op. Chem. Biol. 2:230 (1998); and U.S. Pat. Nos. 5,270,163, 5,475,096, 5,567,588, 5,595,877, 5,637,459, 5,683,867, 5,705,337, and related patents, hereby incorporated by reference. In addition, as outlined below, the adapter can be attached to non-nucleic acid target analytes as well.

In one embodiment, a set of probes is hybridized to a target sequence; each probe is complementary to a different region of a single target but each contains the same adapter. Using a poly-T bead, the mRNA target is pulled out of the sample with the probes attached. Dehybridizing the probes attached to the target sequence and rehybridizing them to an array containing the capture probes complementary to the adapter sequences results in binding to the array. All adapters that have bound to the same target mRNA will bind to the same location on the array.

In a preferred embodiment, indirect attachment of the target sequence to the array is done, through the use of capture extender probes. "Capture extender" probes are generally depicted in FIG. 1C, and other figures, and have a first portion that will hybridize to all or part of the capture probe, and a second portion that will hybridize to a first portion of the target sequence. Two capture extender probes may also be used. This has generally been done to stabilize assay complexes for example when the target sequence is large, or when large amplifier probes (particularly branched or dendrimer amplifier probes) are used.

When only capture probes are utilized, it is necessary to have unique capture probes for each target sequence; that is, the surface must be customized to contain unique capture probes; e.g. each bead comprises a different capture probe. In general, only a single type of capture probe should be bound to a bead; however, different beads should contain different capture probes so that different target sequences bind to different beads.

Alternatively, the use of adapter sequences and capture extender probes allow the creation of more "universal" surfaces. In a preferred embodiment, an array of different and usually artificial capture probes are made; that is, the capture probes do not have complementarity to known target sequences. The adapter sequences can then be added to any target sequences, or soluble capture extender probes are made; this allows the manufacture of only one kind of array, with the user able to customize the array through the use of adapter sequences or capture extender probes. This then allows the generation of customized soluble probes, which as will be appreciated by those in the art is generally simpler and less costly.

As will be appreciated by those in the art, the length of the adapter sequences will vary, depending on the desired "strength" of binding and the number of different adapters desired. In a preferred embodiment, adapter sequences range from about 6 to about 500 basepairs in length, with from about 8 to about 100 being preferred, and from about 10 to about 25 being particularly preferred.

In one embodiment, microsphere arrays containing a single type of capture probe are made; in this embodiment, the capture extender probes are added to the beads prior to loading on the array. The capture extender probes may be additionally fixed or crosslinked, as necessary.

In a preferred embodiment, as outlined in FIG. 1 B, the capture probe comprises the sequencing primer; that is, after hybridization to the target sequence, it is the capture probe itself that is extended during the synthesis reaction.

In one embodiment, capture probes are not used, and the target sequences are attached directly to the sites on the array. For example, libraries of clonal nucleic acids, including DNA and RNA, are used. In this embodiment, individual nucleic acids are prepared, generally using conventional methods (including, but not limited to, propagation in plasmid or phage vectors, amplification techniques including PCR, etc.). The nucleic acids are preferably arrayed in some format, such as a microtiter plate format, and either spotted or beads are added for attachment of the libraries.

Attachment of the clonal libraries (or any of the nucleic acids outlined herein) may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

In a preferred embodiment, affinity capture is used to attach the clonal nucleic acids to the surface. For example, cloned nucleic acids can be derivatized, for example with one member of a binding pair, and the beads derivatized with the other member of a binding pair. Suitable binding pairs are as described herein for secondary labels and IBL/DBL pairs. For example, the cloned nucleic acids may be biotinylated (for example using enzymatic incorporate of biotinylated nucleotides, for by photoactivated cross-linking of biotin). Biotinylated nucleic acids can then be captured on streptavidin coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, If there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach cloned nucleic acids to beads. For example, as is known in the art, polyA+RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

In general, special methods are required to decode clonal arrays, as is more fully outlined below.

Assay and Arrays

All of the above compositions and methods are directed to the detection and/or quantification of the products of nucleic acid reactions. The detection systems of the present invention are based on the incorporation (or in some cases, of the deletion) of a detectable label into an assay complex on an array.

Accordingly, the present invention provides methods and compositions useful in the detection of nucleic acids. As will be appreciated by those in the art, the compositions of the invention can take on a wide variety of configurations, as is generally outlined in the Figures. As is more fully outlined below, preferred systems of the invention work as follows. A target nucleic acid sequence is attached (via hybridization) to an array site. This attachment can be either directly to a capture probe on the surface, through the use of adapters, or indirectly, using capture extender probes as outlined herein. In some embodiments, the target sequence itself comprises the labels. Alternatively, a label probe is then added, forming an assay complex. The attachment of the label probe may be direct (i.e. hybridization to a portion of the target sequence), or indirect (i.e. hybridization to an amplifier probe that hybridizes to the target sequence), with all the required nucleic acids forming an assay complex.

Accordingly, the present invention provides array compositions comprising at least a first substrate with a surface comprising individual sites. By "array" or "biochip" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc. A preferred embodiment utilizes microspheres on a variety of substrates including fiber optic bundles, as are outlined in PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; all of which are expressly incorporated by reference. While much of the discussion below is directed to the use of microsphere arrays on fiber optic bundles, any array format of nucleic acids on solid supports may be utilized.

Arrays containing from about 2 different bioactive agents (e.g. different beads, when beads are used) to many millions can be made, with very large arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred (all numbers being in square cm). High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 μm or less (with beads of 200 nm possible) can be used, and very small fibers are known, it is possible to have as many as 40,000 or more (in some instances, 1 million) different elements (e.g. fibers and beads) in a 1 mm2 fiber optic bundle, with densities of greater than 25,000,000 individual beads and fibers (again, in some. instances as many as 50-100 million) per 0.5 $cm^2$ obtainable (4 million per square cm for 5μ center-to-center and 100 million per square cm for 1μ center-to-center).

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon. and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the array of array compositions of the invention can be configured in several ways; see for example U.S. Ser. No. 09/473,904, hereby expressly incorporated by reference. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below.

Alternatively, a "two component" system can be used. In this embodiment, the individual arrays are formed on a second substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate. By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In some embodiments, the beads are not associated with a substrate. That is, the beads are in solution or are not distributed on a patterned substrate.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each capture probe; preferred embodiments utilize a plurality of beads of each type.

By "microspheres" or "beads" or "particles" or grammatical equivalents herein is meant small discrete particles. The composition of the beads will vary, depending on the class of capture probe and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "Microsphere Detection Guide" from Bangs Laboratories, Fishers IN is a helpful guide.

The beads need not be spherical; irregular particles may be used. In addition, the beads may be porous, thus increasing the surface area of the bead available for either capture probe attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a capture probe, although as will be appreciated by those in the art, there may be some microspheres which do not contain a capture probe, depending on the synthetic methods.

Attachment of the nucleic acids may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc. In a preferred embodiment, affinity capture is used to attach the nucleic acids to the beads. For example, nucleic acids can be derivatized, for example with one member of a binding pair, and the beads derivatized with the other member of a binding pair. Suitable binding pairs are as described herein for IBL/DBL pairs. For example, the nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach nucleic acids to beads. For example, as is known in the art, polyA+RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

In general, probes of the present invention are designed to be complementary to a target sequence (either the target sequence of the sample or to other probe sequences, as is described herein), such that hybridization of the target and the probes of the present invention occurs. This complementarily need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions.

In a preferred embodiment, each bead comprises a single type of capture probe, although a plurality of individual capture probes are preferably attached to each bead. Similarly, preferred embodiments utilize more than one microsphere containing a unique capture probe; that is, there is redundancy built into the system by the use of subpopulations of microspheres, each microsphere in the subpopulation containing the same capture probe.

As will be appreciated by those in the art, the capture probes may either be synthesized directly on the beads, or they may be made and then attached after synthesis. In a preferred embodiment, linkers are used to attach the capture probes to the beads, to allow both good attachment, sufficient flexibility to allow good interaction with the target molecule, and to avoid undesirable binding reactions.

In a preferred embodiment, the capture probes are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the capture probes are synthesized first, and then covalently attached to the beads. As will be appreciated by those in the art, this will be done depending on the composition of the capture probes and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

When random arrays are used, an encoding/decoding system must be used. For example, when microsphere arrays are used, the beads are generally put onto the substrate randomly; as such there are several ways to correlate the functionality on the bead with its location, including the incorporation of unique optical signatures, generally fluorescent dyes, that could be used to identify the chemical functionality on any particular bead. This allows the synthesis of the candidate agents (i.e. compounds such as nucleic acids and antibodies) to be divorced from their placement on an array, i.e. the candidate agents may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art.

However, the drawback to these methods is that for a large array, the system requires a large number of different optical signatures, which may be difficult or time-consuming to utilize. Accordingly, the present invention provides several improvements over these methods, generally directed to methods of coding and decoding the arrays. That is, as will be appreciated by those in the art, the placement of the capture probes is generally random, and thus a coding/decoding system is required to identify the probe at each location in the array. This may be done in a variety of ways, as is more fully outlined below, and generally includes: a) the use a decoding binding ligand (DBL), generally directly labeled, that binds to either the capture probe or to identifier binding ligands (IBLs) attached to the beads; b) positional decoding, for example by either targeting the placement of beads (for example by using photoactivatable or photocleavable moieties to allow the selective addition of beads to particular locations), or by using either sub-bundles or selective loading of the sites, as are more fully outlined below; c) selective decoding, wherein only those beads that bind to a target are decoded; or d) combinations of any of these. In some cases, as is more fully outlined below, this decoding may occur for all the beads, or only for those that bind a particular target sequence. Similarly, this may occur either prior to or after addition of a target sequence. In addition, as outlined herein, the target sequences detected may be either a primary target sequence (e.g. a patient sample), or a reaction product from one of the methods described herein (e.g. an extended SBE probe, a ligated probe, a cleaved signal probe, etc.).

Once the identity (i.e. the actual agent) and location of each microsphere in the array has been fixed, the array is exposed to samples containing the target sequences, although as outlined below, this can be done prior to or during the analysis as well. The target sequences can hybridize (either directly or indirectly) to the capture probes as is more fully outlined below, and results in a change in the optical signal of a particular bead.

In the present invention, "decoding" does not rely on the use of optical signatures, but rather on the use of decoding binding ligands that are added during a decoding step. The decoding binding ligands will bind either to a distinct identifier binding ligand partner that is placed on the beads, or to the capture probe itself. The decoding binding ligands are either directly or indirectly labeled, and thus decoding occurs by detecting the presence of the label. By using pools of decoding binding ligands in a sequential fashion, it is possible to greatly minimize the number of required decoding steps.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the capture probe attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$–$10^{-6}$ M, with less than about $10^{-5}$ to $10^{-9}$ M being preferred and less than about $10^{-7}$-$10^{-9}$ M being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion-metal ion ligands or chelators pairs are also useful. Antigen-antibody pairs, enzymes and substrates or inhibitors, other protein-protein interacting pairs, receptor-ligands, complementary nucleic acids, and carbohydrates and their binding partners are also suitable binding pairs. Nucleic acid-nucleic acid binding proteins pairs are also useful. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL. For example, the IBL may be a fluorescent pH indicator whose emission intensity changes with pH. Similarly, the IBL may be a fluorescent ion indicator, whose emission properties change with ion concentration.

Alternatively, the IBL is a molecule whose color or luminescence properties change in the presence of various solvents. For example, the IBL may be a fluorescent molecule such as an ethidium salt whose fluorescence intensity increases in hydrophobic environments. Similarly, the IBL may be a derivative of fluorescein whose color changes between aqueous and nonpolar solvents.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

Alternatively, in a preferred embodiment, the IBL and the capture probe are the same moiety; thus, for example, as outlined herein, particularly when no optical signatures are used, the capture probe can serve as both the identifier and the agent. For example, in the case of nucleic acids, the bead-bound probe (which serves as the capture probe) can also bind decoder probes, to identify the sequence of the probe on the bead. Thus, in this embodiment, the DBLs bind to the capture probes.

In a preferred embodiment, the microspheres may contain an optical signature. That is, as outlined in U.S. Ser. Nos. 08/818,199 and 09/151,877, previous work had each subpopulation of microspheres comprising a unique optical signature or optical tag that is used to identify the unique capture probe of that subpopulation of microspheres; that is, decoding utilizes optical properties of the beads such that a bead comprising the unique optical signature may be distinguished from beads at other locations with different optical signatures. Thus the previous work assigned each capture probe a unique optical signature such that any microspheres comprising that capture probe are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

In a preferred embodiment, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use of optical signatures one some beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each capture probe, the number of possible unique codes is substantially increased. That is, by using one unique IBL per capture probe, the size of the array will be the number of unique IBLs (assuming no "reuse" occurs, as outlined below). However, by using a plurality of different IBLs per bead, n, the size of the array can be increased to 2, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has 210 possible variants However, as is more fully discussed below, the size of the array may be further increased if another parameter is included such as concentration or intensity; thus for example, if two different concentrations of the IBL are used, then the array size increases as 3. Thus, in this embodiment, each individual capture probe in the array is assigned a combination of IBLs, which can be added to the beads prior to the addition of the capture probe, after, or during the synthesis of the capture probe, i.e. simultaneous addition of IBLs and capture probe components.

Alternatively, the combination of different IBLs can be used to elucidate the sequence of the nucleic acid. Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

In this way, a sort of "bar code" for each sequence can be constructed; the presence or absence of each distinct IBL will allow the identification of each capture probe.

In addition, the use of different concentrations or densities of IBLs allows a "reuse" of sorts. if, for example, the bead comprising a first agent has a IX concentration of IBL, and a second bead comprising a second agent has a 10× concentration of IBL, using saturating concentrations of the corresponding labelled DBL allows the user to distinguish between the two beads.

Once the microspheres comprising the capture probes are generated, they are added to the substrate to form an array. It should be noted that while most of the methods described herein add the beads to the substrate prior to the assay, the order of making, using and decoding the array can vary. For example, the array can be made, decoded, and then the assay done. Alternatively, the array can be made, used in an assay, and then decoded; this may find particular use when only a few beads need be decoded. Alternatively, the beads can be added to the assay mixture, i.e. the sample containing the target sequences, prior to the addition of the beads to the substrate; after addition and assay, the array may be decoded. This is particularly preferred when the sample comprising the beads is agitated or mixed; this can increase the amount of target sequence bound to the beads per unit time, and thus (in the case of nucleic acid assays) increase the hybridization kinetics. This may find particular use in cases where the concentration of target sequence in the sample is low; generally, for low concentrations, long binding times must be used.

In general, the methods of making the arrays and of decoding the arrays is done to maximize the number of different candidate agents that can be uniquely encoded, The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads are removed.

In a preferred embodiment, when non-covalent methods are used to associate the beads with the array; a novel method of loading the beads onto the array is used. This method comprises exposing the array to a solution of particles (including microspheres and cells) and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the particles (beads, cells, etc.). The surface may comprise wells, as is described herein, or other types of sites on a patterned surface such that there is a differential affinity for the sites. This differential affinity results in a competitive process, such that particles that will associate more tightly are selected. Preferably, the entire surface to be "loaded" with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising samples, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stirring or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to attach the beads in a non-random or ordered way. For example, using photoactivatable attachment linkers or photoactivatable adhesives or masks, selected sites on the array may be sequentially rendered suitable for attachment, such that defined populations of beads are laid down.

The arrays of the present invention are constructed such that information about the identity of the capture probe is built into the array, such that the random deposition of the beads in the fiber wells can be "decoded" to allow identification of the capture probe at all positions. This may be done in a variety of ways, and either before, during or after the use of the array to detect target molecules.

Thus, after the array is made, it is "decoded" in order to identify the location of one or more of the capture probes, i.e. each subpopulation of beads, on the substrate surface.

In a preferred embodiment, pyrosequencing techniques are used to decode the array, as is generally described in "Nucleic Acid Sequencing Using Microsphere Arrays", filed Oct. 22, 1999 (no U.S.S.N. received yet), hereby expressly incorporated by reference.

In a preferred embodiment, a selective decoding system is used. In this case, only those microspheres exhibiting a change in the optical signal as a result of the binding of a target sequence are decoded. This is commonly done when the number of "hits", i.e. the number of sites to decode, is generally low. That is, the array is first scanned under experimental conditions in the absence of the target sequences. The sample containing the target sequences is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached capture probe may be done directly, for example using mass spectroscopy.

Alternatively, the identification may occur through the use of identifier moieties ("IMs"), which are similar to IBLs but need not necessarily bind to DBLs. That is, rather than elucidate the structure of the capture probe directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a non-fluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of attachment of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every capture probe is determined using decoder binding ligands (DBLs). As outlined above, DBLs are binding ligands that will either bind to identifier binding ligands, if present, or to the capture probes themselves, preferably when the capture probe is a nucleic acid or protein.

In a preferred embodiment, as outlined above, the DBL binds to the IBL.

In a preferred embodiment, the capture probes are single-stranded nucleic acids and the DBL is a substantially complementary single-stranded nucleic acid that binds (hybridizes) to the capture probe, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs.

Accordingly, the identification of the location of the individual beads (or subpopulations of beads) is done using one or more decoding steps comprising a binding between the labeled DBL and either the IBL or the capture probe (i.e. a hybridization between the candidate probe and the decoder probe when the capture probe is a nucleic acid). After decoding, the DBLs can be removed and the array can be used; however, in some circumstances, for example when the DBL binds to an IBL and not to the capture probe, the removal of the DBL is not required (although it may be desirable in some circumstances). In addition, as outlined herein, decoding may be done either before the array is used to in an assay, during the assay, or after the assay.

In one embodiment, a single decoding step is done. In this embodiment, each DBL is labeled with a unique label, such that the number of unique tags is equal to or greater than the number of capture probes (although in some cases, "reuse" of the unique labels can be done, as described herein; similarly, minor variants of candidate probes can share the same decoder, if the variants are encoded in another dimension, i.e. in the bead size or label). For each capture probe or IBL, a DBL is made that will specifically bind to it and contains a unique tag, for example one or more fluorochromes. Thus, the identity of each DBL, both its composition (i.e. its sequence when it is a nucleic acid) and its label, is known. Then, by adding the DBLs to the array containing the capture probes Under conditions which allow the formation of complexes (termed hybridization complexes when the components are nucleic acids) between the DBLs and either the capture probes or the IBLs, the location of each DBL can be elucidated. This allows the identification of the location of each capture probe; the random array has been decoded. The DBLs can then be removed, if necessary, and the target sample applied.

In a preferred embodiment, the number of unique labels is less than the number of unique capture probes, and thus a sequential series of decoding steps are used. In this embodiment, decoder probes are divided into n sets for decoding. The number of sets corresponds to the number of unique tags. Each decoder probe is labeled in n separate reactions with n distinct tags. All the decoder probes share the same n tags. The decoder probes are pooled so that each pool contains only one of the n tag versions of each decoder, and no two decoder probes have the same sequence of tags across all the pools. The number of pools required for this to be true is determined by the number of decoder probes and the n. Hybridization of each pool to the array generates a signal at every address. The sequential hybridization of each pool in turn will generate a unique, sequence-specific code for each candidate probe. This identifies the candidate probe at each address in the array. For example, if four tags are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

An example is illustrative. Assuming an array of 16 probe nucleic acids (numbers 1-16), and four unique tags (four different fluors, for example; labels A-D). Decoder probes 1-16 are made that correspond to the probes on the beads. The first step is to label decoder probes 1-4 with tag A, decoder probes 5-8 with tag B, decoder probes 9-12 with tag C, and decoder probes 13-16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc. In one embodiment, the decoder probes are labeled in situ; that is, they need not be labeled prior to the decoding reaction. In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the capture probes, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different capture probes. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different capture probe (or the subpopulations each comprise a different capture probe), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each capture probe is determined, generally through the use of DBLs. The second sublibrary is then added, and the location of each capture probe is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target sequences different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

In a preferred embodiment, decoding of self-assembled random arrays is done on the bases of pH titration. In this embodiment, in addition to capture probes, the beads comprise optical signatures, wherein the optical signatures are generated by the use of pH-responsive dyes (sometimes referred to herein as "ph dyes") such as fluorophores. This embodiment is similar to that outlined in PCT US98/05025 and U.S. Ser. No. 09/151,877, both of which are expressly incorporated by reference, except that the dyes used in the present invention exhibits changes in fluorescence intensity (or other properties) when the solution pH is adjusted from below the pKa to above the pKa (or vice versa). In a preferred embodiment, a set of pH dyes are used, each with a different pKa, preferably separated by at least 0.5 pH units. Preferred embodiments utilize a pH dye set of pKa's of 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11, and 11.5. Each bead can contain any subset of the pH dyes, and in this way a unique code for the capture probe is generated. Thus, the decoding of an array is achieved by titrating the array from pH 1 to pH 13, and measuring the fluorescence signal from each bead as a function of solution pH.

Thus, the present invention provides array compositions comprising a substrate with a surface comprising discrete sites. A population of microspheres is distributed on the sites, and the population comprises at least a first and a second subpopulation. Each subpopulation comprises a capture probe, and, in addition, at least one optical dye with a given pKa. The pKas of the different optical dyes are different.

In a preferred embodiment, "random" decoding probes can be made. By sequential hybridizations or the use of multiple labels, as is outlined above, a unique hybridization pattern can be generated for each sensor element. This allows all the beads representing a given clone to be identified as belonging to the same group. In general, this is done by using random or partially degenerate decoding probes, that bind in a sequence-dependent but not highly sequence-specific manner. The process can be repeated a number of times, each time using a different labeling entity, to generate a different pattern of signals based on quasi-specific interactions. In this way, a unique optical signature is eventually built up for each sensor element. By applying pattern recognition or clustering algorithms to the optical signatures, the beads can be grouped into sets that share the same signature (i.e. carry the same probes).

In order to identify the actual sequence of the clone itself, additional procedures are required; for example, direct sequencing can be done, or an ordered array containing the clones, such as a spotted cDNA array, to generate a "key" that links a hybridization pattern to a specific clone.

Alternatively, clone arrays can be decoded using binary decoding with vector tags. For example, partially randomized oligos are cloned into a nucleic acid vector (e.g. plasmid, phage, etc.). Each oligonucleotide sequence consists of a subset of a limited set of sequences. For example, if the limited set comprises 10 sequences, each oligonucleotide may have some subset (or all of the 10) sequences. Thus each of the 10 sequences can be present or absent in the oligonucleotide. Therefore, there are 270 or 1,024 possible combinations. The sequences may overlap, and minor variants can also be represented (e.g. A, C, T and G substitutions) to increase the number of possible combinations. A nucleic acid library is cloned into a vector containing the random code sequences. Alternatively, other methods such as PCR can be used to add the tags. In this way it is possible to use a small number of oligo decoding probes to decode an array of clones.

As will be appreciated by those in the art, the systems of the invention may take on a large number of different configurations, as is generally depicted in the Figures. In general, there are three types of systems that can be used: (1) "non-sandwich" systems (also referred to herein as "direct" detection) in which the target sequence itself is labeled with detectable labels (again, either because the primers comprise labels or due to the incorporation of labels into the newly synthesized strand); (2) systems in which label probes directly bind to the target analytes; and (3) systems in which label probes are indirectly bound to the target sequences, for example through the use of amplifier probes.

Detection of the reactions of the invention, including the direct detection of products and indirect detection utilizing label probes (i.e. sandwich assays), is preferably done by detecting assay complexes comprising detectable labels, which can be attached to the assay complex in a variety of ways, as is more fully described below.

Once the target sequence has preferably been anchored to the array, an amplifier probe is hybridized to the target sequence, either directly, or through the use of one or more label extender probes, which serves to allow "generic" amplifier probes to be made. As for all the steps outlined herein, this may be done simultaneously with capturing, or sequentially. Preferably, the amplifier probe contains a multiplicity of amplification sequences, although in some embodiments, as described below, the amplifier probe may contain only a single amplification sequence, or at least two amplification sequences. The amplifier probe may take on a number of different forms; either a branched conformation, a dendrimer conformation, or a linear "string" of amplification sequences. Label probes comprising detectable labels (preferably but not required to be fluorophores) then hybridize to the amplification sequences (or in some cases the label probes hybridize directly to the target sequence), and the labels detected, as is more fully outlined below.

Accordingly, the present invention provides compositions comprising an amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single-stranded nucleic acid amplification sequence, with a multiplicity of amplification sequences being preferred.

Amplifier probes comprise a first probe sequence that is used, either directly or indirectly, to hybridize to the target sequence. That is, the amplifier probe itself may have a first probe sequence that is substantially complementary to the target sequence, or it has a first probe sequence that is substantially complementary to a portion of an additional probe, in this case called a label extender probe, that has a first portion that is substantially complementary to the target sequence. In a preferred embodiment, the first probe sequence of the amplifier probe is substantially complementary to the target sequence.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

In a preferred embodiment, the amplifier probe does not hybridize to the sample target sequence directly, but instead hybridizes to a first portion of a label extender probe. This is particularly useful to allow the use of "generic" amplifier probes, that is, amplifier probes that can be used with a variety of different targets. This may be desirable since several of the amplifier probes require special synthesis techniques. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'-3' orientation of the target or probe sequences. For example, assuming a 5'-3' orientation of the complementary target sequence, the first portion may be located either 5' to the second portion, or 3 to the second portion. For convenience herein, the order of probe sequences are generally shown from left to right.

In a preferred embodiment, more than one label extender probe-amplifier probe pair may be used, that is, n is more than 1. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce non-specific binding, as is generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below. Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to which at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end, either directly or with short intervening sequences to form a polymer. As with the other amplifier configurations, there may be additional sequences or moieties between the amplification sequences. In one embodiment, the linear amplifier probe has a single amplification sequence.

In addition, the amplifier probe may be totally linear, totally branched, totally dendrimeric, or any combination thereof.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

In addition, the compositions of the invention may include "preamplifier" molecules, which serves a bridging moiety between the label extender molecules and the amplifier probes. In this way, more amplifier and thus more labels are ultimately bound to the detection probes. Preamplifier molecules may be either linear or branched, and typically contain in the range of about 30-3000 nucleotides.

Thus, label probes are either substantially complementary to an amplification sequence or to a portion of the target sequence.

Detection of the nucleic acid reactions of the invention, including the direct detection of genotyping products and indirect detection utilizing label probes (i.e. sandwich assays), is done by detecting assay complexes comprising labels.

In a preferred embodiment, several levels of redundancy are built into the arrays of the invention. Building redundancy into an array gives several significant advantages, including the ability to make quantitative estimates of confidence about the data and significant increases in sensitivity. Thus, preferred embodiments utilize array redundancy. As will be appreciated by those in the art, there are at least two types of redundancy that can be built into an array: the use of multiple identical sensor elements (termed herein "sensor redundancy"), and the use of multiple sensor elements directed to the same target analyte, but comprising different chemical functionalities (termed herein "target redundancy"). For example, for the detection of nucleic acids, sensor redundancy utilizes of a plurality of sensor elements such as beads comprising identical binding ligands such as probes. Target redundancy utilizes sensor elements with different probes to the same target: one probe may span the first 25 bases of the target, a second probe may span the second 25 bases of the target, etc. By building in either or both of these types of redundancy into an array, significant benefits are obtained.

For example, a variety of statistical mathematical analyses may be done.

In addition, while this is generally described herein for bead arrays, as will be appreciated by those in the art, this techniques can be used for any type of arrays designed to detect target analytes. Furthermore, while these techniques are generally described for nucleic acid systems, these techniques are useful in the detection of other binding ligand/target analyte systems as well.

In a preferred embodiment, sensor redundancy is used. In this embodiment, a plurality of sensor elements, e.g. beads, comprising identical bioactive agents are used. That is, each subpopulation comprises a plurality of beads comprising identical bioactive agents (e.g. binding ligands). By using a number of identical sensor elements for a given array, the optical signal from each sensor element can be combined and any number of statistical analyses run, as outlined below. This can be done for a variety of reasons. For example, in time varying measurements, redundancy can significantly reduce the noise in the system. For non-time based measurements, redundancy can significantly increase the confidence of the data.

In a preferred embodiment, a plurality of identical sensor elements are used. As will be appreciated by those in the art, the number of identical sensor elements will vary with the application and use of the sensor array. In general, anywhere from 2 to thousands may be used, with from 2 to 100 being preferred, 2 to 50 being particularly preferred and from 5 to 20 being especially preferred. In general, preliminary results indicate that roughly 10 beads gives a sufficient advantage, although for some applications, more identical sensor elements can be used.

Once obtained, the optical response signals from a plurality of sensor beads within each bead subpopulation can be manipulated and analyzed in a wide variety of ways, including baseline adjustment, averaging, standard deviation analysis, distribution and cluster analysis, confidence interval analysis, mean testing, etc.

In a preferred embodiment, the first manipulation of the optical response signals is an optional baseline adjustment. In a typical procedure, the standardized optical responses are adjusted to start at a value of 0.0 by subtracting the integer 1.0 from all data points. Doing this allows the baseline-loop data to remain at zero even when summed together and the random response signal noise is canceled out. When the sample is a fluid, the fluid pulse-loop temporal region, however, frequently exhibits a characteristic change in response, either positive, negative or neutral, prior to the sample pulse and often requires a baseline adjustment to overcome noise associated with drift in the first few data points due to charge buildup in the CCD camera. If no drift is present, typically the baseline from the first data point for each bead sensor is subtracted from all the response data for the same bead. If drift is observed, the average baseline from the first ten data points for each bead sensor is substracted from the all the response data for the same bead. By applying this baseline adjustment, when multiple bead responses are added together they can be amplified while the baseline remains at zero. Since all beads respond at the same time to the sample (e.g. the sample pulse), they all see the pulse at the exact same time and there is no registering or adjusting needed for overlaying their responses. In addition, other types of baseline adjustment may be done, depending on the requirements and output of the system used.

Once the baseline has been adjusted, a number of possible statistical analyses may be run to generate known statistical parameters. Analyses based on redundancy are known and generally described in texts such as Freund and Walpole, Mathematical Statistics, Prentice Hall, Inc. New Jersey, 1980, hereby incorporated by reference in its entirety.

In a preferred embodiment, signal summing is done by simply adding the intensity values of all responses at each time point, generating a new temporal response comprised of the sum of all bead responses. These values can be baseline-adjusted or raw. As for all the analyses described herein, signal summing can be performed in real time or during post-data acquisition data reduction and analysis. In one embodiment, signal summing is performed with a commercial spreadsheet program (Excel, Microsoft, Redmond, Wash.) after optical response data is collected.

In a preferred embodiment, cumulative response data is generated by simply adding all data points in successive time intervals. This final column, comprised of the sum of all data points at a particular time interval, may then be compared or plotted with the individual bead responses to determine the extent of signal enhancement or improved signal-to-noise ratios.

In a preferred embodiment, the mean of the subpopulation (i.e. the plurality of identical beads) is determined, using the well known Equation 1:

$$\mu = \sum \frac{x_i}{n} \qquad \text{Equation 1}$$

In some embodiments, the subpopulation may be redefined to exclude some beads if necessary (for example for obvious outliers, as discussed below).

In a preferred embodiment, the standard deviation of the subpopulation can be determined, generally using Equation 2 (for the entire subpopulation) and Equation 3 (for less than the entire subpopulation):

$$\sigma = \sqrt{\frac{\sum (x_i - \mu)^2}{n}} \qquad \text{Equation 2}$$

$$s = \sqrt{\frac{\sum (x_i - \bar{x})^2}{n-1}} \qquad \text{Equation 3}$$

As for the mean, the subpopulation may be redefined to exclude some beads if necessary (for example for obvious outliers, as discussed below).

In a preferred embodiment, statistical analyses are done to evaluate whether a particular data point has statistical validity within a subpopulation by using techniques including, but not limited to, t distribution and cluster analysis. This may be done to statistically discard outliers that may otherwise skew the result and increase the signal-to-noise ratio of any particular experiment. This may be done using Equation 4:

$$t = \frac{\bar{x} - \mu}{s/\sqrt{n}} \qquad \text{Equation 4}$$

In a preferred embodiment, the quality of the data is evaluated using confidence intervals, as is known in the art. Confidence intervals can be used to facilitate more comprehensive data processing to measure the statistical validity of a result.

In a preferred embodiment, statistical parameters of a subpopulation of beads are used to do hypothesis testing. One application is tests concerning means, also called mean testing. In this application, statistical evaluation is done to determine whether two subpopulations are different. For example, one sample could be compared with another sample for each subpopulation within an array to determine if the variation is statistically significant.

In addition, mean testing can also be used to differentiate two different assays that share the same code. If the two assays give results that are statistically distinct from each other, then the subpopulations that share a common code can be distinguished from each other on the basis of the assay and the mean test, shown below in Equation 5:

$$z = \frac{\overline{x_1} - \overline{x_2}}{\sqrt{\frac{\sigma_1^2}{n_1} + \frac{\sigma_2^2}{n_2}}} \qquad \text{Equation 5}$$

Furthermore, analyzing the distribution of individual members of a subpopulation of sensor elements may be done. For example, a subpopulation distribution can be evaluated to determine whether the distribution is binomial, Poisson, hypergeometric, etc.

In addition to the sensor redundancy, a preferred embodiment utilizes a plurality of sensor elements that are directed to a single target analyte but yet are not identical. For example, a single target nucleic acid analyte may have two or more sensor elements each comprising a different probe. This adds a level of confidence as non-specific binding interactions can be statistically minimized. When nucleic acid target analytes are to be evaluated, the redundant nucleic acid probes may be overlapping, adjacent, or spatially separated. However, it is preferred that two probes do not compete for a single binding site, so adjacent or separated probes are preferred. Similarly, when proteinaceous target analytes are to be evaluated, preferred embodiments utilize bioactive agent binding agents that bind to different parts of the target. For example, when antibodies (or antibody fragments) are used as bioactive agents for the binding of target proteins, preferred embodiments utilize antibodies to different epitopes.

In this embodiment, a plurality of different sensor elements may be used, with from about 2 to about 20 being preferred, and from about 2 to about 10 being especially preferred, and from 2 to about 5 being particularly preferred, including 2, 3, 4 or 5. However, as above, more may also be used, depending on the application.

As above, any number of statistical analyses may be run on the data from target redundant sensors.

One benefit of the sensor element summing (referred to herein as "bead summing" when beads are used), is the increase in sensitivity that can occur.

In addition, the present invention is directed to the use of adapter sequences to assemble arrays comprising target analytes. Including non-nucleic acid target analytes. By "target analyte" or "analyte" or grammatical equivalents herein is meant any molecule, compound or particle to be detected. As outlined below, target analytes preferably bind to binding ligands, as is more fully described below. As will be appreciated by those in the art, a large number of analytes may be detected using the present methods; basically, any target analyte for which a binding ligand, described below, may be made may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.): therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids arid amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, a-fetoprotein, thyroxin, thyroid stimulating hormone (TSH), antithrombin, antibodies to pharmaceuticals (including antiepileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppressants, abused drugs (amphetamine, methamphetamine, cannabinoids, cocaine and opiates) and antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cortisol, estradiol, follicle stimulating hormone (FSH), thyroid-stimulating hormone (TSH), luteinizing hormone (LH), progesterone, testosterone, and (4) other proteins (including a-fetoprotein, carcinoembryonic antigen CEA.

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

The adapter sequences may be chosen as outlined above. These adapter sequences can then be added to the target analytes using a variety of techniques. In general, as described above, noncovalent attachment using binding partner pairs may be done, or covalent attachment using chemical moieties (including linkers).

Once the adapter sequences are associated with the target analyte, including target nucleic acids, the compositions are added to an array. In one embodiment a plurality of hybrid adapter sequence/target analytes are pooled prior to addition to an array. All of the methods and compositions herein are drawn to compositions and methods for detecting the presence of target analytes, particularly nucleic acids, using adapter arrays.

Advantages of using adapters include but are not limited to, for example, the ability to create universal arrays. That is, a single array is utilized with each capture probe designed to hybridize with a specific adapter. The adapters are joined to any number of target analytes, such as nucleic acids, as is described herein. Thus, the same array is used for vastly different target analytes. Furthermore, hybridization of adapters with capture probes results in non-covalent attachment of the target nucleic acid to the microsphere. As such, the target nucleic/adapter hybrid is easily removed, and the microsphere/capture probe can be re-used. In addition, the construction of kits is greatly facilitated by the use of adapters. For example, arrays or microspheres can be prepared that comprise the capture probe; the adapters can be packaged along with the microspheres for attachment to any target analyte of interest. Thus, one need only attach the adapter to the target analyte and disperse on the array for the construction of an array of target analytes.

Once made, the compositions of the invention find use in a number of applications. In a preferred embodiment, the compositions are used to probe a sample solution for the presence or absence of a target sequence, including the quantification of the amount of target sequence present.

For SNP analysis, the ratio of different labels at a particular location on the array indicates the homozygosity or heterozygosity of the target sample, assuming the same concentration of each readout probe is used. Thus, for example, assuming a first readout probe comprising a first base at the readout position with a first detectable label and a second readout probe comprising a second base at the readout position with a second detectable label, equal signals (roughly 1:1 (taking into account the different signal intensities of the different labels, different hybridization efficiencies, and other reasons)) of the first and second labels indicates a heterozygote. The absence of a signal from the first label (or a ratio of approximately 0:1) indicates a homozygote of the second detection base; the absence of a signal from the second label (or a ratio of approximately 1:0) indicates a homozygote for the first detection base. As is appreciated by those in the art, the actual ratios for any particular system are generally determined empirically. The ratios also allow for SNP quantitation The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998): see also Schafer et al., Nature Biotechnology 16:33-39 (1998). The compositions of the present invention may easily be substituted for the arrays of the prior art.

Generally, a sample containing a target analyte (whether for detection of the target analyte or screening for binding partners of the target analyte) is added to the array, under conditions suitable for binding of the target analyte to at least one of the capture probes, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties.

In a preferred embodiment, intercalators may be used; since intercalation generally only occurs in the presence of double stranded nucleic acid, only in the presence of target hybridization will the label light up. Thus, upon binding of the target analyte to a capture probe, there is a new optical signal generated at that site, which then may be detected.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In addition, the present invention provides kits for the reactions of the invention, comprising components of the assays as outlined herein. In addition, a variety of other reagents may be included in the assays or the kits. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite activity.

All references cited herein are incorporated by reference in their entirety.

What is claimed:

1. A method of detecting a plurality of target nucleic acid sequences, comprising:
 a) providing one or more first solid supports comprising a plurality of target sequences that are immobilized to said first solid supports, wherein said first solid supports comprise a plurality of beads;
 b) hybridizing a plurality of different first primers to first portions of said plurality of target sequences, wherein each of said different first primers comprises an adapter sequence exogenous to said target sequences;

c) hybridizing a plurality of different second primers to second portions of said plurality of target sequences, thereby forming a plurality of hybridization complexes;

d) extending said first or said second primers, and ligating said first and second primers together to form a plurality of different modified primers;

e) hybridizing said adapter sequences of said modified primers or their complements to an array of capture probes attached to discrete sites on a second solid support;

f) modifying said capture probes by polymerase extension, and g) detecting said modified capture probes, thereby detecting said plurality of target nucleic acid sequences.

2. The method of claim 1, wherein after said extending of said first or second primers, hybridizing said plurality of different modified primers with a plurality of amplifier probes complementary to said plurality of first and second primers and amplifying said different modified primers, thereby forming amplified products comprising said adapter sequences or their complements.

3. The method of claim 2, further comprising hybridizing said adapter sequences of said amplified products or their complements to said array of capture probes.

4. The method of claim 2, comprising detecting a label attached to said amplified products.

5. The method of claim 2, wherein said amplifying comprises a polymerase chain reaction.

6. The method of claim 2, further comprising extending said amplifier probes with a polymerase and NTPs.

7. The method of claim 2, wherein said amplifier probes further comprise a label.

8. The method of claim 7, wherein said label comprises a biotin tag that allows isolation of extended amplifier probes.

9. The method of claim 2, further comprising a wash step prior to amplifying said different modified primers.

10. The method of claim 2, further comprising extending said amplifier probes with a polymerase and dNTPs.

11. The method of claim 1, further comprising identifying a nucleotide at a detection position for each of said target nucleic acid sequences, wherein a primer of said plurality of first primers or said plurality of second primers is complementary to said detection position.

12. The method of claim 1, wherein said target sequences are attached to said first solid supports.

13. The method of claim 1, wherein said array comprises a population of beads comprising said capture probes.

14. The method of claim 13, wherein said beads are associated with individual sites of a substrate.

15. The method of claim 14, wherein each of said sites is configured to have a single associated bead.

16. The method of claim 14, wherein said substrate comprises a fiber optic bundle.

17. The method of claim 1, wherein said array is made by a method selected from the group consisting of a spotting technique, photolithographic technique, and printing technique.

18. The method of claim 1, comprising detecting a label attached to said modified primers.

19. The method of claim 1, comprising detecting a fluorescent label.

20. The method of claim 1, wherein said plurality of target sequences are immobilized by covalent attachment to said first solid supports.

21. The method of claim 1, wherein said capture probes are covalently attached to said second solid support.

22. The method of claim 1, wherein each of said target sequences comprises a locus having a single nucleotide polymorphism (SNP) allele.

23. The method of claim 22, wherein said plurality of said first primers comprise allele specific primers and said plurality of second primers comprise locus specific primers.

24. The method of claims 23, wherein the terminal base of said allele specific primers correspond to said SNP allele.

25. The method of claim 23, further comprising a plurality of second allele specific primers, wherein said plurality of allele specific primer comprises a match for said SNP and said plurality of second allele specific primers comprises a mismatch for said SNP at said detection position.

26. The method of claims 23, wherein step (d) comprises extending said allele specific probe of said hybridization complexes to add a base to basepair with said SNP.

27. The method of claim 23, wherein said detecting of step (g) indicates a SNP clinically related to a phenotypic variant.

28. The method of claim 23, wherein said detecting of step (g) determines the genotype of a target sequence that is an indicator of a disease.

29. The method of claim 1, wherein said detecting of step (g) indicates the amount of a target sequence present in said plurality of nucleic acid sequences.

30. The method of claim 1, wherein said detecting of step (g) determines the presence of a target sequence that is an indicator of a disease.

31. The method of claim 1, wherein said first and second primers are separated by one or more bases.

* * * * *